US012315597B2

(12) United States Patent
Craig et al.

(10) Patent No.: US 12,315,597 B2
(45) Date of Patent: May 27, 2025

(54) METHODS AND SYSTEMS FOR ASSESSING THE RISK OF GLAUCOMA

(71) Applicants: The Flinders University of South Australia, Bedford Park (AU); The Council of the Queensland Institute of Medical Research, Herston (AU); University of Tasmania, Sandy Bay (AU); Southern Adelaide Local Health Network, Bedford Park (AU); Jamie Evan Craig, Walkerville (AU)

(72) Inventors: Jamie Evan Craig, Walkerville (AU); Stuart MacGregor, Kedron (AU); Alex William Hewitt, Bonnet Hill (AU)

(73) Assignees: The Flinders University of South Australia, Bedford Park (AU); The Council of the Queensland Institute of Medical Research, Herston (AU); University of Tasmania, Sandy Bay (AU); Southern Adelaide Local Health Network, Sandy Bay (AU)

( * ) Notice: Subject to any disclaimer, the term of this patent is extended or adjusted under 35 U.S.C. 154(b) by 1044 days.

(21) Appl. No.: 17/253,833

(22) PCT Filed: Jun. 20, 2019

(86) PCT No.: PCT/AU2019/050635
§ 371 (c)(1),
(2) Date: Dec. 18, 2020

(87) PCT Pub. No.: WO2019/241844
PCT Pub. Date: Dec. 26, 2019

(65) Prior Publication Data
US 2021/0118525 A1    Apr. 22, 2021

(30) Foreign Application Priority Data
Jun. 20, 2018    (AU) .............................. 2018902206

(51) Int. Cl.
*G16B 20/20* (2019.01)
*G16B 25/10* (2019.01)
*G16B 40/00* (2019.01)

(52) U.S. Cl.
CPC .............. *G16B 20/20* (2019.02); *G16B 25/10* (2019.02); *G16B 40/00* (2019.02)

(58) Field of Classification Search
CPC ........ G16B 20/20; G16B 25/10; G16B 40/00; G16B 20/00; C12Q 2600/156; C12Q 1/6883; C12Q 2600/118
See application file for complete search history.

(56) References Cited

U.S. PATENT DOCUMENTS

2003/0068632 A1    4/2003    Garchon
2015/0315645 A1    11/2015    Gaasterland et al.

FOREIGN PATENT DOCUMENTS

WO    WO-2011004404 A1 *    1/2011    ........... C12Q 1/6883

OTHER PUBLICATIONS

Carbonaro F. Optic disc planimetry, corneal hysteresis, central corneal thickness, and intraocular pressure as risk factors for glaucoma. American Journal of Ophthalmology 157(2): 441-446. (Year: 2014).*
Hysi PG. Genome-wide analysis of multi-ancestry cohorts identifies new loci influencing intraocular pressure and susceptibility to glaucoma. Nature Genetics 46(10: 1126-1132. (Year: 2014).*
Mabuchi F. Association between genetic variants associated with vertical cup-to-disc ratio and phenotypic features of primary open-angle glaucoma. Ophthalmology 119(9): 1819-1825. (Year: 2012).*
Souzeau E. Myocilin predictive genetic testing for primary open-angle glaucoma leads to early identification of at-risk individuals. Ophthalmology 124(3): 303-309. (Year: 2016).*
Abu-Amero et al., "An Updated Review on the Genetics of Primary Open Angle Glaucoma," *International Journal of Molecular Sciences*, vol. 16, pp. 28886-28911, 2015.
Extended European Search Report dated Feb. 24, 2022, issued for corresponding European Application No. 19823125.0 (11 pages).
Mabuch et al., "Additive effects of genetic variants associated with intraocular pressure in primary open-angle glaucoma," *PLoS One*, vol. 12, No. 8, Article e0183709, 2017 (13 pages).
Nannini et al., "Genetic Risk Score Is Associated with Vertical Cup-to-Disc Ratio and Improves Prediction of Primary Open-Angle Glaucoma in Latinos," *Ophthalmology*, vol. 125, No. 6, pp. 815-821, 2018.
Tham et al., "Aggregate Effects of Intraocular Pressure and Cup-to-Disc Ratio Genetic Variants on Glaucoma in a Multiethnic Asian Population," *Ophthalmology*, vol. 122, No. 6, pp. 1149-1157, 2015.

(Continued)

*Primary Examiner* — Karlheinz R. Skowronek
*Assistant Examiner* — Robert J. Kallal
(74) *Attorney, Agent, or Firm* — Klarquist Sparkman, LLP

(57) ABSTRACT

The present disclosure relates to methods and systems for assessing the risk of glaucoma in a subject. In certain embodiments, the present disclosure provide a method of assessing the risk of primary open angle glaucoma in a subject, the method comprises determining a risk score for primary open angle glaucoma in the subject on the basis of the genetic content of the subject at a plurality of selected genetic loci or markers and thereby assessing the risk of primary open angle glaucoma in the subject, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio. Other embodiments are described.

13 Claims, 18 Drawing Sheets

(56) References Cited

OTHER PUBLICATIONS

Ghanbari et al., "A Genome-Wide Scan for MicroRNA-Related Genetic Variants Associated With Primary Open-Angle Glaucoma," *Investigation Ophthalmology & Visual Science*, vol. 58, pp. 5368-5377, 2017.
Gharahkhani et al., "Analysis combining correlated glaucoma traits identifies five new risk loci for open-angle glaucoma," *Scientific Reports*, 8:3124, 2018 (12 pages).
Gibson et al., "Genome-wide association study of primary open angle glaucoma risk and quantitative traits," *Molecular Vision*, vol. 18, pp. 1083-1092, 2012.
Philomenadin et al., "Genetic Association of SNPs near ATOH7, CARD10, CDKN2B, CDC7 and SIX1/SIX6 with the Endophenotypes of Primary Open Angle Glaucoma in Indian Population," *PLoS One*, 10(3):e0119703, 2015 (12 pages).
Ramdas et al., "Genetic architecture of open angle glaucoma and related. Determinants," *Journal of Medical Genetics*, vol. 48, pp. 190-196, 2011.
Springelkamp et al., "New insights into the genetics of primary open-angle. Glaucoma based on meta-analyses of intraocular pressure and optic disc characteristics," *Human Molecular Genetics*, vol. 25, No. 2, pp. 438-453, 2017.
Tham et al., "Aggregate Effects of Intraocular Pressure and Cup-to-Disc Ratio Genetic Variants on Glaucoma in a Multiethnic Asian Population," *Ophthalmology*, vol. 122, pp. 1149-1157, 2015.

\* cited by examiner

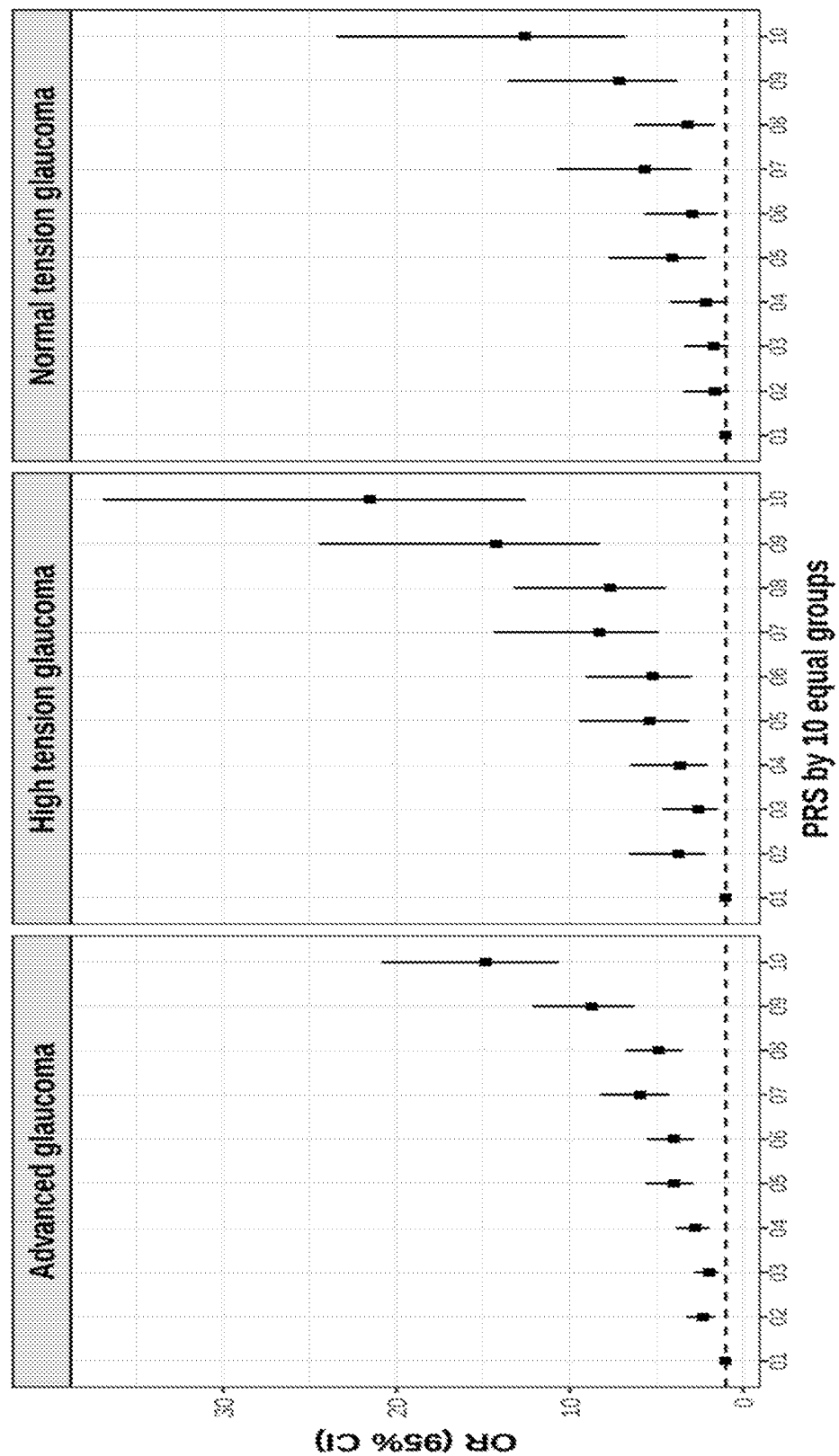

Fig. 8
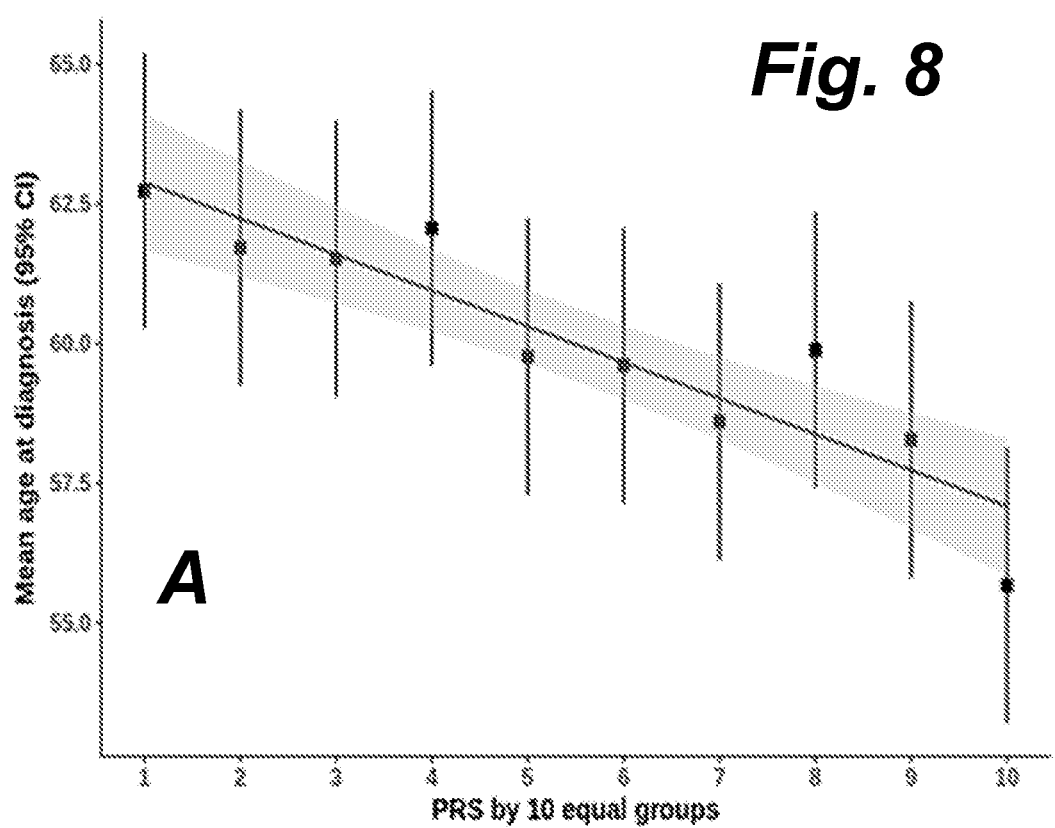
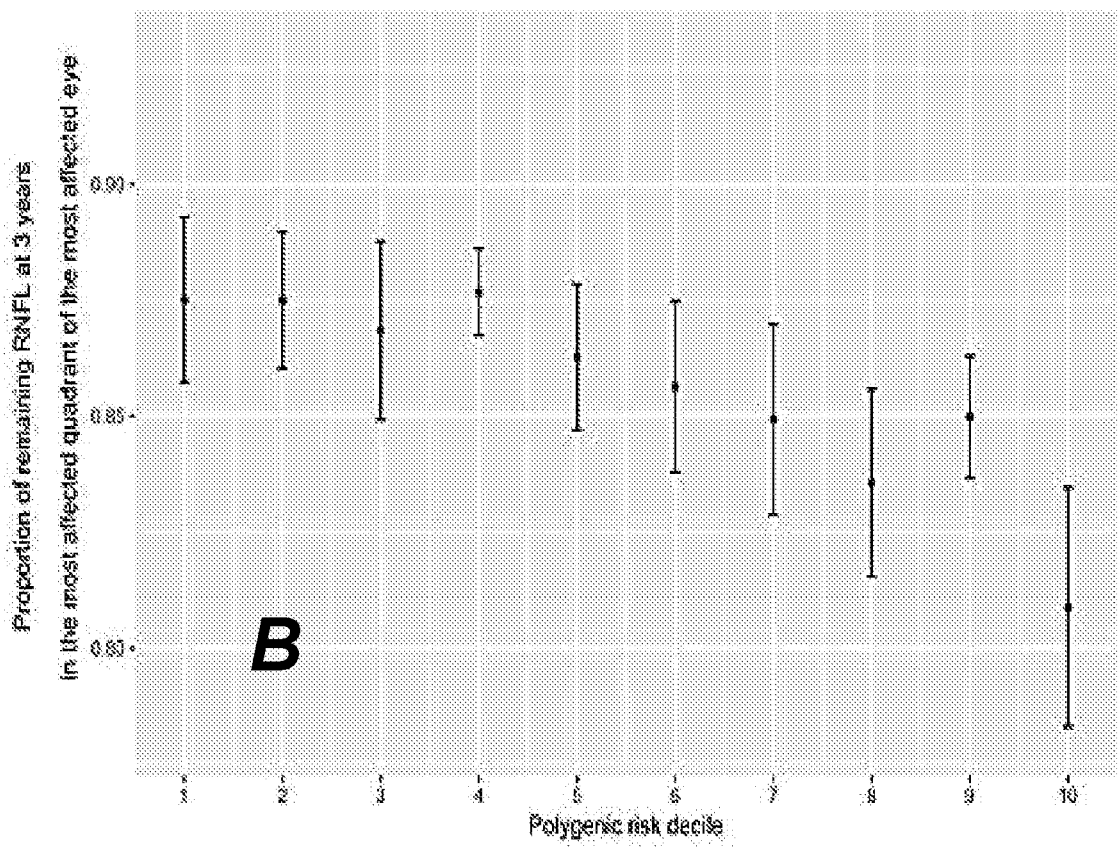

FIG. 10

| SNP | Chr | Position | EA | NEA | Freq_EA | BETA | SE | P | Near Gene | novel |
|---|---|---|---|---|---|---|---|---|---|---|
| rs12024620 | 1 | 33493822 | C | T | | 0.94 | -0.01 | 0.0018 | 1.2E-10 PRDM16 | 1 |
| rs34151819 | 1 | 68773919 | C | T | | 0.98 | 0.02 | 0.0035 | 5.4E-10 WLS | 1 |
| rs1417488 | 1 | 218523730 | C | T | | 0.75 | -0.01 | 0.0011 | 2.8E-09 TGFB2 | 1 |
| rs77271342 | 1 | 227677723 | A | CT | | 0.94 | -0.01 | 0.0019 | 6.5E-14 ZNF670 | 1 |
| rs76995695 | 1 | 58934570 | C | G | | 0.78 | 0.01 | 0.0011 | 3.9E-10 EFEMP1 | 1 |
| rs2880192 | 2 | 111683818 | A | G | | 0.85 | 0.01 | 0.00094 | 9.0E-12 ACOXL | 1 |
| rs1578050 | 2 | 163384527 | A | G | | 0.42 | 0.01 | 0.00092 | 4.1E-09 FMNL2 | 1 |
| rs4558692 | 3 | 25066225 | C | C | | 0.47 | -0.01 | 0.00089 | 2.6E-09 RARB | 1 |
| rs34010125 | 3 | 32878682 | T | A | | 0.89 | -0.01 | 0.00095 | 3.3E-10 TRIM71 | 1 |
| 3:88379094_AT_A | 3 | 88379094 | AT | A | | 0.45 | -0.01 | 0.0009 | 7.8E-10 C3orf38 | 1 |
| rs4628176 | 3 | 98972935 | G | A | | 0.41 | -0.01 | 0.00092 | 4.5E-15 MIR548G | 1 |
| rs9827694 | 3 | 108648298 | G | A | | 0.02 | 0.01 | 0.0012 | 8.6E-10 AB33BP | 1 |
| rs140351982 | 3 | 134089790 | G | T | | 0.99 | -0.03 | 0.0046 | 4.9E-09 AMOTL2 | 1 |
| rs2162137 | 4 | 55205856 | C | G | | 0.34 | 0.01 | 0.00094 | 1.8E-13 GSX2 | 1 |
| rs62335773 | 4 | 55394682 | G | GA | | 0.79 | -0.01 | 0.0011 | 3.7E-12 PDGFRA | 1 |
| rs198653 | 5 | 55578821 | G | A | | 0.48 | -0.01 | 0.00097 | 1.1E-09 ANKRD55 | 1 |
| rs36372 | 5 | 55744230 | T | C | | 0.24 | -0.01 | 0.0011 | 1.2E-09 LOC101926714 | 1 |
| rs17749004 | 5 | 128918456 | T | C | | 0.25 | -0.01 | 0.001 | 2.7E-08 ADAMTS19 | 1 |
| 5:133093260_GA | 5 | 133093260 | GA | G | | 0.84 | -0.01 | 0.0013 | 8.1E-12 VDAC1 | 1 |
| rs2762225 | 6 | 1851135 | C | T | | 0.07 | -0.01 | 0.0014 | 1.6E-10 GMDS | 1 |
| rs72211825 | 6 | 36500140 | C | T | | 0.79 | -0.01 | 0.0011 | 4.0E-12 SRSF3 | 1 |
| rs2684249 | 6 | 122382511 | T | C | | 0.59 | -0.01 | 0.00092 | 1.2E-09 HSF2 | 1 |
| rs4518552 | 7 | 19277952 | A | T | | 0.66 | -0.01 | 0.00094 | 8.0E-10 TWISTNB | 1 |
| rs7786378 | 7 | 28934403 | A | C | | 0.56 | -0.01 | 0.00093 | 3.3E-09 CREB5 | 1 |
| rs29796392 | 8 | 8255319 | T | C | | 0.11 | -0.01 | 0.0014 | 1.2E-10 SGK223 | 1 |
| rs12543430 | 8 | 72278018 | T | C | | 0.39 | -0.01 | 0.00091 | 2.0E-09 EYA1 | 1 |
| rs78542921 | 9 | 18099832 | T | A | | 0.96 | 0.01 | 0.0024 | 8.1E-10 SH3GL2 | 1 |
| 10:21462896_GG | 10 | 21462896 | GGC | G | | 0.83 | -0.01 | 0.0041 | 2.4E-10 NEBL | 1 |
| rs17108260 | 10 | 94350713 | A | G | | 0.57 | -0.01 | 0.00091 | 2.6E-11 CYP26A1 | 1 |
| rs10805721 | 11 | 38934891 | G | A | | 0.73 | -0.01 | 0.00099 | 3.1E-08 DCDC5 | 1 |
| rs2753411 | 11 | 33465801 | A | T | | 0.48 | -0.0047 | 0.00066 | 2.1E-09 HIPK3 | 1 |
| rs2445575 | 11 | 86784437 | T | C | | 0.81 | 0.01 | 0.0011 | 1.1E-09 TMEM135 | 1 |
| rs11021221 | 11 | 95388854 | T | A | | 0.83 | 0.01 | 0.0011 | 2.3E-09 FAM76B | 1 |
| rs662298 | 12 | 76114872 | G | A | | 0.6 | 0.01 | 0.00093 | 2.0E-08 KAR1 | 1 |
| rs9631957 | 12 | 107170129 | T | C | | 0.64 | 0.01 | 0.00089 | 8.6E-12 RIC8B | 1 |
| rs18822502 | 13 | 109297305 | T | C | | 0.72 | 0.01 | 0.001 | 9.1E-13 MYO16 | 1 |

METHODS AND SYSTEMS FOR ASSESSING THE RISK OF GLAUCOMA

CROSS REFERENCE TO RELATED APPLICATIONS

This application is the § 371 U.S. National Stage of International Application No. PCT/AU2019/050635, filed Jun. 20, 2019, which was published in English under PCT Article 21(2), which in turn claims priority to Australian Provisional Patent Application No. 2018902206 filed on 20 Jun. 2018, the content of which is hereby incorporated by reference in its entirety.

FIELD

The present disclosure relates to methods and systems for assessing the risk of glaucoma in a subject, and methods of treating subjects for glaucoma based on the assessment of risk.

BACKGROUND

Glaucoma is the leading cause of irreversible blindness worldwide. In Western countries primary open angle glaucoma ("POAG") contributes the greatest disease burden, with a population prevalence of approximately 3% in people over 50 years of age. POAG is asymptomatic in the early stages, and currently approximately half of all cases in the community are undiagnosed.

Early detection of glaucoma is crucial as existing treatments are unable to reverse optic nerve damage, and late presentation is a major risk factor for advanced vision loss. Lowering intraocular pressure ("IOP") remains the major form of treatment.

Glaucoma is one of the most heritable of human diseases. However, to date screening strategies for glaucoma have lacked sensitivity and/or specificity, and have not been proven to be cost-effective.

Accordingly, there is a need for improved strategies for assessing the risk of glaucoma, so that patients with increased risk may be identified earlier and/or with more certainty than currently available, and suitable medical intervention can be utilised. Further, individuals assessed as being at reduced or low risk may be screened less frequently.

SUMMARY

The present disclosure relates to methods and systems for assessing the risk of glaucoma in a subject, and methods of treating subjects for glaucoma based on the assessment of risk.

Certain embodiments of the present disclosure provide a method of assessing the risk of primary open angle glaucoma in a subject, the method comprising:
determining a risk score for primary open angle glaucoma in the subject on the basis of the genetic content of the subject at a plurality of selected genetic loci or markers and thereby assessing the risk of primary open angle glaucoma in the subject, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a method of diagnosis or prognosis for primary open angle glaucoma, the method comprising:
identifying a subject as suffering from, or being susceptible to, primary open angle glaucoma on the basis of the genetic content of the subject at a plurality of selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a method of assessing the risk of primary open angle glaucoma in a subject, the method comprising:
determining the genetic content of the subject at a plurality of selected genetic loci or markers;
determining a risk score for primary open angle glaucoma in the subject on the basis of the genetic content of the subject at the plurality of selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and thereby assess the risk of primary open angle glaucoma.

Certain embodiments of the present disclosure provide a computer-readable medium encoded with programming instructions executable by a computer processor means to allow the computer processor means to:
process data associated with the genetic content of a subject at a plurality of selected genetic loci or markers and determine a risk score for the subject suffering from, or being susceptible to, primary open angle glaucoma, wherein the selected genetic loci or markers comprise one or more of (i) genetic loci or markers having an association with glaucoma, (ii) genetic loci or markers having an association with increased intraocular pressure, (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a computer processor means comprising a computer-readable medium encoded with programming instructions executable by a computer processor means to allow the computer processor means to:
process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a system for determining the risk of a primary open angle glaucoma in a subject, the system comprising a computer processor having a computer-readable medium encoded with programming instructions executable by the computer processor means to allow the computer processor means to:
  process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure and/or (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a method of assessing one or more of onset, progression, and severity of primary open angle glaucoma in a subject, the method comprising:
  determining one or more of onset, progression and severity of primary open angle glaucoma in the subject on the basis of the genetic content of the subject at a plurality of selected genetic loci or markers and thereby determine the onset, progression, severity and recurrence of the primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

Certain embodiments of the present disclosure provide a method of treating a subject suffering from, susceptible to, primary open angle glaucoma, the method comprising:
  identifying a subject at increased risk of primary open angle glaucoma using a risk score based on the genetic content of the subject at a plurality of selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and treating the subject so identified.

Certain embodiments of the present disclosure provide a method of identifying a genetic locus associated with an increased risk of primary open angle glaucoma, the method comprising:
  using a multi-trait model to test whether a candidate genetic locus or marker is associated with an increased risk of primary open angle glaucoma, the multi-trait model comprising combining genetic information on the candidate genetic locus or marker with genetic content from selected genetic loci or markers, wherein the selected genetic loci comprise one or more of (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and
  identifying the candidate genetic locus or marker as a locus associated with an increased risk of primary open angle glaucoma.

Certain embodiment of the present disclosure provide a method for producing a score for assessing the risk of primary open angle glaucoma, the method comprising:
  using a multi-trait model to combine genetic information on a plurality of selected genetic loci or markers having an association with primary open angle glaucoma, wherein the selected genetic loci or markers comprise one or more of (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and
  producing a score for assessing the risk of primary open angle glaucoma on the basis of results of the multi-trait model.

Certain embodiments of the present disclosure provide a method of treating a subject at increased risk of primary open angle glaucoma, the method comprising identifying a subject at increased risk of primary open angle glaucoma using a method as described herein and treating the subject so identified.

Certain embodiments of the present disclosure provide a method of assessing the risk of primary open angle glaucoma in a subject, the method comprising using a score produced by a method as described herein to assess the risk of primary open angle glaucoma in the subject.

Other embodiments are described herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 10 shows a table of VKBB VCDR GWAS loci.

FIG. 11 shows a table for MTAG four trait glaucoma—novel loci.

FIG. 12 shows a table for MTAG four trait glaucoma—all loci.

DETAILED DESCRIPTION

Figure 1:
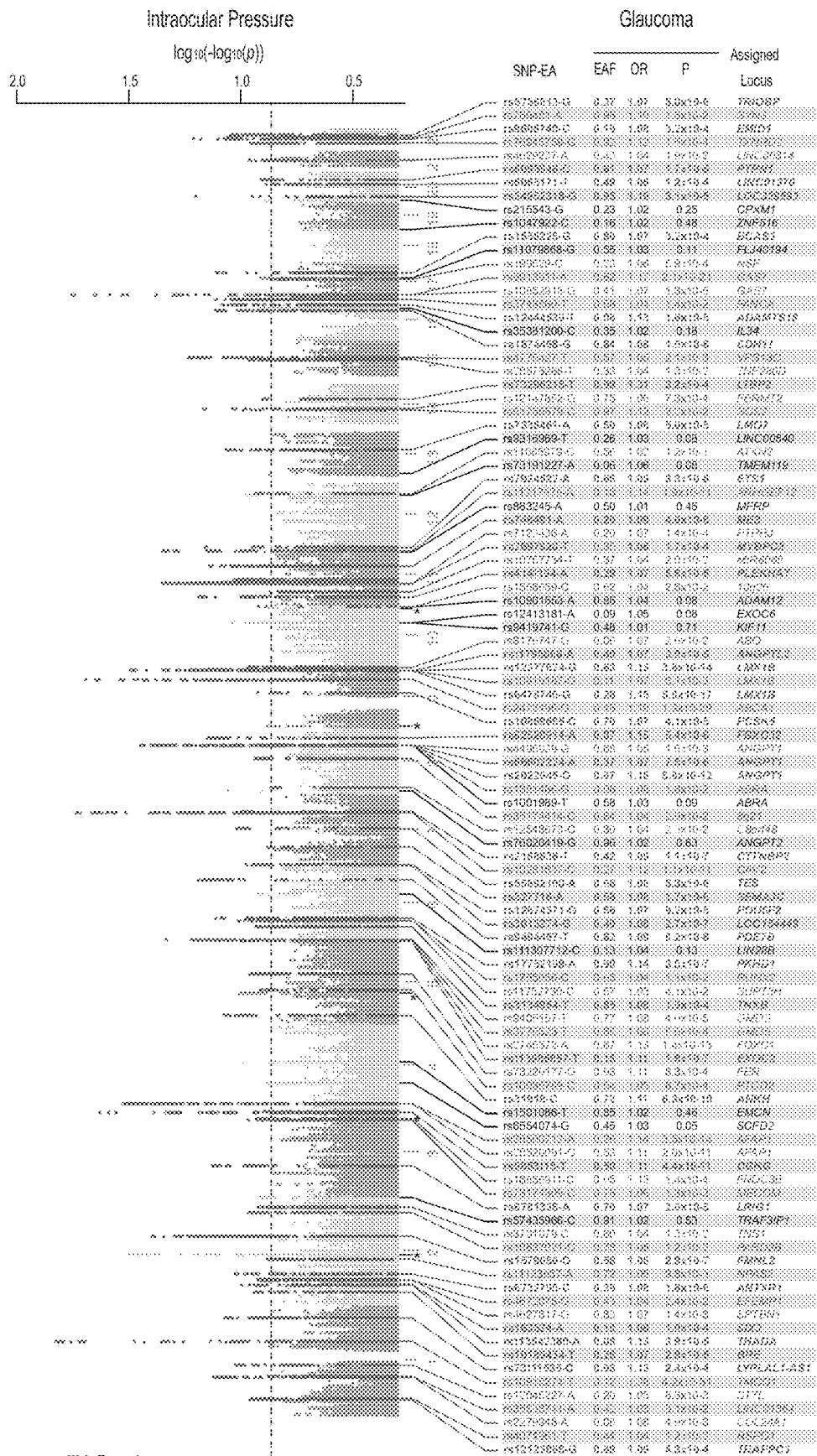
FIG. 1 shows a Manhattan plot displaying associations with intraocular pressure (IOP) in people of Northern European descent. The dashed line represents the threshold for genome-wide significance ($P<5\times10^{-8}$). Loci highlighted in blue are established regions known to be associated with primary open-angle glaucoma (POAG). The top SNP ("single nucleotide polymorphism") and its effect allele (SNP-EA) at each genome-wide significant locus is displayed with the corresponding effect allele frequency (EAF); odds ratio (OR); and p-value (P) for association in glaucoma cases (. The results are in black for SNPs with $P>0.05$ with glaucoma, red text for SNPs with $0.05<P<0.05/101$ (not significant following correction for multiple comparisons) and bold red text for SNPs with $P<0.05/101$ (significant following correction for multiple comparisons). *These loci were either reported central corneal thickness loci (AD-AMTS6) or more strongly associated with corneal hysteresis and were removed from subsequent analysis.

The present disclosure relates to methods and systems for assessing the risk of glaucoma in a subject, and methods of treating subjects for glaucoma based on the assessment of risk.

One or more embodiments of the present disclosure are directed to methods and systems that have one or more combinations of the following advantages: new and/or improved methods and systems for assessing the risk of primary open angle glaucoma; new and/or improved methods and systems for diagnosis or prognosis of primary open angle glaucoma; new and/or improved methods and system for screening for primary open angle glaucoma; new and/or improved methods and systems for diagnosis or prognosis of advanced glaucoma; new and/or improved methods and systems for diagnosis or prognosis of non-advanced glaucoma; new and/or improved methods and systems for identification of an earlier age of onset of primary open angle glaucoma; new and/or improved methods and system for identification of an earlier age of clinical diagnosis of glaucoma; new and/or improved methods and systems for assessing the risk of primary open angle glaucoma; new and/or improved methods and systems for assessing the likelihood of the need for surgery or treatment required for glaucoma; new and/or improved methods and systems for the identification of rapid progression of early stage glaucoma; new and/or improved methods and systems for assessing the likelihood of blindness from glaucoma; new and/or improved methods and systems for screening for primary open angle glaucoma in a population; new and/or improved methods and systems for assessing the risk of glaucoma, so that patients with increased risk may be identified earlier and/or with more certainty than currently available; new and/or improved methods and systems for identifying subjects for treatment for glaucoma; new and/or improved methods and systems to determine risk of primary open angle glaucoma before or after receiving clinical data; to address one or more problems, and/or to provide one or more advantages, or to provide a commercial alternative. Other advantages of certain embodiments of the present disclosure are also disclosed herein.

Certain embodiments of the present disclosure provide a method of assessing the risk of primary open angle glaucoma in a subject.

In certain embodiments, the present disclosure provides a method of assessing the risk of primary open angle glaucoma in a subject, the method comprising:
determining a risk score for the glaucoma in the subject on the basis of the genetic content of the subject at a plurality of selected genetic loci or markers and thereby assess the risk of primary open angle glaucoma in a subject, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma.

In certain embodiments, the selected genetic loci or markers comprise genetic loci or markers having an association with increased intraocular pressure.

In certain embodiments, the selected genetic loci or markers comprise genetic loci or markers having an association with an increased vertical cup to disk ratio.

In certain embodiments, the selected genetic loci or markers comprise genetic loci or markers having an association with an increased vertical cup to disk ratio corrected for optic nerve head size.

In certain embodiments, the selected genetic loci or markers comprise genetic loci or markers having an association with a multi-trait test of glaucoma, intraocular pressure and vertical cup to disc ratio.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

The phrase "genetic loci or markers having an association with" as used herein refers to a statistically significant correlation between a specific disease and/or a phenotype with a particular genetic variation. Genetic association may be interpreted as either a direct association where the genetic variant is a variant contributing to disease/phenotype or an indirect association in which the genetic variant is in linkage disequilibrium with a variant.

In this regard, it will be appreciated that a specific genetic locus or marker having an association with a disease/phenotype may be a genetic locus or marker identified as having an association with the disease/phenotype, or a specific identified genetic locus or marker which is found subsequently to have an association with the disease/phenotype.

The phrase "vertical cup to disk ratio" as used herein refers to an attribute of cup to disk ratio, and includes vertical cup to disk ratio and/or horizontal cup to disc ratio.

In certain embodiments, the methods of the present disclosure are used to determine the likelihood of a subject suffering from primary open angle glaucoma.

In certain embodiments, the subject is susceptible to primary open angle glaucoma. In certain embodiments, the subject is suffering from early stage primary open angle glaucoma. In certain embodiments, the subject has an increased risk of being susceptible to, or suffering from, primary open angle glaucoma. In certain embodiments, the subject has an increased likelihood of being susceptible to, or suffering from, early stage primary open angle glaucoma.

In certain embodiments, the subject has a high risk, a moderate risk, a normal risk or a low risk of being susceptible to, or suffering from, primary open angle glaucoma. In certain embodiments, the subject has a high risk of being susceptible to, or suffering from, primary open angle glaucoma. In certain embodiments, the subject has a moderate risk of being susceptible to, or suffering from, primary open angle glaucoma. In certain embodiments, the subject has a normal risk of being susceptible to, or suffering from, primary open angle glaucoma. In certain embodiments, the subject has a low risk of being susceptible to, or suffering from, primary open angle glaucoma.

In certain embodiments, the method comprises stratifying the risk score and assessing the risk based on the risk stratification. Methods for risk stratification are known in the art.

In certain embodiments, the subject is classified as having a high risk. In certain embodiments, the subject is classified as having a risk score in the top 5%, 10% or 20% of the profile score distribution. Other cut-offs are contemplated.

In certain embodiments, the subject is classified as having a low risk. In certain embodiments, the subject is classified as having a risk score in the bottom 5%, 10% or 20% of the profile score distribution. Other cut-offs are contemplated.

In certain embodiments, the subject is classified as having an intermediate risk. In certain embodiments, the subject is classified as having an intermediate risk score.

In certain embodiments, the method comprises determining a risk score for the glaucoma in the subject on the basis of the genetic content of the subject at one or more other genetic loci or markers.

In certain embodiments, the determining of the risk score does not comprise information relating to one or more clinical features.

In certain embodiments, the determining of the risk score further comprises information relating to one or more clinical features of the subject.

In certain embodiments, the determining of the risk score is undertaken before clinical data/features are available. In certain embodiments, the determining of the risk score is undertaken in conjunction with clinical data/features.

In certain embodiments, the one or more clinical features comprise one or more of n certain embodiments, the one or more clinical features comprising one or more of age, gender, family history of glaucoma, intraocular pressure, vertical cup to disc ratio, corrected vertical to cup disk ratio, data from optical coherence tomography of the optic nerve head, retinal nerve fibre layer, retinal ganglion cell layer, data from automated perimetry, ocular biomechanical factors (corneal thickness, corneal hysteresis, corneal rigidity), and systemic vascular factors (blood pressure, cerebrovascular disease, ischemic heart disease, migraine, Raynauds disease). Methods for assessing the aforementioned clinical features are known in the art.

For example, the one or more clinical features may comprise one or more age, gender, and intraocular pressure, optionally in conjunction with family history and/or retinal optical coherence tomography.

In certain embodiments, the risk score is indicative of one or more of the risk of primary open angle glaucoma, the risk of advanced glaucoma, the risk of non-advanced glaucoma, the age of onset of primary open angle glaucoma, the age of clinical diagnosis of glaucoma, the likelihood of surgery required for glaucoma; the risk of more rapid progression in early stage glaucoma, the risk of blindness from glaucoma, or the need for treatment for glaucoma.

In certain embodiments, an increased risk score is indicative of one or more of an increased risk of primary open angle glaucoma, an increased risk of advanced glaucoma, an increased risk of non-advanced glaucoma, an earlier agent of onset of primary open angle glaucoma, an earlier age of clinical diagnosis of glaucoma, an increased likelihood of surgery required for glaucoma, an increased risk of rapid progression in early stage glaucoma, an increased risk of blindness from glaucoma, or need for treatment for glaucoma.

In certain embodiments, the genetic content comprises one or more of genomic content, mitochondrial content, DNA content, and RNA content.

In certain embodiments, the genetic content comprises one or more of allelic information, gene information, coding region information, non-coding region information, DNA information, chromosomal information, genomic structural variations (e.g. deletions, duplications, inversions, translocation), mitochondrial RNA information (such as the expression of microRNAs), DNA methylation information, histone modification information and epigenetic information. Other types of genetic information are contemplated.

In certain embodiments, the genetic content comprises the presence and/or absence of one or more polymorphisms. In certain embodiments, the genetic content comprises the presence and/or absence of one or more single nucleotide polymorphisms.

The term "polymorphism" refers to a difference in DNA sequence between individuals. Examples of types of polymorphisms include single nucleotide polymorphisms, a mini-satellite length polymorphism, an insertion, a deletion, a frameshift, a base substitution, a duplication, an inversion, and a translocation.

In certain embodiments, the genetic content comprises information relating to one or more genetic loci or markers.

In certain embodiments, the genetic content comprises information relating to the presence and/or absence of one or more polymorphisms. In certain embodiments, the genetic content comprises information relating to the presence and/or absence of one or more single nucleotide polymorphisms (SNPs).

In this regard, the term "rs" used herein in conjunction with an accession number refers to an entry in dbSNP database for genetic variation hosted by the National Center for Biotechnology Information (NCBI) in collaboration with the National Human Genome Research Institute (NHGRI). The database contains a range of molecular variations including (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants.

In certain embodiments, the determining of the risk score comprises use of a multi-trait model combining information on the genetic content from the plurality of the selected genetic loci or markers. Multi-trait models are as described herein. Other methods for determining a risk score are contemplated In certain embodiments, the determining of the risk score comprises weighting of information of the genetic content from one or more of the selected genetic loci or markers. For example, weighting may be performed by using a linear combination of the number of risk alleles a subject has, with the weight applied for each marker based on the estimated log odds ratio for glaucoma. Methods for weighting are known in the art.

In certain embodiments, the genetic loci or markers having an association with glaucoma comprise genetic loci or markers having an association with advanced glaucoma disease.

In certain embodiments, the genetic loci or markers having an association with increased intraocular pressure comprise genetic loci or markers having an association with an intraocular pressure of greater than 21 mm Hg. In certain embodiments, genetic loci or markers having an association with an increased vertical cup to disk ratio comprise genetic loci or markers having a vertical cup to disk ratio of greater than 0.7.

In certain embodiments, the genetic loci or markers having an association with an increased vertical cup to disk ratio comprises genetic loci or markers having an association with an increased vertical cup to disk ratio corrected for optic nerve head size. Methods for correcting the vertical cup to disk ratio for optic nerve head size are known in the art.

In certain embodiments, the selected genetic loci or markers further comprise CDKN2B-AS and/or SIX6. In certain embodiments, the selected genetic loci further comprise markers rs2157719 within the CDKN2B-AS1 locus and/or rs8015152 within the SIX6 locus.

Examples of some genetic loci and associated markers associated with glaucoma are shown in Table 1.

TABLE 1

| Locus | SNP (Effect Allele) |
| --- | --- |
| LOC100147773, TMCO1 | rs7518099-T |
| CDKN2B-AS1 | rs944801-C |
| LOC105376196, ABCA1 | rs2472493-A |
| C14orf39, SIX6 | rs2093210-T |
| GAS7 | rs9913911-A |

TABLE 1-continued

| Locus | SNP (Effect Allele) |
| --- | --- |
| AFAP1 | rs28795989-c |
| LMX1B | rs945686-A |
| LOC102723944, GMDS | rs2745572-A |
| CADM2 | rs9284802-A |
| ARHGEF12 | rs58073046-A |
| THSD7A | rs12699251-A |
| ANGPT1 | rs10505100-A |
| CAV1, CAV2 | rs2024211-A |
| DGKG, LOC107986164, TBCCD1 | rs9853115-A |
| ANKH | rs61394862-T |
| LOC101929614, LOC105378153 | rs2935057-A |
| EXOC2 | rs2073006-T |
| MYOF, XRCC6P1 | rs61861119-A |
| TXNRD2 | rs8141433-A |
| BICC1 | rs4141671-T |
| MECOM | rs73174345-T |
| CTTNBP2, CFTR | rs1013278-C |
| ETS1 | rs7924522-A |
| LOC107986141, LOC107986142 | rs11710139-A |

In certain embodiments, the genetic loci or markers having an association with glaucoma comprise one or more of the selected genetic loci or markers shown in Table 1. Combinations of one or more of the above genetic loci or markers are contemplated.

In certain embodiments, the genetic loci or markers having an association with glaucoma comprise 90% or more, 80% or more, 70% or more, 60% or more, 50% or more, 40% or more, 30% or more, 20% or more, or 10% or more of the selected genetic loci shown in Table 1.

In certain embodiments, the genetic loci or markers having an association with glaucoma comprise one or more of the selected genetic loci shown in Table 2.

TABLE 2

| Locus |
| --- |
| LOC100147773, TMCO1 |
| CDKN2B-AS1 |
| LOC105376196, ABCA1 |
| C14orf39, SIX6 |
| GAS7 |
| AFAP1 |
| LMX1B |
| LOC102723944, GMDS |
| CADM2 |
| ARHGEF12 |
| THSD7A |
| ANGPT1 |
| CAV1, CAV2 |
| DGKG, LOC107986164, TBCCD1 |
| ANKH |
| LOC101929614, LOC105378153 |
| EXOC2 |
| MYOF, XRCC6P1 |
| TXNRD2 |
| BICC1 |
| MECOM |
| CTTNBP2, CFTR |
| ETS1 |
| LOC107986141, LOC107986142 |

Combinations of one or more of the above genetic loci are contemplated.

In certain embodiments, the genetic loci or markers having an association with glaucoma comprise 90% or more, 80% or more, 70% or more, 60% or more, 50% or more, 40% or more, 30% or more, 20% or more, 10% or more, or 5% or more of the selected genetic loci shown in Table 2.

In certain embodiments, the genetic loci or markers having an association with glaucoma comprise one or more of the following selected genetic markers shown in Table 3.

TABLE 3

| SNP (Effect Allele) |
|---|
| rs7518099-T |
| rs944801-C |
| rs2472493-A |
| rs2093210-T |
| rs9913911-A |
| rs28795989-c |
| rs945686-A |
| rs2745572-A |
| rs9284802-A |
| rs58073046-A |
| rs12699251-A |
| rs10505100-A |
| rs2024211-A |
| rs9853115-A |
| rs61394862-T |
| rs2935057-A |
| rs2073006-T |
| rs61861119-A |
| rs8141433-A |
| rs4141671-T |
| rs73174345-T |
| rs1013278-C |
| rs7924522-A |
| rs11710139-A |

Combinations of one or more of the above genetic markers (or a variant of the SNP at the equivalent position) are contemplated.

In certain embodiments, the genetic markers having an association with glaucoma comprise 90% or more, 80% or more, 70% or more, 60% or more, 50% or more, 40% or more, 30% or more, 20% or more, 10% or more, or 5% or more of the selected genetic markers shown in Table 3.

Examples of some genetic loci or markers and associated markers associated with increased intraocular pressure are shown in Table 4.

TABLE 4

| Locus | SNP (Effect Allele) |
|---|---|
| TRIOBP | rs5756813-G |
| SYN3 | rs756481-A |
| EMID1 | rs9608740-C |
| TXNRD2 | rs76945759-G |
| LINC00314 | rs4629237-A |
| PTPN1 | rs6095946-C |
| LINC01370 | rs6065171-T |
| LOC339593 | rs34952318-G |
| CPXM1 | rs215543-G |
| ZNF516 | rs1047922-C |
| BCAS3 | rs1558225-G |
| FLJ40194 | rs11079868-G |
| NSF | rs199529-C |
| GAS7 | rs9913911-A |
| GAS7 | rs10852918-G |
| FANCA | rs3743860-T |
| ADAMTS18 | rs12444539-T |
| IL34 | rs35381200-C |
| CDH11 | rs1874458-G |
| VPS13C | rs4775427-T |
| ZNF280D | rs28575268-T |
| LTBP2 | rs73296215-T |
| FERMT2 | rs12147852-A |
| SOS2 | rs61755579-C |
| LMO7 | rs7338461-A |
| LINC00540 | rs9316969-T |
| ATXN2 | rs11065979-C |
| TMEM119 | rs73191227-A |
| ETS1 | rs7924522-A |
| ARHGEF12 | rs11217878-A |
| MFRP | rs883245-A |
| ME3 | rs746491-A |
| PTPRJ | rs7123436-A |
| MYBPC3 | rs2697920-T |
| MIR8068 | rs10767734-T |
| PLEKHA7 | rs4141194-A |
| 10q26 | rs1556659-C |
| ADAM12 | rs10901553-A |
| EXOC6 | rs12413181-A |
| KIF11 | rs9419741-G |
| ABO | rs8176747-G |
| ANGPTL2 | rs11795066-A |
| LMX1B | rs12377624-G |
| LMX1B | rs10819187-G |
| LMX1B | rs6478746-G |
| ABCA1 | rs2472496-G |
| PCSK5 | rs10869665-C |
| FBXO32 | rs62520914-A |
| ANGPT1 | rs4496939-G |
| ANGPT1 | rs66602224-A |
| ANGPT1 | rs2022945-G |
| ABRA | rs1381486-G |
| ABRA | rs1001989-T |
| 8q21 | rs35174414-C |
| C8orf48 | rs12548673-C |
| ANGPT2 | rs76020419-G |
| CTTNBP2 | rs2188836-T |
| CAV2 | rs10281637-C |
| TES | rs55892100-A |
| SEMA3C | rs327716-A |
| POU6F2 | rs12674371-G |
| LOC154449 | rs3013274-G |
| PDE7B | rs9494457-T |
| LIN28B | rs111307712-C |
| PKHD1 | rs17752199-A |
| RUNX2 | rs1755056-C |
| SUPT3H | rs11752730-C |
| TNXB | rs3134954-T |
| GMDS | rs9405157-T |
| GMDS | rs3778523-T |
| FOXC1 | rs2745572-A |
| EXOC2 | rs113985657-T |
| FER | rs73220177-G |
| PTCD2 | rs10036789-C |
| ANKH | rs31918-C |
| EMCN | rs1501086-T |
| SCFD2 | rs6554074-G |
| AFAP1 | rs28500712-A |
| AFAP1 | rs28520091-C |
| DGKG | rs9853115-T |
| FNDC3B | rs16856911-C |
| MECOM | rs73174309-C |
| LRIG1 | rs6781336-A |
| TRAF3IP1 | rs57435966-C |
| TNS1 | rs3791979-C |
| PARD3B | rs16837021-C |
| FMNL2 | rs1579050-G |
| NPAS2 | rs11123857-A |
| ANTXR1 | rs6732795-C |
| EFEMP1 | rs4672075-G |
| SPTBN1 | rs4627617-G |
| SIX3 | rs163524-A |
| THADA | rs113542380-A |
| BRE | rs10189434-T |
| LYPLAL1-AS1 | rs73111535-C |
| TMCO1 | rs10918274-T |
| ST7L | rs12045227-A |
| LINC01364 | rs35638741-A |
| COL24A1 | rs2279948-A |
| RSPO1 | rs4074961-T |
| TRAPPC3 | rs12123086-G |

In certain embodiments, the genetic loci or markers having an association with increased intraocular pressure comprise one or more of the selected genetic loci or markers shown in Table 4.

In certain embodiments, the genetic loci or markers having an association with increased intraocular pressure comprise 90% or more, 80% or more, 70% or more, 60% or more, 50% or more, 40% or more, 30% or more, 20% or more, 10% or more, 9% or more, 8% or more, 7% or more, 6% or more, or 5% or more of the selected genetic loci shown in Table 4.

In certain embodiments, the genetic loci or markers having an association with increased intraocular pressure comprise greater than 7% of the genetic loci or markers having an association with increased intraocular pressure shown in Table 4.

In certain embodiments, the genetic loci or markers having an association with increased ocular pressure comprise one or more of the following selected genetic loci shown in Table 5.

TABLE 5

| Locus |
| --- |
| TRIOBP |
| SYN3 |
| EMID1 |
| TXNRD2 |
| LINC00314 |
| PTPN1 |
| LINC01370 |
| LOC339593 |
| CPXM1 |
| ZNF516 |
| BCAS3 |
| FLJ40194 |
| NSF |
| GAS7 |
| FANCA |
| ADAMTS18 |
| IL34 |
| CDH11 |
| VPS13C |
| ZNF280D |
| LTBP2 |
| FERMT2 |
| SOS2 |
| LMO7 |
| LINC00540 |
| ATXN2 |
| TMEM119 |
| ETS1 |
| ARHGEF12 |
| MFRP |
| ME3 |
| PTPRJ |
| MYBPC3 |
| MIR8068 |
| PLEKHA7 |
| 10q26 |
| ADAM12 |
| EXOC6 |
| KIF11 |
| ABO |
| ANGPTL2 |
| LMX1B |
| ABCA1 |
| PCSK5 |
| FBXO32 |
| ANGPT1 |
| ABRA |
| 8q21 |
| C8orf48 |
| ANGPT2 |
| CTTNBP2 |
| CAV2 |

TABLE 5-continued

| Locus |
| --- |
| TES |
| SEMA3C |
| POU6F2 |
| LOC154449 |
| PDE7B |
| LIN28B |
| PKHD1 |
| RUNX2 |
| SUPT3H |
| TNXB |
| GMDS |
| FOXC1 |
| EXOC2 |
| FER |
| PTCD2 |
| ANKH |
| EMCN |
| SCFD2 |
| AFAP1 |
| DGKG |
| FNDC3B |
| MECOM |
| LRIG1 |
| TRAF3IP1 |
| TNS1 |
| PARD3B |
| FMNL2 |
| NPAS2 |
| ANTXR1 |
| EFEMP1 |
| SPTBN1 |
| SIX3 |
| THADA |
| BRE |
| LYPLAL1-AS1 |
| TMCO1 |
| ST7L |
| LINC01364 |
| COL24A1 |
| RSPO1 |
| TRAPPC3 |

Combinations of one or more of the above genetic loci are contemplated.

In certain embodiments, the genetic loci or markers having an association with increased intraocular pressure comprise 90% or more, 80% or more, 70% or more, 60% or more, 50% or more, 40% or more, 30% or more, 20% or more, 10% or more, 9% or more, 8% or more, 7% or more, 6% or more, or 5% or more of the selected genetic loci shown in Table 5.

In certain embodiments, the genetic loci or markers having an association with an increased ocular pressure comprise one or more of the selected genetic markers (or a variant of the marker with another nucleotide at the equivalent position) shown in Table 6.

TABLE 6

| SNP (Effect Allele) |
| --- |
| rs5756813-G |
| rs756481-A |
| rs9608740-C |
| rs76945759-G |
| rs4629237-A |
| rs6095946-C |
| rs6065171-T |
| rs34952318-G |
| rs215543-G |
| rs1047922-C |
| rs1558225-G |
| rs11079868-G |

TABLE 6-continued

| SNP (Effect Allele) |
|---|
| rs199529-C |
| rs9913911-A |
| rs10852918-G |
| rs3743860-T |
| rs12444539-T |
| rs35381200-C |
| rs1874458-G |
| rs4775427-T |
| rs28575268-T |
| rs73296215-T |
| rs12147852-G |
| rs61755579-C |
| rs7338461-A |
| rs9316969-T |
| rs11065979-C |
| rs73191227-A |
| rs7924522-A |
| rs11217878-A |
| rs883245-A |
| rs746491-A |
| rs7123436-A |
| rs2697920-T |
| rs10767734-T |
| rs4141194-A |
| rs1556659-C |
| rs10901553-A |
| rs12413181-A |
| rs9419741-G |
| rs8176747-G |
| rs11795066-A |
| rs12377624-G |
| rs10819187-G |
| rs6478746-G |
| rs2472496-G |
| rs10869665-C |
| rs62520914-A |
| rs4496939-G |
| rs66602224-A |
| rs2022945-G |
| rs1381486-G |
| rs1001989-T |
| rs35174414-C |
| rs12548673-C |
| rs76020470-G |
| rs2188836-T |
| rs10281637-C |
| rs55892100-A |
| rs327716-A |
| rs12674371-G |
| rs3013274-G |
| rs9494457-T |
| rs111307712-C |
| rs17752199-A |
| rs1755056-C |
| rs11752730-C |
| rs3134954-T |
| rs9405157-T |
| rs3778523-T |
| rs2745572-A |
| rs113985657-T |
| rs73220177-G |
| rs10036789-C |
| rs31918-C |
| rs1501086-T |
| rs6574074-G |
| rs28500712-A |
| rs28520091-C |
| rs9853115-T |
| rs16856911-C |
| rs73174309-C |
| rs6781336-A |
| rs57435966-C |
| rs3791979-C |
| rs16837021-C |
| rs1579050-G |
| rs11123857-A |
| rs6732795-C |
| rs4672075-G |

TABLE 6-continued

| SNP (Effect Allele) |
|---|
| rs4627617-G |
| rs163524-A |
| rs113542380-A |
| rs10189434-T |
| rs73111535-C |
| rs10918274-T |
| rs12045227-A |
| rs35638741-A |
| rs2279948-A |
| rs4074961-T |
| rs12123086-G |

Combinations of one or more of the above genetic markers (or a variant of the SNP at the equivalent position) are contemplated.

In certain embodiments, the genetic markers having an association with increased intraocular pressure comprise 90% or more, 80% or more, 70% or more, 60% or more, 50% or more, 40% or more, 30% or more, 20% or more, 10% or more, 9% or more, 8% or more, 7% or more, 6% or more, or 5% or more of the selected genetic markers shown in Table 6.

Examples of some genetic loci or markers associated with vertical cup to disk ratio are shown in Table 7.

TABLE 7

| Locus | SNP (Effect Allele) |
|---|---|
| PRDM16 | rs12024620C |
| WLS | rs34151819C |
| TGFB2 | rs1417488C |
| ZNF678 | rs77271542A |
| EFEMP1 | rs376096585C |
| ACOXL | rs2880192A |
| FMNL2 | rs1579050A |
| RARB | rs4858682C |
| TRIM71 | rs34010125T |
| C3orf38 | 3: 88379094AT |
| MIR548G | rs4928176G |
| ABI3BP | rs9827694G |
| AMOTL2 | rs143351962C |
| GSX2 | rs2162137C |
| PDGFRA | rs565335773G |
| ANKRD55 | rs158653G |
| LOC102467147 | rs30372T |
| ADAMTS19 | rs11749004T |
| VDAC1 | 5: 133393380GA |
| GMDS | rs2761235C |
| SRSF3 | rs12211825C |
| HSF2 | rs2684249T |
| TWISTNB | rs4518562A |
| CREB5 | rs7805378A |
| SGK223 | rs2976932T |
| EYA1 | rs12543430T |
| SH3GL2 | rs78542921T |
| NEBL | 10: 21462896GGC |
| CYP26A1 | rs17108260A |
| DCDC5 | rs10835721G |
| HIPK3 | rs2753411A |
| TMEM135 | rs2445575T |
| FAM76B | rs11021221T |
| KRR1 | rs6582298G |
| RIC8B | rs9651957T |
| MYO16 | rs10162202T |
| COL4A1 | 13: 110778747CCTTTT |
| PRMT5 | rs4982708G |
| FLRT2 | rs984586G |
| LOXL1 | rs893817G |
| FENDRR | rs35526343C |
| PPP1R9B | rs847688T |
| BCAS3 | rs2204928C |
| LPPR3 | rs146055611C |
| THEG5 | rs8102936G |

TABLE 7-continued

| Locus | SNP (Effect Allele) |
|---|---|
| CASC20 | rs6140010A |
| MAPRE1 | rs3831804T |
| TRIOBP | rs71324877G |
| DHRS3 | rs6690264A |
| RPE65 | rs3125918A |
| CDC7-TGFBR3 | rs4658101A |
| MIR548G | rs6804624T |
| PDZD2 | rs72759609T |
| DUSP1 | rs34471628A |
| RREB1 | rs4960297C |
| DGKB | rs10260511C |
| CDKN2B-AS1 | rs7039467A |
| CDKN2B-AS1 | rs7866783A |
| ATOH7 | rs7916697A |
| HSPA12A | rs11197820G |
| SSSCA1-AS1 | rs1346A |
| ADAMTS8 | rs4936099C |
| TMTC2 | rs61952219G |
| TMTC2 | 12: 83973565TTCTC |
| ZNF664-FAM101A | rs4765353-G |
| DCLK1 | rs9546383-T |
| DDHD1 | rs2251171-G |
| PPM1A | rs10162287-C |
| ASB7 | rs148139847-C |
| SALL1 | rs373836950-C |
| SALL1 | rs8053277-T |
| SALL1 | rs2720429-G |
| CHEK2 | rs7287609-C |
| CHEK2 | rs6005840-A |
| HORMAD2 | rs713875-C |
| CARD10 | rs113605227-A |

In certain embodiments, the genetic loci or markers having an association with an increased vertical cup to disk ration g comprise one or more of the selected genetic loci shown in Table 7.

In certain embodiments, the genetic loci or markers having an association with an increased vertical cup to disc ratio comprise 90% or more, 80% or more, 70% or more, 60% or more, 50% or more, 40% or more, 30% or more, 20% or more, 19% or more, 18% or more, 17% or more, 16% or more, 15% or more, 14% or more, 13% or more, 12% or more, 11% or more, 10% or more, 9% or more, 8% or more, 7% or more, 6% or more, or 5% or more of the selected genetic loci shown in Table 7.

In certain embodiments, the genetic loci or markers having an association with an increased vertical cup to disc ratio comprise greater than 16% of the genetic loci or markers having an association with an increased vertical cup to disc ratio as shown in Table 7.

In certain embodiments, the genetic loci or markers having an association with an increased vertical cup to disk ratio size comprise one or more of the following selected genetic loci shown in Table 8.

TABLE 8

| Locus |
|---|
| PRDM16 |
| WLS |
| TGFB2 |
| ZNF678 |
| EFEMP1 |
| ACOXL |
| FMNL2 |
| RARB |
| TRIM71 |
| C3orf38 |
| MIR548G |
| ABI3BP |

TABLE 8-continued

| Locus |
|---|
| AMOTL2 |
| GSX2 |
| PDGFRA |
| ANKRD55 |
| LOC102467147 |
| ADAMTS19 |
| VDAC1 |
| GMDS |
| SRSF3 |
| HSF2 |
| TWISTNB |
| CREB5 |
| SGK223 |
| EYA1 |
| SH3GL2 |
| NEBL |
| CYP26A1 |
| DCDC5 |
| HIPK3 |
| TMEM135 |
| FAM76B |
| KRR1 |
| RIC8B |
| MYO16 |
| COL4A1 |
| PRMT5 |
| FLRT2 |
| LOXL1 |
| FENDRR |
| PPP1R9B |
| BCAS3 |
| LPPR3 |
| THEG5 |
| CASC20 |
| MAPRE1 |
| TRIOBP |
| DHRS3 |
| RPE65 |
| CDC7-TGFBR3 |
| MIR548G |
| PDZD2 |
| DUSP1 |
| RREB1 |
| DGKB |
| CDKN2B-AS1 |
| ATOH7 |
| HSPA12A |
| SSSCA1-AS1 |
| ADAMTS8 |
| TMTC2 |
| ZNF664-FAM101A |
| DCLK1 |
| DDHD1 |
| PPM1A |
| ASB7 |
| SALL1 |
| CHEK2 |
| CHEK2 |
| HORMAD2 |
| CARD10 |

Combinations of one or more of the above genetic loci are contemplated.

In certain embodiments, the genetic loci or markers having an association with increased intraocular pressure comprise 90% or more, 80% or more, 70% or more, 60% or more, 50% or more, 40% or more, 30% or more, 20% or more, 10% or more, 9% or more, 8% or more, 7% or more, 6% or more, or 5% or more of the selected genetic loci shown in Table 8.

In certain embodiments, the genetic loci or markers having an association with an increased vertical cup to disk ratio size comprise one or more of the selected genetic markers shown in Table 9.

TABLE 9

| SNP (Effect Allele) |
| --- |
| rs12024620C |
| rs34151819C |
| rs1417488C |
| rs77271542A |
| rs376096585C |
| rs2880192A |
| rs1579050A |
| rs4858682C |
| rs34010125T |
| 3: 88379094AT |
| rs4928176G |
| rs9827694G |
| rs143351962C |
| rs2162137C |
| rs565335773G |
| rs158653G |
| rs30372T |
| rs11749004T |
| 5: 133393380GA |
| rs2761235C |
| rs12211825C |
| rs2684249T |
| rs4518562A |
| rs7805378A |
| rs2976932T |
| rs12543430T |
| rs78542921T |
| 10: 21462896GGC |
| rs17108260A |
| rs10835721G |
| rs2753411A |
| rs2445575T |
| rs11021221T |
| rs6582298G |
| rs9651957T |
| rs10162202T |
| 13: 110778747CCTTTT |
| rs4982708G |
| rs984586G |
| rs893817G |
| rs35526343C |
| rs847688T |
| rs2204928C |
| rs146055611C |
| rs8102936G |
| rs6140010A |

TABLE 9-continued

| SNP (Effect Allele) |
| --- |
| rs3831804T |
| rs71324877G |
| rs6690264A |
| rs3125918A |
| rs4658101A |
| rs6804624T |
| rs72759609T |
| rs34471628A |
| rs4960297C |
| rs10260511C |
| rs7039467A |
| rs7866783A |
| rs7916697A |
| rs11197820G |
| rs1346A |
| rs4936099C |
| rs61952219G |
| 12: 83973565TTCTC |
| rs4765353-G |
| rs9546383-T |
| rs2251171-G |
| rs10162287-C |
| rs148139847-C |
| rs373836950-C |
| rs8053277-T |
| rs2720429-G |
| rs7287609-C |
| rs6005840-A |
| rs713875-C |
| rs113605227-A |

Combinations of one or more of the above genetic markers (or a variant of the SNP at the equivalent position) are contemplated.

In certain embodiments, the genetic markers having an association with increased intraocular pressure comprise 90% or more, 80% or more, 70% or more, 60% or more, 50% or more, 40% or more, 30% or more, 20% or more, 10% or more, 9% or more, 8% or more, 7% or more, 6% or more, or 5% or more of the selected genetic markers shown in Table 9.

Table 10 contains loci obtained from the multivariate test described herein, together with their significance.

TABLE 10

| Locus | SNP | EA | P-multivariate | P-Glaucoma | P-IOP | P-VCDR |
| --- | --- | --- | --- | --- | --- | --- |
| COL8A2 | rs274760 | C | 2.00E−08 | 7.20E−05 | 1.10E−09 | 0.22 |
| RSPO1 | rs10796912 | G | 1.10E−08 | 6.70E−03 | 1.30E−09 | 0.42 |
| COL24A1 | rs12068500 | G | 7.30E−13 | 9.70E−03 | 5.50E−14 | 1.50E−03 |
| LOC100505768 | rs12139208 | T | 2.20E−12 | 3.50E−07 | 1.40E−08 | 0.34 |
| HSP90B3P | rs4658101 | A | 1.20E−13 | 0.04 | 0.04 | 8.90E−35 |
| ST7L | rs12045227 | G | 5.30E−10 | 6.90E−03 | 1.60E−11 | 2.00E−03 |
| TMCO1 | rs10918274 | T | 5.60E−92 | 2.50E−55 | 3.70E−67 | 2.40E−06 |
| LOC643723 | rs73111535 | C | 3.40E−13 | 9.70E−05 | 1.20E−12 | 0.56 |
| BRE | rs6741499 | C | 3.80E−12 | 1.70E−05 | 9.90E−09 | 5.10E−05 |
| THADA | rs113542380 | G | 9.70E−12 | 2.00E−05 | 9.50E−11 | 0.05 |
| SIX3 | rs163524 | C | 5.70E−09 | 5.00E−05 | 2.10E−08 | 0.54 |
| SPTBN1 | rs74259971 | T | 4.00E−10 | 5.10E−04 | 8.40E−09 | 0.89 |
| PNPT1 | rs1084524 | G | 2.10E−09 | 4.20E−06 | 2.40E−09 | 0.07 |
| MIR4778 | rs13009933 | C | 1.30E−10 | 2.90E−05 | 4.90E−07 | 9.80E−05 |
| ANTXR1 | rs6732795 | A | 7.20E−12 | 6.80E−07 | 1.80E−11 | 0.32 |
| NPAS2 | rs56405342 | C | 7.20E−09 | 0.02 | 5.50E−08 | 0.02 |
| FMNL2 | rs1579050 | A | 7.50E−26 | 1.10E−07 | 3.90E−26 | 4.10E−09 |
| PARD3B | rs62172701 | A | 2.70E−08 | 4.20E−03 | 1.10E−09 | 0.77 |
| MIR4776-1 | rs62188040 | C | 2.10E−09 | 2.90E−05 | 2.60E−05 | 0.87 |
| RARB | rs1286771 | T | 4.90E−11 | 2.00E−05 | 8.00E−08 | 9.80E−03 |
| SEMA3F | rs2526385 | T | 1.10E−09 | 8.00E−08 | 1.50E−07 | 0.05 |
| KBTBD8 | rs1867409 | G | 1.10E−16 | 8.10E−06 | 9.20E−15 | 2.40E−05 |
| CADM2 | rs66500121 | A | 2.60E−13 | 4.20E−13 | 1.70E−05 | 0.03 |
| KALRN | rs893830 | G | 7.80E−09 | 1.40E−04 | 6.50E−07 | 0.41 |
| TSC22D2 | rs11710845 | C | 2.70E−09 | 2.00E−08 | 1.00E−05 | 0.98 |

TABLE 10-continued

| Locus | SNP | EA | P-multivariate | P-Glaucoma | P-IOP | P-VCDR |
|---|---|---|---|---|---|---|
| MECOM | rs9816799 | T | 4.50E−11 | 6.10E−06 | 7.70E−06 | 2.50E−04 |
| LOC253573 | rs9853115 | T | 1.10E−39 | 6.20E−12 | 1.80E−44 | 0.02 |
| LPP | rs4420855 | A | 3.80E−10 | 5.50E−07 | 3.90E−08 | 0.75 |
| AFAP1 | rs28795989 | A | 5.80E−42 | 4.90E−22 | 4.10E−33 | 1.30E−03 |
| AFAP1 | rs6838291 | C | 2.20E−36 | 6.00E−17 | 4.80E−30 | 9.10E−03 |
| VEGFC | rs447324 | A | 3.40E−09 | 4.20E−04 | 6.40E−06 | 0.67 |
| ANKH | rs76325372 | A | 4.30E−18 | 9.90E−11 | 2.50E−12 | 2.90E−04 |
| PTCD2 | rs4703855 | C | 6.10E−11 | 1.10E−04 | 2.70E−07 | 0.05 |
| FER | rs73220190 | T | 1.90E−09 | 5.70E−04 | 4.40E−09 | 0.32 |
| CDC25C | rs11567976 | C | 1.70E−08 | 1.70E−03 | 4.50E−07 | 0.02 |
| JAKMIP2 | rs1347141 | A | 2.90E−08 | 7.70E−03 | 4.00E−05 | 0.02 |
| EXOC2 | rs57111852 | G | 6.20E−22 | 8.70E−10 | 5.20E−11 | 5.10E−06 |
| FOXC1 | rs2745572 | A | 1.20E−30 | 1.50E−14 | 3.60E−22 | 3.70E−04 |
| GMDS | rs722585 | G | 1.10E−11 | 1.00E−03 | 7.30E−12 | 3.30E−03 |
| GMDS | rs6914444 | T | 4.10E−21 | 2.80E−06 | 2.30E−06 | 2.10E−10 |
| SUPT3H | rs2145826 | G | 1.30E−11 | 1.80E−04 | 6.60E−08 | 0.03 |
| PKHD1 | rs2439042 | T | 7.60E−16 | 1.00E−05 | 1.50E−16 | 0.14 |
| PDE7B | rs9494457 | T | 6.90E−17 | 2.70E−08 | 2.30E−16 | 0.05 |
| TMEM181 | rs4709210 | T | 1.30E−09 | 4.60E−06 | 1.30E−06 | 0.25 |
| LOC154449 | rs2935072 | C | 2.40E−14 | 2.30E−10 | 6.10E−09 | 0.35 |
| THSD7A | rs2526101 | A | 1.30E−10 | 2.90E−12 | 6.50E−06 | 0.54 |
| BBS9 | rs1362227 | A | 3.20E−09 | 2.10E−04 | 8.80E−08 | 0.47 |
| POU6F2 | rs10435033 | G | 8.70E−09 | 1.10E−04 | 5.40E−06 | 0.06 |
| SEMA3C | rs327712 | C | 1.70E−14 | 3.70E−07 | 4.40E−11 | 0.22 |
| RELN | rs7799028 | G | 1.40E−08 | 2.80E−03 | 1.30E−05 | 1.30E−03 |
| TES | rs2896175 | A | 1.70E−18 | 1.40E−06 | 3.20E−17 | 0.06 |
| CAV2 | rs59454355 | C | 4.40E−49 | 1.90E−10 | 6.70E−57 | 3.80E−04 |
| CTTNBP2 | rs2188836 | C | 5.80E−15 | 3.00E−08 | 1.30E−10 | 0.23 |
| PRKAG2 | rs4128399 | T | 1.50E−09 | 4.20E−08 | 8.10E−07 | 0.27 |
| PKIA | rs4412362 | C | 9.50E−10 | 3.50E−03 | 6.40E−09 | 0.17 |
| ABRA | rs2881425 | A | 1.60E−09 | 0.17 | 2.00E−15 | 0.37 |
| ANGPT1 | rs2022945 | A | 1.10E−29 | 7.10E−13 | 2.50E−30 | 0.59 |
| ANGPT1 | rs1283696 | T | 2.70E−11 | 3.50E−05 | 9.30E−11 | 0.53 |
| FBXO32 | rs17339357 | T | 9.20E−14 | 4.50E−07 | 7.20E−15 | 0.82 |
| CDKN2B-AS1 | rs944801 | G | 2.00E−38 | 5.20E−38 | 0.21 | 7.60E−64 |
| PCSK5 | rs10869665 | C | 2.70E−11 | 1.70E−05 | 9.90E−09 | 0.13 |
| ABCA1 | rs2472493 | G | 7.80E−59 | 4.90E−32 | 3.00E−51 | 4.10E−03 |
| LMX1B | rs2275241 | G | 3.20E−40 | 3.00E−15 | 1.90E−32 | 2.20E−05 |
| RALGPS1 | rs62580791 | A | 1.10E−12 | 3.20E−04 | 1.90E−14 | 0.84 |
| ABO | rs12216891 | C | 6.70E−14 | 7.20E−03 | 2.20E−09 | 5.70E−07 |
| ARHGAP12 | rs11008626 | T | 6.60E−09 | 3.90E−04 | 2.10E−06 | 0.75 |
| BICC1 | rs7089636 | T | 9.80E−14 | 1.20E−07 | 8.50E−06 | 5.00E−05 |
| KCNMA1 | rs1616405 | A | 4.00E−08 | 4.70E−04 | 9.20E−06 | 0.3 |
| CYP26A1 | rs12778014 | G | 1.00E−08 | 2.00E−06 | 0.1 | 4.70E−11 |
| PLCE1 | rs2274224 | G | 2.70E−13 | 2.10E−08 | 3.10E−05 | 1.60E−04 |
| PLEKHA7 | rs4141194 | C | 5.20E−15 | 2.20E−05 | 9.90E−16 | 0.12 |
| METTL15 | rs12280392 | T | 6.50E−09 | 1.10E−03 | 1.90E−07 | 0.01 |
| PTPRJ | rs56319620 | C | 4.50E−21 | 5.20E−05 | 6.10E−23 | 3.90E−03 |
| OR4C46 | rs4434990 | G | 2.80E−10 | 5.40E−05 | 2.00E−11 | 0.76 |
| OR4A16 | rs11229165 | T | 4.10E−10 | 3.60E−05 | 2.40E−11 | 0.77 |
| MALAT1 | rs4102217 | G | 7.80E−16 | 5.60E−07 | 1.90E−03 | 1.30E−13 |
| ME3 | rs11234741 | A | 2.70E−16 | 7.80E−07 | 2.20E−14 | 0.18 |
| TYR | rs1126809 | G | 1.10E−08 | 1.50E−06 | 2.40E−04 | 8.20E−04 |
| ARHGEF12 | rs58073046 | A | 1.10E−21 | 4.00E−13 | 6.50E−23 | 0.47 |
| ETS1 | rs7924522 | C | 6.90E−17 | 1.00E−08 | 3.10E−15 | 0.07 |
| ADAMTS8 | rs4936100 | A | 1.50E−09 | 2.60E−06 | 1.20E−03 | 5.70E−03 |
| TMTC2 | rs324762 | A | 2.90E−12 | 4.00E−04 | 0.52 | 1.20E−57 |
| SH2B3 | rs3184504 | T | 5.60E−09 | 8.40E−03 | 1.90E−07 | 2.60E−05 |
| KLF5 | rs9530143 | G | 1.40E−08 | 7.40E−07 | 8.20E−06 | 0.07 |
| LMO7 | rs9544024 | A | 1.20E−12 | 1.50E−05 | 1.10E−12 | 8.80E−03 |
| COL4A1 | rs56152426 | A | 5.70E−10 | 9.10E−05 | 5.00E−08 | 0.33 |
| SPTSSA | rs72669675 | A | 1.00E−11 | 7.70E−06 | 3.70E−06 | 1.80E−05 |
| SOS2 | rs61755579 | C | 4.50E−08 | 0.02 | 1.90E−10 | 0.08 |
| FERMT2 | rs8009633 | G | 1.50E−13 | 5.30E−04 | 4.50E−16 | 0.01 |
| SIX1 | rs35155027 | G | 6.20E−17 | 1.30E−22 | 0.37 | 6.30E−23 |
| NPC2 | rs73294447 | T | 1.90E−10 | 7.60E−05 | 3.30E−08 | 0.03 |
| HERC2 | rs12913832 | A | 7.10E−09 | 3.10E−04 | 9.00E−07 | 9.20E−03 |
| ZNF280D | rs4601984 | G | 2.40E−10 | 6.90E−03 | 2.30E−09 | 0.02 |
| VPS13C | rs2249195 | A | 1.60E−13 | 7.50E−04 | 7.30E−18 | 0.96 |
| SALL1 | rs11859314 | G | 2.20E−10 | 5.60E−05 | 0.44 | 2.30E−21 |
| CDH11 | rs74984957 | G | 6.20E−11 | 7.70E−06 | 5.70E−13 | 0.1 |
| ADAMTS18 | rs75265191 | G | 1.40E−14 | 4.80E−06 | 2.80E−13 | 0.03 |
| FANCA | rs3743861 | G | 4.00E−10 | 8.10E−03 | 7.00E−13 | 0.15 |
| SMG6 | rs1563966 | G | 2.10E−08 | 2.80E−04 | 1.00E−05 | 0.02 |
| GAS7 | rs8064739 | A | 1.20E−15 | 1.80E−06 | 9.80E−12 | 0.1 |
| GAS7 | rs9913911 | A | 1.10E−58 | 4.60E−23 | 2.20E−58 | 0.11 |
| FLJ40194 | rs36006455 | T | 5.30E−09 | 4.90E−03 | 2.80E−07 | 0.02 |
| BCAS3 | rs3785856 | A | 3.70E−13 | 1.50E−04 | 1.20E−13 | 0.8 |

TABLE 10-continued

| Locus | SNP | EA | P-multivariate | P-Glaucoma | P-IOP | P-VCDR |
|---|---|---|---|---|---|---|
| PTBP1 | rs351973 | A | 4.30E−09 | 0.02 | 1.30E−05 | 7.50E−08 |
| KANK2 | rs440677 | G | 2.80E−10 | 4.00E−05 | 4.10E−06 | 1.10E−03 |
| CASC20 | rs6140009 | C | 2.40E−14 | 4.00E−06 | 0.44 | 1.50E−42 |
| LOC339593 | rs34952318 | G | 1.40E−11 | 1.40E−05 | 1.20E−16 | 0.18 |
| LOC339568 | rs6065171 | T | 9.80E−10 | 6.30E−05 | 1.90E−08 | 0.21 |
| PTPN1 | rs7273775 | C | 9.40E−10 | 8.30E−04 | 1.30E−08 | 0.05 |
| TXNRD2 | rs73148965 | G | 9.40E−12 | 6.10E−09 | 4.60E−09 | 0.42 |
| CHEK2 | rs738722 | T | 2.30E−15 | 3.30E−08 | 0.92 | 1.40E−35 |
| EMID1 | rs9608740 | A | 3.00E−14 | 1.80E−04 | 2.40E−17 | 0.26 |
| SYN3 | rs756481 | A | 3.60E−09 | 0.01 | 3.10E−12 | 0.7 |
| TRIOBP | rs4821712 | C | 1.30E−20 | 9.40E−05 | 6.10E−14 | 1.80E−13 |

Combinations of one or more of the above genetic loci or markers (or a variant of a SNP at the equivalent position) are contemplated.

In certain embodiments, the selected genetic loci or markers comprise one or more of the genetic loci or markers provided in Table 10.

In certain embodiments, the selected genetic loci or markers comprise one or more of the genetic loci or markers provided in Table 10 in conjunction with one or more genetic loci or markers provided in any one or more of Tables 1 to 9.

In certain embodiments, the selected genetic loci or markers comprise 90% or more, 80% or more, 70% or more, 60% or more, 50% or more, 40% or more, 30% or more, 20% or more, or 10% or more, 9% or more, 8% or more, 7% or more, 6% or more, 5% or more, 4% or more, 3% or more, 2% or more, or 1% or more of the selected of the genetic loci or markers, and/or the associated information, shown in Table 10.

Figure 11:
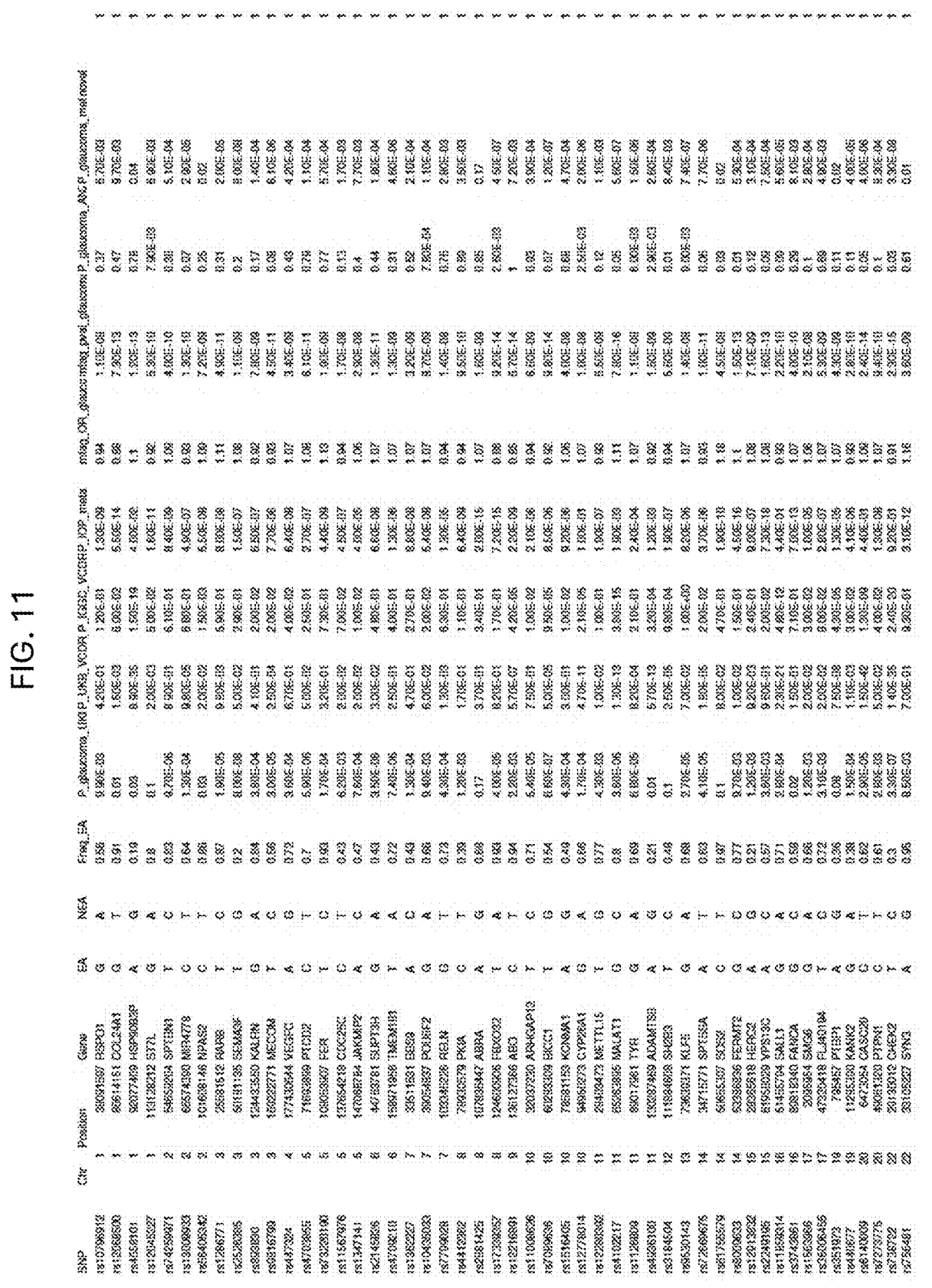
Figure 12:
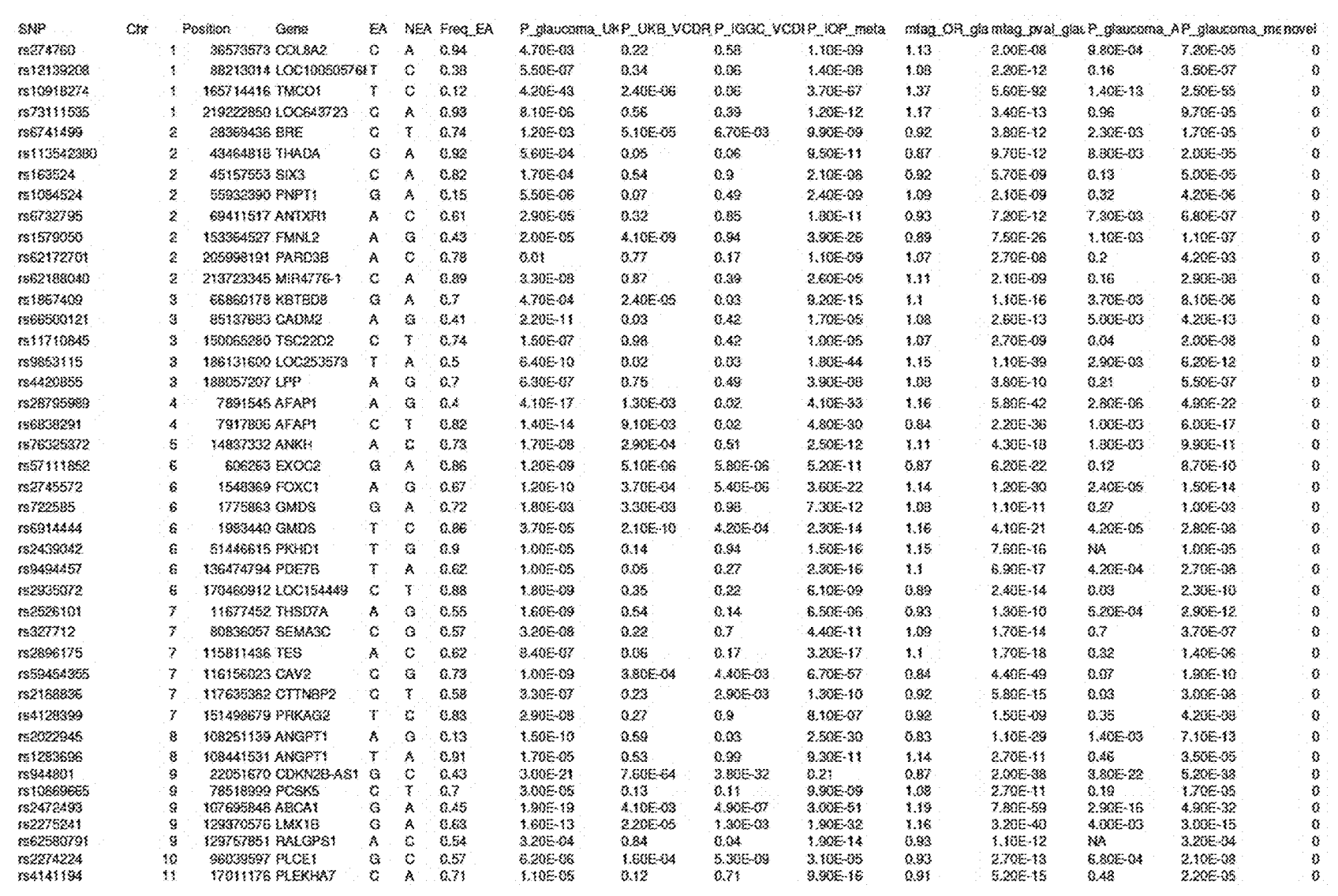

In certain embodiments, the selected genetic loci or markers comprise one or more of the selected genetic markers shown in FIGS. 11 and 12, as provided herein. Combinations of one or more of the above genetic loci or markers (or a variant of a SNP at the equivalent position) are contemplated.

In certain embodiments, the selected genetic loci or markers comprise 90% or more, 80% or more, 70% or more, 60% or more, 50% or more, 40% or more, 30% or more, 20% or more, or 10% or more, 9% or more, 8% or more, 7% or more, 6% or more, 5% or more, 4% or more, 3% or more, 2% or more, or 1% or more of the selected of the genetic loci or markers, and/or the associated information, shown in FIGS. 11 and 12.

In certain embodiments, the selected genetic loci or markers as described herein comprise one or more makers as shown in a table or a figure as described herein.

In certain embodiments, the selected genetic loci or markers as described herein comprise 90% or more, 80% or more, 70% or more, 60% or more, 50% or more, 40% or more, 30% or more, 20% or more, 19% or more, 18% or more, 17% or more, 16% or more, 15% or more, 14% or more, 13% or more, 12% or more, 11% or more, 10% or more, 9% or more, 8% or more, 7% or more, 6% or more, or 5% or more 4% or more, 3% or more, 2% or more, or 1% or more of the selected genetic loci shown in a table or figure as described herein.

In certain embodiments, the selected genetic loci or markers as described herein comprise greater than 90%, greater than 80%, greater than 70%, greater than 60%, greater than 50%, greater than 40%, greater than 30%, greater than 20%, greater than 19%, greater than 18%, greater than 17%, greater than 16%, greater than 15%, greater than 14%, greater than 13%, greater than 12%, greater than 11%, greater than 10%, greater than 9%, greater than 8%, greater than 7%, greater than 6% or more, greater than 5%, greater than 4%, greater than 3%, greater than 2%, or greater than 1% of the selected genetic loci shown in a table or figure as described herein.

In certain embodiments, the selected genetic loci or markers having an association with glaucoma comprise one or more of the selected genetic loci or markers shown in Table 1, Table 2 or Table 10.

In certain embodiments, the selected genetic loci or markers having an association with glaucoma comprise one or more of the selected genetic markers shown in Table 1, Table 3 or Table 10.

In certain embodiments, the selected genetic loci or markers having an association with an increased ocular pressure comprise one or more of the selected genetic loci shown in Table 4, Table 5 or Table 10.

In certain embodiments, the selected genetic loci or markers having an association with an increased ocular pressure comprise one or more of the selected genetic markers shown in Table 4, Table 6 or Table 10.

In certain embodiments, the selected genetic loci or markers having an association with an increased vertical cup to disk ratio size comprise one or more of the selected genetic loci shown in Table 7, Table 8 or Table 10.

In certain embodiments, the selected genetic loci or markers having an association with an increased vertical cup to disk ratio size comprise one or more of the selected genetic markers shown in Table 7, Table 9 or Table 10.

In certain embodiments, the selected genetic loci or markers having an association with a multi-trait test of glaucoma, intraocular pressure and vertical cup to disc ratio comprises one or more of selected genetic loci or markers shown in Table 10.

In certain embodiments, the selected genetic loci or markers having an association with a multi-trait test of glaucoma, intraocular pressure and vertical cup to disc ratio comprises one or more of selected genetic loci or markers shown in FIGS. 11 and 12.

In certain embodiments, the method comprises obtaining a biological sample from the subject to determine genetic content in the subject. The term "sample" refers to a sample obtained from a subject, or any derivative, extract, concentrate, mixture, or otherwise processed form thereof.

Methods for obtaining biological samples are known in the art. Examples of biological samples include biological fluids, blood samples, plasma samples, serum samples, urine samples, tear samples, saliva, swabs, buccal samples, hair samples, skin samples, dried blood, dried matrix, a biopsy, and fecal samples.

In certain embodiments, the biological sample is a biological fluid. In certain embodiments, the biological fluid comprises urine, blood, plasma or serum.

In certain embodiments, the biological sample comprises saliva and/or blood.

In certain embodiments, method comprises processing the biological sample to allow detection of genetic markers in the biological sample. For example, kits for extracting DNA from blood or urine are commercially available. In certain embodiments, the method comprises obtaining a biological sample from the subject and processing the sample to determine the genetic contents of the subject. In certain embodiments, the method comprises obtaining a biological sample from the subject and processing the sample to obtain genetic information in the subject.

Methods for determination of genetic content are known in the art. For example, methods are known in the art to determine DNA sequence information, allelic information, RNA information, DNA methylation information, histone modification information and epigenetic information. Other types of genetic information are contemplated.

For examples, methods for determination of genetic content include DNA microarray techniques, DNA sequencing, RNA sequencing and allele discrimination techniques, all of which are known in the art.

In certain embodiments, method comprises using a computer processor means to produce the risk score. Computer processor means and methods for using computer processor means to analyse data are known in the art.

In certain embodiments, the method comprises transferring data related to the genetic content over the internet to the computer processor means.

In certain embodiments, information relating to the genetic content is received from at least one user device in data communication with the computer processor means over a network. User devices are known in the art.

In certain embodiments, the method is used for diagnosis or prognosis of primary open angle glaucoma, screening for primary open angle glaucoma, diagnosis or prognosis of advanced glaucoma, diagnosis or prognosis non-advanced glaucoma, identification of an earlier age of onset of primary open angle glaucoma, identification of an earlier age of clinical diagnosis of glaucoma, the likelihood of surgery required for glaucoma; identification of rapid progression of early stage glaucoma, the likelihood of blindness from glaucoma, screening for primary open angle glaucoma in the population, screening to exclude a subject from follow-up monitoring for glaucoma, or the need for treatment for glaucoma. Other uses are contemplated.

In certain embodiments, the method is used prior to receiving information relating to clinical data/features. In certain embodiments, the method is used after receiving information relating to clinical data/features.

In certain embodiments, the present disclosure provides a method of assessing the risk of primary open angle glaucoma in a subject, the method comprising:

determining a risk score for the glaucoma in the subject on the basis of the genetic content of the subject at a plurality of selected genetic loci or markers and thereby assess the risk of primary open angle glaucoma in a subject, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio.

In certain embodiments, the present disclosure provides a method of assessing the risk of primary open angle glaucoma in a subject, the method comprising:

determining a risk score for the glaucoma in the subject on the basis of the genetic content of the subject at a plurality of selected genetic loci or markers and thereby assess the risk of primary open angle glaucoma in a subject, wherein the selected genetic loci or markers comprise genetic loci or markers having an association with a multi-trait test of glaucoma, intraocular pressure and vertical cup to disc ratio.

In certain embodiments, the present disclosure provides a method of assessing the risk of primary open angle glaucoma in a subject, the method comprising:

determining a risk score for the glaucoma in the subject on the basis of the genetic content of the subject at a plurality of selected genetic loci or markers and thereby assess the risk of primary open angle glaucoma in a subject, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides a method of assessing the risk of primary open angle glaucoma in a subject, the method comprising:

determining the genetic content of the subject at a plurality of selected genetic loci or markers;

determining a risk score for primary open angle glaucoma in the subject on the basis of the genetic content of the subject at the plurality of selected genetic loci or markers, wherein the selected genetic loci or markers comprise (i) genetic loci or markers having an association with glaucoma, and/or (ii) genetic loci or markers having an association with increased intraocular pressure and/or (iii) genetic loci or markers having an association with an increased vertical cup to disk ratio, and/or (iv) genetic loci or markers having an association with a multi-trait test of glaucoma, intraocular pressure and vertical cup to disc ratio; and thereby assess the risk of primary open angle glaucoma.

Certain embodiments of the present disclosure provide a method of diagnosis or prognosis for primary open angle glaucoma.

In certain embodiments, the present disclosure provides a method of diagnosis or prognosis for primary open angle glaucoma, the method comprising:

identifying a subject as suffering from, or being susceptible to, primary open angle glaucoma on the basis of the genetic content of the subject at a plurality of selected genetic loci or markers, wherein the selected genetic loci or markers comprise (i) genetic loci or markers having an association with glaucoma, and/or (ii) genetic loci or markers having an association with increased intraocular pressure and and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disk ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Methods for identifying genetic loci or markers having an association with a selected trait are as described herein.

Methods for identifying subjects based on their risk score are as described herein. Methods for diagnosis or prognosis based on risk score are as described herein. Subjects are as described herein.

In certain embodiments, the present disclosure provides a method of diagnosis or prognosis for primary open angle glaucoma, the method comprising:
  identifying a subject as suffering from, or being susceptible to, primary open angle glaucoma on the basis of the genetic content of the subject at a plurality of selected genetic loci or markers, wherein the selected genetic loci or markers comprise (i) genetic loci or markers having an association with glaucoma, and (ii) genetic loci or markers having an association with increased intraocular pressure and (iii) genetic loci or markers having an association with an increased vertical cup to disk ratio.

In certain embodiments, the present disclosure provides a method of diagnosis or prognosis for primary open angle glaucoma, the method comprising:
  identifying a subject as suffering from, or being susceptible to, primary open angle glaucoma on the basis of the genetic content of the subject at a plurality of selected genetic loci or markers, wherein the selected genetic loci or markers comprise (i) genetic loci or markers having an association with glaucoma, and (ii) genetic loci or markers having an association with increased intraocular pressure and (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides a method of diagnosis or prognosis for primary open angle glaucoma, the method comprising:

identifying a subject as suffering from, or being susceptible to, primary open angle glaucoma on the basis of the genetic content of the subject at a plurality of selected genetic loci or markers, wherein the selected genetic loci or markers comprise genetic loci or markers having an association with a multi-trait test of glaucoma, intraocular pressure and vertical cup to disc ratio.

Certain embodiments of the present disclosure provide a computer-readable medium.

In certain embodiments, the present disclosure provides a computer-readable medium encoded with programming instructions executable by a computer processor means to allow the computer processor means to:

process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disk ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Computer readable media are known in the art. Methods for processing data to determine a risk score are as described herein.

In certain embodiments, the present disclosure provides a computer-readable medium encoded with programming instructions executable by a computer processor means to allow the computer processor means to:

process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio.

In certain embodiments, the present disclosure provides a computer-readable medium encoded with programming instructions executable by a computer processor means to allow the computer processor means to:

process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides a computer-readable medium encoded with programming instructions executable by a computer processor means to allow the computer processor means to:

process data associated with the genetic content of a subject at a plurality of selected genetic loci or markers and determine a risk score for the subject suffering from, or being susceptible to, primary open angle glaucoma, wherein the selected genetic loci or markers comprise genetic loci or markers having an association with a multi-trait test of glaucoma, intraocular pressure and vertical cup to disc ratio.

Certain embodiments of the present disclosure provide a computer readable medium encoded with programming instructions executable by a computer processor means to process a method as described herein.

Certain embodiments of the present disclosure provide a computer processor means comprising a computer-readable medium as described herein. Computer processor means are known in the art.

Certain embodiments of the present disclosure provide a system for determining the risk of primary open angle glaucoma in a subject.

In certain embodiments, the present disclosure provides a system for determining the risk of primary open angle glaucoma in a subject, the system comprising a computer processor having a computer-readable medium encoded with programming instructions executable by the computer processor means to allow the computer processor means to:

process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disk ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

In certain embodiments, the data is transferred over the internet to the computer processing means.

In certain embodiments, information relating to the genetic content is received from at least one user device in data communication with the computer processor means over a network.

In certain embodiments, the system further comprises a DNA microarray or a DNA sequencer.

In certain embodiments, the present disclosure provides a system for determining the risk of primary open angle glaucoma in a subject, the system comprising a computer processor having a computer-readable medium encoded with programming instructions executable by the computer processor means to allow the computer processor means to:
  process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and (ii) genetic loci or markers having an association with increased intraocular pressure and (iii) genetic loci or markers having an association with an increased vertical cup to disk ratio.

In certain embodiments, the present disclosure provides a system for determining the risk of primary open angle glaucoma in a subject, the system comprising a computer processor having a computer-readable medium encoded with programming instructions executable by the computer processor means to allow the computer processor means to:
  process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and (ii) genetic loci or markers having an association with increased intraocular pressure and (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides a system for determining the risk of primary open angle glaucoma in a subject, the system comprising a computer processor having a computer-readable medium encoded with programming instructions executable by the computer processor means to allow the computer processor means to:
  process data associated with the genetic content of a subject at a plurality of selected genetic loci or markers and determine a risk score for the subject suffering from, or being susceptible to, primary open angle glaucoma, wherein the selected genetic loci or markers comprise genetic loci or markers having an association with a multi-trait test of glaucoma, intraocular pressure and vertical cup to disc ratio.

Certain embodiments of the present disclosure provide a method of assessing one or more of onset, progression, and severity of primary open angle glaucoma in a subject.

In certain embodiments, the present disclosure provides a method of assessing one or more of onset, progression, and severity of primary open angle glaucoma in a subject, the method comprising:
  determining one or more of onset, progression and severity of primary open angle glaucoma on the subject on the basis of the genetic content of the subject at a plurality of selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disc ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Methods for identifying genetic loci or markers having an association with a selected trait are as described herein.

Methods for assessing subjects for onset, progression, and severity of primary open angle glaucoma based on their risk score are as described herein.

In certain embodiments an increased risk score is indicative of earlier onset of primary open angle glaucoma.

In certain embodiments, an increased risk score is indicative of an earlier onset by at least 1 year, at least 2 years at least 3, years, at least 4 years or at least 5 years.

In certain embodiments an increased risk score is indicative of a faster progression of primary open angle glaucoma.

In certain embodiments an increased risk score is indicative of increased severity of primary open angle glaucoma. In certain embodiments, an increased risk score is indicative of further nerve head damage over time.

In certain embodiments, an increased risk score is indicative of an increased need for surgery.

In certain embodiments, the present disclosure provides a method of assessing one or more of onset, progression, and severity of primary open angle glaucoma in a subject, the method comprising:
  determining one or more of onset, progression and severity of primary open angle glaucoma on the subject on the basis of the genetic content of the subject at a plurality of selected genetic loci or markers, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio.

In certain embodiments, the present disclosure provides a method of assessing one or more of onset, progression, and severity of primary open angle glaucoma in a subject, the method comprising:
  determining one or more of onset, progression and severity of primary open angle glaucoma on the subject on the basis of the genetic content of the subject at a plurality of selected genetic loci or markers, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides a method of assessing one or more of onset, progression, and severity of primary open angle glaucoma in a subject, the method comprising:
  determining one or more of onset, progression and severity of primary open angle glaucoma on the subject on the basis of the genetic content of the subject at a plurality of selected genetic loci or markers, wherein the selected genetic loci or markers comprise genetic loci or markers having an association with a multi-trait test of glaucoma, intraocular pressure and vertical cup to disc ratio.

Certain embodiments of the present disclosure provide a method of treating a subject suffering from, susceptible to, primary open angle glaucoma, by using a method as described herein to identify a subject suitable for treatment.

In certain embodiments, the present disclosure provides a method of treating a subject suffering from, susceptible to, primary open angle glaucoma, the method comprising:

identifying a subject at increased risk of primary open angle glaucoma using a risk score based on the genetic content of the subject at a plurality of selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and treating the subject so identified.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disk ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Methods for treating a subject for primary open angle glaucoma are as described herein. Methods include pharmacological and non-pharmacological methods of treatment.

Methods for identifying genetic loci or markers having an association with a selected trait are as described herein.

Methods for determining a risk score are as described herein.

In certain embodiments, a drug and/or surgical intervention strategy is used to treat the subject.

In certain embodiments, the present disclosure provides a method of treating a subject at increased risk of primary open angle glaucoma, the method comprising identifying a subject at increased risk of primary open angle glaucoma using a method as described herein and treating the subject so identified.

Certain embodiments of the present disclosure provide a method of identifying a genetic locus or marker associated with an increased risk of primary open angle glaucoma.

In certain embodiments, the present disclosure provides a method of identifying a genetic locus associated with an increased risk of primary open angle glaucoma, the method comprising:

using a multi-trait model to test whether a candidate genetic locus or marker is associated with an increased risk of primary open angle glaucoma, the multi-trait model comprising combining genetic information on the candidate genetic locus or marker with genetic content from selected genetic loci or markers, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and identifying the candidate genetic locus or marker as a locus or marker associated with an increased risk of primary open angle glaucoma.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disk ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Methods for identifying genetic loci or markers having an association with a selected trait are as described herein. Methods for using multi-trait models are as described herein.

In certain embodiments, the present disclosure provides a method of identifying a genetic locus associated with an increased risk of primary open angle glaucoma, the method comprising:

using a multi-trait model to test whether a candidate genetic locus or marker is associated with an increased risk of primary open angle glaucoma, the multi-trait model comprising combining genetic information on the candidate genetic locus or marker with genetic content from selected genetic loci or markers, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio, and/or (iv) genetic loci or markers having an association with a multi-trait test of glaucoma, intraocular pressure and vertical cup to disc ratio; and identifying the candidate genetic locus or marker as a locus or marker associated with an increased risk of primary open angle glaucoma.

In certain embodiments, the present disclosure provides a method of identifying a genetic locus associated with an increased risk of primary open angle glaucoma, the method comprising:

using a multi-trait model to test whether a candidate genetic locus or marker is associated with an increased risk of primary open angle glaucoma, the multi-trait model comprising combining genetic information on the candidate genetic locus or marker with genetic content from selected genetic loci or markers, wherein the selected genetic loci or markers comprise genetic loci or markers having an association with a multi-trait test of glaucoma, intraocular pressure and vertical cup to disc ratio; and identifying the candidate genetic locus or marker as a locus or marker associated with an increased risk of primary open angle glaucoma.

Certain embodiments of the present disclosure provide a method for producing a score for assessing the risk of primary open angle glaucoma.

In certain embodiments, the present disclosure provides a method for producing a score for assessing the risk of primary open angle glaucoma, the method comprising:

using a multi-trait model to combine genetic information on a plurality of selected genetic loci or markers having an association with primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and producing a score for assessing the risk of primary open angle glaucoma on the basis of results of the multi-trait model.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with increased intraocular pressure are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disc ratio are as described herein.

In certain embodiments, the selected genetic loci or markers comprise genetic loci or markers having an association with a multi-trait test of glaucoma, intraocular pressure and vertical cup to disc ratio. Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

Methods for identifying genetic loci or markers having an association with a selected trait are as described herein. Methods for using multi-trait models are as described herein. Methods for producing a risk score are as described herein.

In certain embodiments, the present disclosure provides a method for producing a score for assessing the risk of primary open angle glaucoma, the method comprising:
  using a multi-trait model to combine genetic information on a plurality of selected genetic loci or markers having an association with primary open angle glaucoma, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio; and
  producing a score for assessing the risk of primary open angle glaucoma on the basis of results of the multi-trait model.

In certain embodiments, the present disclosure provides a method for producing a score for assessing the risk of primary open angle glaucoma, the method comprising:
  using a multi-trait model to combine genetic information on a plurality of selected genetic loci or markers having an association with primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio; and
  producing a score for assessing the risk of primary open angle glaucoma on the basis of results of the multi-trait model.

In certain embodiments, the present disclosure provides a method for producing a score for assessing the risk of primary open angle glaucoma, the method comprising:
  using a multi-trait model to combine genetic information on a plurality of selected genetic loci or markers having an association with primary open angle glaucoma, wherein the selected genetic loci or markers comprise genetic loci or markers having an association with a multi-trait test of glaucoma, intraocular pressure and vertical cup to disc ratio; and producing a score for assessing the risk of primary open angle glaucoma on the basis of results of the multi-trait model.

Certain embodiments of the present disclosure provide a method of assessing the risk of primary open angle glaucoma in a subject, the method comprising using a risk score produced by a method as described herein to assess the risk of primary open angle glaucoma in the subject.

Certain embodiments of the present disclosure provide computer software encoded with programming instructions executable by a computer processor means to use a method as described herein.

Certain embodiments of the present disclosure provide computer software encoded with programming instructions executable by a computer processor means as described herein to allow the computer processor means to determine the risk of primary open angle glaucoma.

Certain embodiments of the present disclosure provide computer software encoded with programming instructions executable by a computer processor means as described herein to allow the computer processor means to determine the risk of primary open angle glaucoma.

In certain embodiments, the present disclosure provides computer software encoded with programming instructions executable by a computer processor means to allow the computer processor means to process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the selected genetic loci or markers comprise genetic loci or markers having an association with glaucoma. In certain embodiments, the selected genetic loci or markers comprise genetic loci or markers having an association with advanced glaucoma. Selected genetic loci or markers having an association with glaucoma are as described herein.

In certain embodiments, the selected genetic loci or markers comprise genetic loci or markers having an association with increased intraocular pressure. Selected genetic loci or markers having an association with an increased vertical cup to disc ratio are as described herein.

In certain embodiments, the selected genetic loci or markers comprise genetic loci or markers having an association with an increased vertical cup to disk ratio. In certain embodiments, the selected genetic loci or markers comprise genetic loci or markers having an association with an increased vertical cup to disk ratio corrected for optic nerve head size. Selected genetic loci or markers having an association with an increased vertical cup to disc ratio are as described herein.

In certain embodiments, the selected genetic loci or markers comprise genetic loci or markers having an association with a multi-trait test of glaucoma, intraocular pressure and vertical cup to disc ratio.

Selected genetic loci or markers having an association with a multi-trait test of glaucoma, intraocular pressure and vertical cup to disc ratio are as described herein.

In certain embodiments, the selected genetic loci or markers have an association with an aggregated version (multivariate test) of glaucoma, intraocular pressure and vertical cup to disc ratio. Under this multivariate model, while the selected genetic loci or markers may not reach significance for glaucoma, intraocular pressure and vertical cup to disk ratio taken individually, significance is achieved under the multivariate test.

In certain embodiments, the selected genetic loci or markers comprise genetic loci or markers having an association with glaucoma and genetic loci or markers having an association with increased intraocular pressure.

In certain embodiments, the selected genetic loci or markers comprise genetic loci or markers having an association with glaucoma and genetic loci or markers having an association with an increased vertical cup to disk ratio.

In certain embodiments, the selected genetic loci or markers comprise genetic loci or markers having an association with increased intraocular pressure and genetic loci or markers having an association with an increased vertical cup to disk ratio.

In certain embodiments, the selected genetic loci comprise genetic loci or markers having an association with glaucoma, and genetic loci or markers having an association with a multi-trait test of glaucoma, intraocular pressure and vertical cup to disc ratio.

In certain embodiments, the selected genetic loci comprise genetic loci or markers having an association with increased intraocular pressure, and genetic loci or markers having an association with a multi-trait test of glaucoma, intraocular pressure and vertical cup to disc ratio.

In certain embodiments, the selected genetic loci comprise genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio.

In certain embodiments, the selected genetic loci or markers comprise genetic loci or markers having an association with glaucoma, and genetic loci or markers having an association with increased intraocular pressure, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with increased intraocular pressure and genetic loci or markers having an association with an increased vertical cup to disk ratio, and genetic loci or markers having an association with a multi-trait test of glaucoma, intraocular pressure and vertical cup to disc ratio.

In certain embodiments, the selected genetic loci or markers comprise genetic loci or markers having an association with glaucoma, and genetic loci or markers having an association with increased intraocular pressure, and genetic loci or markers having an association with an increased vertical cup to disk ratio, and genetic loci or markers having an association with a multi-trait test of glaucoma, intraocular pressure and vertical cup to disc ratio.

In certain embodiments, the present disclosure provides computer software encoded with programming instructions executable by a computer processor means to allow the computer processor means to process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and (ii) genetic loci or markers having an association with increased intraocular pressure, and (iii) genetic loci or markers having an association with an increased vertical cup to disk ratio.

In certain embodiments, the present disclosure provides computer software encoded with programming instructions executable by a computer processor means to allow the computer processor means to process data associated with the genetic content of a subject at a plurality of selected genetic loci or markers and determine a risk score for the subject suffering from, or being susceptible to, primary open angle glaucoma, wherein the selected genetic loci or markers comprise (i) genetic loci or markers having an association with glaucoma, and/or (ii) genetic loci or markers having an association with increased intraocular pressure, and/or (iii) genetic loci or markers having an association with an increased vertical cup to disk ratio, and/or (iv) genetic loci or markers having an association with a multi-trait test of glaucoma, intraocular pressure and vertical cup to disc ratio.

In certain embodiments, the present disclosure provides computer software encoded with programming instructions executable by a computer processor means to allow the computer processor means to process data associated with the genetic content of a subject at a plurality of selected genetic loci or markers and determine a risk score for the subject suffering from, or being susceptible to, primary open angle glaucoma, wherein the selected genetic loci or markers genetic loci or markers having an association with a multi-trait test of glaucoma, intraocular pressure and vertical cup to disc ratio.

Certain embodiments of the present disclosure provide a method of assessing the risk of primary open angle glaucoma in a subject, the method comprising determining a risk score for the glaucoma in the subject using one or more of the selected genetic loci or markers as provided in any one of Tables 1 to 10.

Certain embodiments of the present disclosure provide a method of diagnosis or prognosis for primary open angle glaucoma, the method comprising identifying a subject as suffering from, or being susceptible to, primary open angle glaucoma using one or more of the selected genetic loci or markers as provided in any one of Tables 1 to 10.

Certain embodiments of the present disclosure provide a computer-readable medium encoded with programming instructions executable by a computer processor means to allow the computer processor means to process data associated with one or more of the selected genetic loci or markers as provided in any one of Tables 1 to 10 and/or FIGS. 11 and 12 to determine a risk score for the subject suffering from, or being susceptible to, primary open angle glaucoma.

Certain embodiments of the present disclosure provide a computer processor means comprising a computer-readable medium encoded with programming instructions executable by a computer processor means to allow the computer processor means to process data associated with one or more of the selected genetic loci or markers as provided in any one of Tables 1 to 10 and/or FIGS. 11 and 12 to determine a risk score for the subject suffering from, or being susceptible to, primary open angle glaucoma.

Certain embodiments of the present disclosure provide a system for determining the risk of a primary open angle glaucoma in a subject, the system comprising a computer processor having a computer-readable medium encoded with programming instructions executable by the computer processor means to allow the computer processor means to process data associated with one or more of the selected genetic loci or markers as provided in any one of Tables 1 to 10 and/or FIGS. 11 and 12 to determine a risk score for the subject suffering from, or being susceptible to, primary open angle glaucoma.

Certain embodiments of the present disclosure provide a method of assessing one or more of onset, progression, and severity of primary open angle glaucoma in a subject, the method comprising determining a risk score for glaucoma in the subject using one or more of the selected genetic loci or markers as provided in any one of Tables 1 to 10 and/or FIGS. 11 and 12.

Certain embodiments of the present disclosure provide a method of treating a subject suffering from, susceptible to, primary open angle glaucoma, the method comprising:
  identifying a subject at increased risk of primary open angle glaucoma using a risk score using one or more of the selected genetic loci or markers as provided in any one of Tables 1 to 10 and/or FIGS. 11 and 12; and treating the subject so identified.

Certain embodiments of the present disclosure provide a method of identifying a genetic locus associated with an increased risk of primary open angle glaucoma, the method comprising:
  using a multi-trait model to test whether a candidate genetic locus or marker is associated with an increased risk of primary open angle glaucoma, the multi-trait model comprising combining genetic information on the candidate genetic locus or marker with genetic content of one or more of the selected genetic loci or markers as provided in any one of Tables 1 to 10 and/or FIGS. 11 and 12; and
  identifying the candidate genetic locus or marker as a locus associated with an increased risk of primary open angle glaucoma.

Certain embodiment of the present disclosure provide method for producing a score for assessing the risk of primary open angle glaucoma, the method comprising:
  using a multi-trait model to combine genetic information on a plurality of selected genetic loci or markers as provided in any one of Tables 1 to 10 and/or FIGS. 11 and 12; and
  producing a score for assessing the risk of primary open angle glaucoma on the basis of results of the multi-trait model Standard techniques and equipment may be used for recombinant DNA technology, DNA sequencing, DNA arrays, oligonucleotide synthesis, molecular biology and enzymatic reactions. The foregoing techniques and procedures may be generally performed according to methods known in the art and/or as commercially available, and are as described for example in Sambrook et al. Molecular Cloning: A Laboratory Manual (4th ed., Cold Spring Harbor Laboratory Press, Cold Spring Harbor, N.Y. (1989)) and Ausubel et al Current Protocols in Molecular Biology (2003) John Wiley & Sons, both of which are herein incorporated by reference.

The present disclosure is further described by the following examples. It is to be understood that the following description is for the purpose of describing particular embodiments only and is not intended to be limiting with respect to the above description.

Example 1—Genome-Wide Association Study of Intraocular Pressure Uncovers New Pathways to Glaucoma Over the past decade genome-wide association studies (GWAS) have implicated 14 independent loci involved in the pathogenesis of POAG, and an additional eight loci have been associated with primary angle-closure glaucoma (PACG). The classification of POAG and PACG is based on the anatomical configuration of the iridocorneal angle, where outflow of aqueous humor occurs through the trabecular meshwork. Regardless of the glaucoma classification, it is well established that elevated IOP can lead to irreversible optic nerve degeneration and corresponding visual field deficits. Currently all drugs used to treat glaucoma lower IOP by either increasing aqueous outflow (through the trabecular meshwork or uveoscleral tracts), or decreasing aqueous production. Understanding which genes influence IOP may open new avenues for glaucoma treatment. We report results from a large GWAS for IOP and glaucoma, and explore the genetic relationship between the endophenotype and the disease.

Figure 2A:
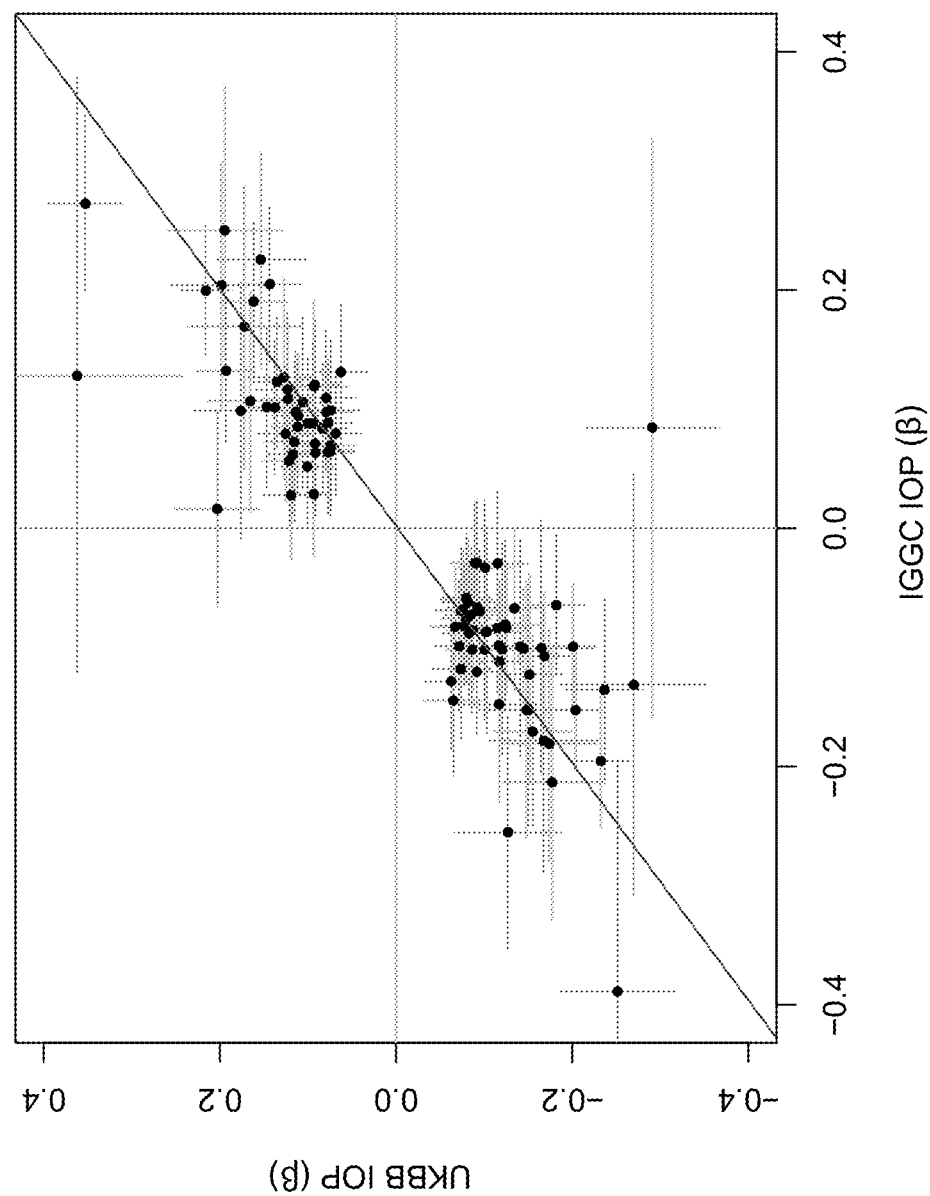
FIG. 2 shows regression coefficients (β in mmHg) or effect size for the top associated SNPs at each locus associated with intraocular pressure (IOP) at the genome-wide significant level. 95% confidence intervals are displayed in grey. (a) Comparison of regression coefficients in the UK Biobank (y-axis) and the International Glaucoma Genetic Consortium dataset (x-axis; Pearson's correlation coefficient=0.85). The solid line indicates the line of best fit. (b) Concordance between regression coefficients for IOP in 133,492 people of Northern European descent (x-axis) and the direct effect size (log odds ratio) in 11,018 glaucoma cases versus 126,069 controls (y-axis; Pearson's correlation coefficient=0.93). The solid line indicates the line of best fit through the 101 IOP SNPs. The 101 IOP SNPs are shown as black dots. SNPs identified in the GWAS of glaucoma are superimposed in red/pink/orange; those in red show $P<0.05$ with IOP, those in pink show $P<0.05$ with VCDR but not IOP and the SNPs in orange are at CDKN2B-AS1 and SIX6, which are known to act independently of IOP.

To identify SNPs influencing IOP, we undertook a meta-analysis of IOP GWAS from the publicly available UK Biobank (UKBB; see URLs) and previously published data from the International Glaucoma Genetic Consortium (IGGC). To determine which of the peak SNPs were statistically independent and thus potentially informative in allelic risk profiling, we used the program GCTA-COJO to perform conditional analysis on the summary meta-analysis (see URLs, methods section, and Yang, J. et al. Conditional and joint multiple-SNP analysis of GWAS summary statistics identifies additional variants influencing complex traits. *Nat. Genet.* 44, 369-75, S1-3 (2012)). A total of 106 independent SNPs (uncorrelated with other peak SNPs) surpassed the genome-wide significance threshold ($P<5\times10^{-8}$, FIG. 1 & FIG. 2). For downstream analysis, we removed five peak SNPs influencing IOP measurement through corneal biomechanics. The removed SNPs were rs66724425 in ADAMTS6, previously shown to be associated with central corneal thickness, and SNPs rs1570204, rs78658973, rs12492846 and rs2797560, which were more strongly associated (i.e. lower P-value) with corneal hysteresis (a measure of viscous damping in the cornea that influences IOP measurement), than with IOP Among the remaining 101 SNPs, we found strong concordance (Pearson's correlation coefficient=0.85; P<0.001) in the effect sizes between IGGC and UKBB (FIG. 2a). Of the 101 associated SNPs, 85 had not been previously associated with IOP, whilst 16 had been previously associated with either IOP or glaucoma at the genome-wide significant level (marked in blue in FIG. 1). The only previously identified IOP locus that we did not replicate at the genome-wide significant level was ADAMTS8 (peak SNP rs56009602, P=6.2×10$^{-6}$).

The lead SNPs and their assigned locus are as follows:

| Lead SNP | Assigned Locus Name |
|---|---|
| rs12123086 | TRAPPC3 |
| rs4074961 | RSPO1 |
| rs2279948 | COL24A1 |
| rs35638741 | LINC01364 |
| rs12045227 | ST7L |
| rs10918274 | TMCO1 |
| rs73111535 | LYPLAL1-AS1 |
| rs10189434 | BRE |
| rs113542380 | THADA |
| rs163524 | SIX3 |
| rs4627617 | SPTBN1 |
| rs4672075 | EFEMP1 |
| rs6732795 | ANTXR1 |
| rs11123857 | NPAS2 |
| rs1579050 | FMNL2 |
| rs16837021 | PARD3B |
| rs3791979 | TNS1 |
| rs6781336 | LRIG1 |
| rs73174309 | MECOM |
| rs16856911 | FNDC3B |
| rs9853115 | DGKG |
| rs28520091 | AFAP1 |
| rs28500712 | AFAP1 |
| rs31918 | ANKH |
| rs10036789 | PTCD2 |
| rs73220177 | FER |
| rs113985657 | EXOC2 |
| rs2745572 | FOXC1 |
| rs3778523 | GMDS |
| rs9405157 | GMDS |
| rs3134954 | TNXB |
| rs1755056 | RUNX2 |
| rs17752199 | PKHD1 |
| rs9494457 | PDE7B |
| rs3013274 | LOC154449 |
| rs12674371 | POU6F2 |
| rs327716 | SEMA3C |
| rs55892100 | TES |
| rs10281637 | CAV2 |
| rs2188836 | CTTNBP2 |
| rs12548673 | C8orf48 |
| rs35174414 | 8q21 |
| rs1381486 | ABRA |
| rs2022945 | ANGPT1 |
| rs66602224 | ANGPT1 |
| rs4496939 | ANGPT1 |
| rs62520914 | FBXO32 |
| rs10869665 | PCSK5 |
| rs2472496 | ABCA1 |
| rs6478746 | LMX1B |
| rs10819187 | LMX1B |
| rs12377624 | LMX1B |
| rs11795066 | ANGPTL2 |
| rs8176747 | ABO |
| rs1556659 | 10q26 |
| rs4141194 | PLEKHA7 |
| rs10767734 | MIR8068 |
| rs2697920 | MYBPC3 |
| rs7123436 | PTPRJ |
| rs746491 | ME3 |
| rs11217878 | ARHGEF12 |
| rs7924522 | ETS1 |
| rs7338461 | LMO7 |
| rs61755579 | SOS2 |
| rs12147852 | FERMT2 |
| rs73296215 | LTBP2 |
| rs28575268 | ZNF280D |
| rs4775427 | VPS13C |
| rs1874458 | CDH11 |
| rs12444539 | ADAMTS18 |
| rs3743860 | FANCA |
| rs10852918 | GAS7 |
| rs9913911 | GAS7 |
| rs199529 | NSF |
| rs1558225 | BCAS3 |
| rs34952318 | LOC339593 |
| rs6065171 | LINC01370 |
| rs6095946 | PTPN1 |
| rs4629237 | LINC00314 |
| rs76945759 | TXNRD2 |
| rs9608740 | EMID1 |
| rs756481 | SYN3 |
| rs5756813 | TRIOBP |

Similar to other complex traits, it is likely that additional SNPs beyond the 101 described above, are also associated with IOP, but do not reach genome-wide significance. To estimate the overall contribution of all common variants (i.e. SNP MAF>0.01) to IOP, we applied LD Score regression (Bulik-Sullivan, B. K. et al. L D Score regression distinguishes confounding from polygenicity in genome-wide association studies. *Nat. Genet.* 47, 291-295 (2015)) which yielded a SNP heritability estimate of 0.16 (standard error, SE=0.01). We then considered the distribution of association P-values across the genome. Since there was genomic inflation (genomic control lambda=1.26), we computed the LD Score regression intercept to assess whether this genomic inflation was attributable to many variants of small effect (polygenes) or due to the effect of issues such as population structure. The LD Score regression intercept was 1.06 (SE=0.01), indicating that the majority of the inflation was due to polygenes.

We then performed a GWAS meta-analysis for glaucoma by combining data from UKBB glaucoma cases and controls (selected to be independent of those in our IOP GWAS; 7947 cases, 119318 controls) with 3,071 cases from the Australian and New Zealand Registry of Advanced Glaucoma (ANZRAG) and 6,750 historic controls (see the methods section for full description). Our genome-wide analysis of glaucoma found 24 genome-wide significant loci (Table 11). Similar to IOP, there was genomic inflation due to the effect of polygenes, but the intercept of the univariate LD score regression obtained from the meta-analysed data was close to 1 (0.95, SE=0.01), suggesting that our results were not biased by population substructure or cryptic relatedness.

| Chr | Position | SNP | EA | NEA | OR POAG | 95% CIs POAG | P POAG | IOP Effect | SE IOP | PIOP | P VCDRA^ | Nearest gene |
|---|---|---|---|---|---|---|---|---|---|---|---|---|
| 1 | 165736880 | rs7518099 | T | C | 0.73 | 0.70-0.76 | 2.35 × 10$^{-52}$ | −0.33 | 0.02 | 3.96 × 10$^{-67}$ | 0.058 | LOC100147773, TMCO1 |
| 9 | 22051670 | rs944801 | C | G | 1.22 | 1.17-1.27 | 8.00 × 10$^{-36}$ | 0.02 | 0.01 | 0.232 | 3.85 × 10$^{-32}$ | CDKN2B-AS1 |
| 9 | 107695848 | rs2472493* | A | G | 0.84 | 0.80-0.87 | 4.30 × 10$^{-30}$ | −0.19 | 0.01 | 3.62 × 10$^{-50}$ | 4.85 × 10$^{-07}$ | LOC105376196, ABCA1 |

-continued

| Chr | Position | SNP | EA | NEA | OR POAG | 95% CIs POAG | P POAG | IOP Effect | SE IOP | PIOP | P VCDRA^ | Nearest gene |
|---|---|---|---|---|---|---|---|---|---|---|---|---|
| 14 | 60957279 | rs2093210 | T | C | 0.86 | 0.83-0.90 | $6.29 \times 10^{-22}$ | -0.009 | 0.01 | 0.483 | $1.22 \times 10^{-09}$ | C14orf39, SIX6 |
| 17 | 10031183 | rs9913911 | A | G | 1.16 | 1.12-1.21 | $2.13 \times 10^{-21}$ | 0.21 | 0.01 | $1.59 \times 10^{-57}$ | $5.62 \times 10^{-06}$ | GAS7 |
| 4 | 7891545 | rs28795989 | A | G | 1.15 | 1.11-1.20 | $1.90 \times 10^{-20}$ | 0.15 | 0.01 | $2.94 \times 10^{-32}$ | 0.019 | AFAP1 |
| 9 | 129378026 | rs945686 | C | G | 0.86 | 0.83-0.90 | $2.58 \times 10^{-17}$ | -0.14 | 0.01 | $4.25 \times 10^{-22}$ | 0.016 | LMX1B |
| 6 | 1548369 | rs2745572 | A | G | 1.13 | 1.08-1.17 | $1.35 \times 10^{-13}$ | 0.13 | 0.01 | $2.66 \times 10^{-22}$ | $5.41 \times 10^{-06}$ | LOC102723944, GMDS |
| 3 | 85095766 | rs9284802 | A | G | 0.90 | 0.86-0.93 | $1.56 \times 10^{-12}$ | -0.05 | 0.01 | $4.74 \times 10^{-05}$ | 0.665 | CADM2 |
| 11 | 120248493 | rs58073046 | A | G | 0.85 | 0.82-0.89 | $1.99 \times 10^{-12}$ | -0.20 | 0.02 | $1.03 \times 10^{-22}$ | 0.189 | ARHGEF12 |
| 7 | 11679113 | rs12699251 | A | G | 0.90 | 0.86-0.93 | $4.16 \times 10^{-12}$ | -0.05 | 0.01 | $9.98 \times 10^{-05}$ | 0.100 | THSD7A |
| 8 | 108278616 | rs10505100 | A | C | 0.84 | 0.81-0.88 | $4.86 \times 10^{-12}$ | -0.21 | 0.02 | $1.45 \times 10^{-27}$ | 0.043 | ANGPT1 |
| 7 | 116153025 | rs2024211 | A | C | 0.90 | 0.86-0.93 | $9.48 \times 10^{-12}$ | -0.22 | 0.01 | $2.90 \times 10^{-55}$ | 0.004 | CAV1, CAV2 |
| 3 | 186131600 | rs9853115 | A | T | 0.90 | 0.87-0.94 | $4.35 \times 10^{-11}$ | -0.18 | 0.01 | $2.84 \times 10^{-43}$ | 0.026 | DGKG, LOC107986164, TBCCD1 |
| 5 | 14851094 | rs61394862 | T | C | 0.90 | 0.86-0.93 | $4.13 \times 10^{-10}$ | -0.09 | 0.01 | $8.42 \times 10^{-11}$ | 0.781 | ANKH |
| 6 | 170454915 | rs2935057 | A | G | 1.15 | 1.11-1.20 | $8.02 \times 10^{-10}$ | 0.11 | 0.02 | $1.30 \times 10^{-08}$ | 0.250 | LOC101929614, LOC105378153 |
| 6 | 637465 | rs2073006 | T | C | 1.14 | 1.10-1.18 | $1.20 \times 10^{-09}$ | 0.11 | 0.02 | $2.29 \times 10^{-09}$ | $1.81 \times 10^{-05}$ | EXOC2 |
| 10 | 94942423 | rs61861119 | A | G | 0.91 | 0.88-0.95 | $2.56 \times 10^{-09}$ | 0.01 | 0.01 | 0.313 | $1.56 \times 10^{-05}$ | MYOF, XRCC6P1 |
| 22 | 19854006 | rs8141433 | A | G | 1.15 | 1.11-1.20 | $3.04 \times 10^{-09}$ | 0.08 | 0.02 | $2.85 \times 10^{-06}$ | 0.235 | TXNRD2 |
| 10 | 60338753 | rs4141671 | T | C | 0.91 | 0.88-0.95 | $8.67 \times 10^{-09}$ | -0.05 | 0.01 | 0.0004 | 0.0001 | BICC1 |
| 3 | 169252883 | rs73174345 | T | G | 0.84 | 0.80-0.89 | $1.53 \times 10^{-08}$ | -0.07 | 0.03 | 0.008 | 0.732 | MECOM |
| 7 | 117603820 | rs1013278 | C | G | 1.09 | 1.05-1.14 | $2.99 \times 10^{-08}$ | 0.08 | 0.01 | $3.32 \times 10^{-10}$ | 0.003 | CTTNBP2, CFTR |
| 11 | 128380742 | rs7924522 | A | C | 1.09 | 1.05-1.14 | $3.33 \times 10^{-08}$ | 0.11 | 0.01 | $3.99 \times 10^{-15}$ | 0.090 | ETS1 |
| 3 | 150059342 | rs11710139 | A | G | 0.90 | 0.87-0.94 | $5.00 \times 10^{-08}$ | -0.06 | 0.01 | $3.89 \times 10^{-05}$ | 0.463 | LOC107986141, LOC107986142 |

Figure 2B:
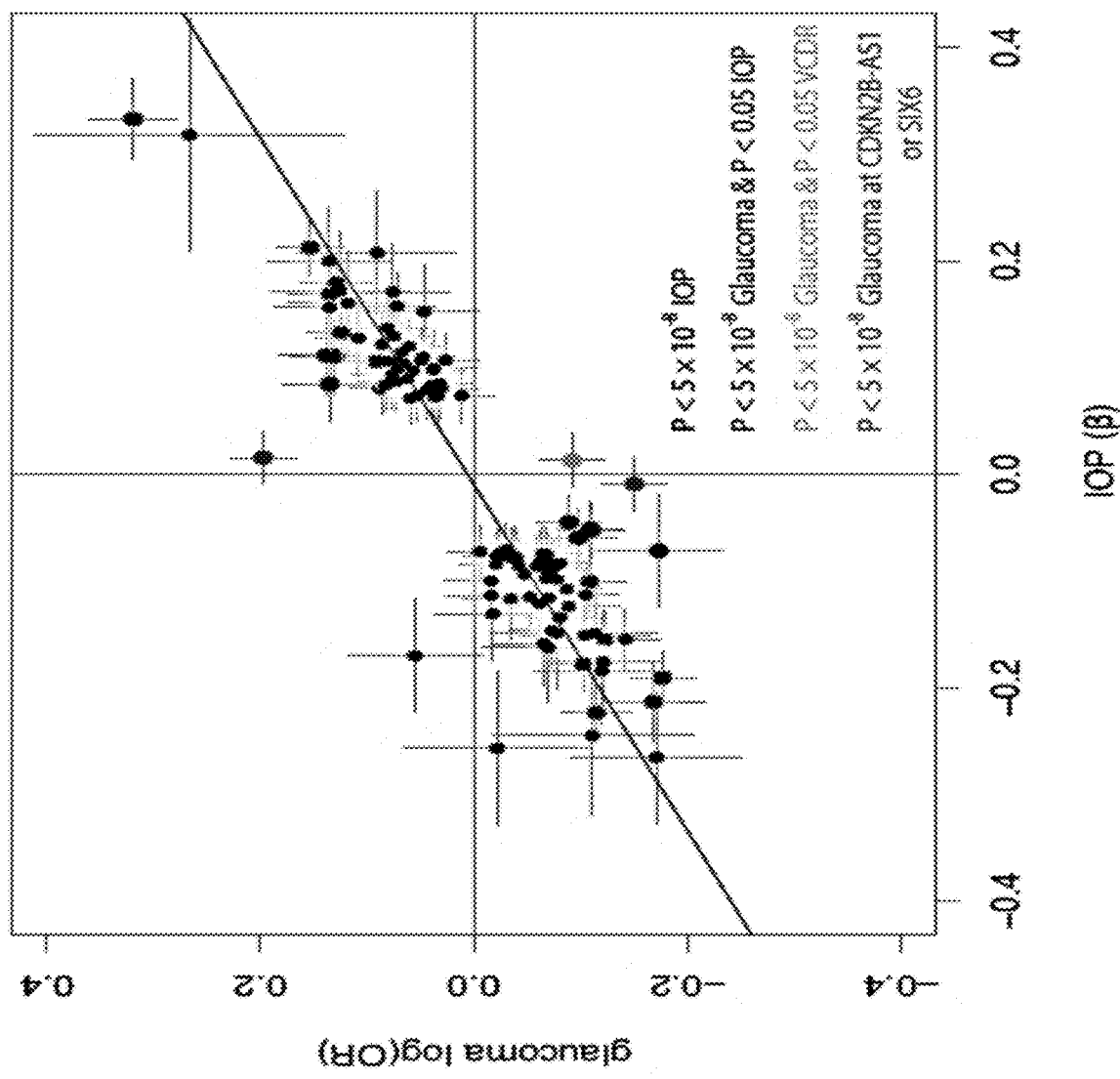

Of the 24 genome-wide significant loci for glaucoma, two (rs944801 within CDKN2B-AS1 and rs2093210 within the SIX6 locus; orange dots on FIG. 2b) are known to be associated with vertical cup-disc ratio (VCDR), an important optic nerve head parameter which is often used to define or diagnose glaucoma. An additional locus (rs61861119 near MYOF) was found to have no association with IOP but did have a suggestive level of evidence for association with VCDR (P=$1.6 \times 10^{-5}$; pink dot on FIG. 2b). The remaining 21 glaucoma loci are likely to influence disease development wholly or partly via IOP, with all showing at least P<0.01 (15 were genome-wide significant) for IOP (FIG. 2b and Table 11). Seven of the 21 also showed association with VCDR at P<0.01 (Table 11).

The relationship between IOP and glaucoma beyond the 24 SNPs which were genome-wide significantly associated with glaucoma was also examined. At the individual SNP level, of the 101 independent genome-wide significant IOP SNPs, 53 were significantly associated with glaucoma after Bonferroni correction (P<0.05/101=0.000495). The Pearson's correlation coefficient between IOP effect size and the glaucoma log odds ratio was 0.93 (P<0.001; FIG. 2b). Using bivariate LD score regression, we estimated the genome-wide genetic correlation between IOP and glaucoma to be 0.71 (SE=0.04) (Bulik-Sullivan, B. et al. An atlas of genetic correlations across human diseases and traits. *Nat. Genet.* 47, 1236-1241 (2015).

We also undertook a series of gene-based and pathway-based analyses for IOP and glaucoma. An additional 22 independent genes associated with IOP were identified through FastBAT gene-based tests (Bakshi, A. et al. Fast set-based association analysis using summary data from GWAS identifies novel gene loci for human complex traits. *Sci. Rep.* 6, 32894 (2016)). Of these 22 genes, four were associated with glaucoma following Bonferroni correction for 22 genes (P<0.00227), with an additional seven achieving P<0.05. In MAGMA pathway analysis (de Leeuw, C. A., Mooij, J. M., Heskes, T. & Posthuma, D. MAGMA: generalized gene-set analysis of GWAS data. *PLoS Comput. Biol.* 11, e1004219 (2015)) 11 Gene Ontology (GO) annotations were significantly associated with IOP, including extracellular matrix, collagen and vascular development. Among the 11 pathways highlighted by the IOP analysis, 9 showed at least P<0.05 in pathway analysis in the glaucoma samples, with the strongest GO annotation result for vascular development (P=0.0015). Seven pathways were significant in our DEPICT analysis of IOP (Pers, T. H. et al. Biological interpretation of genome-wide association studies using predicted gene functions. *Nat. Commun.* 6, 5890 (2015)).

The most significant IOP pathways were positive regulation of locomotion, cell motility and cell migration. These pathways were also significant in glaucoma (P=0.0021 to 0.0025).

Next, we tested whether the IOP loci could be used to predict POAG in the ANZRAG cohort. Allele scores were derived based on the 101 genome-wide significant primary IOP SNPs identified in this study (see the Methods section for inclusion criteria), as well as two loci with established associations with optic nerve head morphology (CDKN2B-AS1 and SIX6). These were tested in an independent dataset comprising 1,734 Australians of European ancestry with advanced POAG and 2,938 controls. Relative to a base model without the allelic scores, the scores were strongly associated with POAG status ($P<2\times10^{-16}$, Nagelkerke $R^2$=7.7%, AUC=0.65 [95% CI: 0.63-0.66]). Fitting only the IOP and only the VCDR SNPs in the allele score reduced the Nagelkerke $R^2$ to 5.4% and 2.7%, respectively. Individuals in the top 5%, 10%, and 20% of the allele scores were at significantly ($P<0.0001$) increased risk of POAG relative to the bottom 5%, 10%, and 20%, respectively (OR=7.8, 5.6, and 4.2, respectively).

We sought to characterize the expression profile of genes at the novel IOP loci that were also associated with glaucoma across a range of human ocular tissues (corneal epithelium, corneal stroma, corneal endothelium, trabecular meshwork, ciliary body pigmented epithelium, neurosensory retina, optic nerve head and the optic nerve). Expression of newly-associated genes was more highly enriched ($P=6.1\times10^{-59}$, Wilcoxon rank sum test for novel genes versus all other genes) in the trabecular meshwork compared to other ocular tissues. We then computed the ranks of the novel genes amongst all genes for each tissue and found that four of the other seven tissues (ciliary body pigmented epithelium, corneal stroma, optic nerve head and the optic nerve) were not significantly different, in terms of enrichment, compared to trabecular meshwork ($P>0.05$ for each pairwise comparison, Wilcoxon rank sum test, similar tissues). For the other three tissue types (neurosensory retina, corneal epithelium, corneal endothelium), the degree of enrichment was less than that seen in trabecular meshwork ($P<0.05$ for each pairwise comparison, Wilcoxon rank sum test). Finally, using FANTOM5 Cap Analysis of Gene Expression data, we found evidence of correlation between enhancers harbouring associated SNPs and the promoters of nine genes, including PTPN1, BCLAF1 and GAS7 in stromal and eye tissues, which is noteworthy given that hypoplasia of the anterior iris stroma is the most common iris defect associated with developmental glaucoma, and that these genes may act in a similar, albeit subclinical, manner.

Many of the loci we identified are associated with other eye conditions. Loss-of-function variants in LTBP2 have been found to cause primary congenital glaucoma (PCG); we now report that common variants at this locus influence IOP in the general population. Similarly, rare loss-of-function variants in TEK have been associated with PCG, and we identified common IOP-influencing variants in genes encoding the two known TEK ligands (ANGPT1; ANGPT2), as well as a third related protein (ANGPTL2).

Anterior segment dysgenesis, iris abnormalities, nanophthalmos, and microcornea are known causes of secondary glaucoma. Interestingly, four genes influencing the variation of IOP in the general population have been associated with anterior segment dysgenesis or other abnormalities of the iris, lens or cornea: FOXC1 with ocular anterior segment dysgenesis; TRAF3IP1 with iris furrows; MFRP with nanophthalmos; and ADAMTS18 with microcornea, myopic chorioretinal atrophy and telecanthus. Loss-of-function variants in LMX1B lead to nail-patella syndrome; common variants at this locus are now definitively associated with both POAG and IOP. Interestingly three loci (PLEKHA7; FERMT2; GLIS3) have been previously associated with PACG, and we have now implicated these regions with IOP, with two of them (PLEKHA7; FEMT2) also showing association with POAG. It is acknowledged that UKBB participants were not subjected to detailed clinical examination of their ocular anterior segment, hence some associations with IOP or POAG could be at least in part related to undiagnosed narrow drainage angles or subtle variations of ocular development.

Although the Australian glaucoma samples used were confirmed POAG cases, a limitation of the UKBB glaucoma cases was that only a small subset had documented disease subtype. Nevertheless, the proportion of non-POAG glaucoma cases in UKBB would be expected to be small. Applanation-based methods for IOP measurement are influenced by corneal biomechanical properties, such as corneal thickness and hysteresis. A strength of our work is the large sample size for standardised IOP measurement, with corneal compensation data available for approximately three-quarters of the dataset (corneal compensated IOP data was available for UKBB samples but not for IGGC samples). SNPs more strongly associated with corneal hysteresis than with IOP were excluded and this allowed us to identify a set of SNPs that have greater relevance to glaucoma development, rather than spuriously influencing IOP measurement.

In conclusion, we leveraged large sample sets from the UKBB and the IGGC to dramatically expand the number of genomic regions associated with IOP. We identified 101 statistically independent SNPs for IOP and found that 53 of them were associated with glaucoma. This work highlights the high genetic correlation between IOP and glaucoma. A number of previously implicated (extracellular matrix and collagen), and novel (vascular development and cell migration) pathways were associated with both IOP and glaucoma. Finally, an allele score based on the IOP loci and loci influencing optic nerve head morphology was able to enhance risk stratification.

URLs:
BOLT-LMM: https://data.broadinstitute.org/alkesgroup/BOLT-LMM/
DEPICT: https://data.broadinstitute.org/mpg/depict/index.html
Drug Gene Interaction Database: http://dgidb.genome.wustl.edu/
EdgeR bioconductor package: https://bioconductor.org/packages/release/bioc/html/edgeR.html
FANTOM5 data: http://enhancer.binfku.dk/GCTA
software: http://cnsgenomics.com/software/gcta/Haplotype
Reference Consortium: http://www.haplotype-reference-consortium.org/
International Glaucoma Genetic Consortium dataset: https://goo.gl/73qHqk
HTseq-count v0.6.0 software: https://pypi.python.org/pypi/HTSeq
LOCUSZOOM: http://locuszoom.sph.umich.edu/
LD-hub database: http://ldsc.broadinstitute.org/
MAGMA: https://ctg.cncr.nl/software/magma
METAL software: http://csg.sph.umich.edu/abecasis/Metal/
PLINK software: http://www.cog-genomics.org/plink2

TopHat v2.1.1 software: https://ccb.jhu.edu/software/tophat/index.shtml

UK Biobank: http://www.ukbiobank.ac.uk/

Methods:

Analysis of UK Biobank (UKBB) Data:

For a complete description of the UKKB genotype curation, please see the report as provided in Bycroft, C. et al. Genome-wide genetic data on ~500,000 UK Biobank participants. (2017). doi:10.1101/166298. All participants provided informed written consent, the study was approved by the National Research Ethics Service Committee North West—Haydock, and all study procedures were performed in accordance with the World Medical Association Declaration of Helsinki ethical principles for medical research. In brief, approximately 488,000 participants were genotyped on custom-designed Affymetrix UK BiLEVE Axiom or UK Biobank Axiom arrays (Affymetrix Santa Clara, USA), which produced a combined total of 805,426 markers in the released data. Following standard quality control (QC) the dataset was phased and ~96M genotypes were imputed using Haplotype Reference Consortium (HRC; see URLs) and UK10K haplotype resources (Bycroft, C. et al. Genome-wide genetic data on ~500,000 UK Biobank participants. (2017). doi:10.1101/166298; McCarthy, S. et al. A reference panel of 64,976 haplotypes for genotype imputation. *Nat. Genet.* 48, 1279-1283 (2016); UK10K Consortium et al. The UK10K project identifies rare variants in health and disease. *Nature* 526, 82-90 (2015). Due to the UKBB's reported QC issues with non-HRC SNPs, we retained only the ~40M HRC SNPs for analysis.

Among the 487,409 individuals who passed initial genotyping QC, 409,694 participants had white-British ancestry, based on self-reported ethnicity and genetic principal components. To maximise our effective sample size, we also included UKBB participants if their self-reported ancestry was not white-British (this includes a substantial number of individuals reporting their ancestry as "Irish" or "any other white background") but their first two genetic principal components fell within the region of those that are classified white-British in the N=409,694 set in Bycroft et al. (ibid.). Using these criteria, we identified 438,870 individuals for this study who are genetically similar to those of white-British ancestry.

Individuals were selected for analysis to ensure independence of the IOP and glaucoma arms of the study. Selection was based on the following: 1). glaucoma cases were selected, 2). individuals participating in the ocular examination (approximately a quarter of the UKBB cohort) were selected (with glaucoma cases and their relatives [$\hat{\pi}$>0.2)] omitted) and 3). individuals who self-reported having no eye disease were selected (controls were screened to be unrelated [$\hat{\pi}$>0.2]) for use as controls with the glaucoma cases. Among the 438,870 with suitable genetic data, we extracted 7,947 individuals with glaucoma; cases were those who either 1) had an ICD-10 diagnosis ("Primary Open Angle Glaucoma", "Other Glaucoma", "Glaucoma, unspecified", 2) responded "Glaucoma" to "Has a doctor told you that you have any of the following problems with your eyes?", 3) responded "Glaucoma" to the question "In the touch screen you selected that you have been told by a doctor that you have other serious illnesses or disabilities, could you now tell me what they are? (non-cancer illness)". Although this glaucoma definition is broad, ~80% of "glaucoma" cases amongst white British individuals are likely to meet diagnostic criteria for POAG. The number of individuals with ICD-10 POAG was over five times less, limiting the power of the study. A subset (127,468) of UKBB participants took part in the ocular examination, which included IOP measurements using the Ocular Response Analyzer non-contact tonometer. Our primary IOP analysis was based on corneal-compensated IOP (IOPcc) measurements because these are expected to be less affected by corneal factors than Goldmann-correlated IOP measures. The mean IOPcc for each participant was calculated, with measurements <5 or >60 mmHg set to missing. Mean corneal hysteresis and mean non-corneal-compensated (Goldmann-correlated) IOP were also derived and tested at loci of interest from the IOPcc analysis. 103,914 individuals with ocular examinations had both phenotype and genotype data available. Finally, controls for the glaucoma cases were selected based on a reply of "None" to "Has a doctor told you that you have any of the following problems with your eyes?" and no ocular examination.

Genotyping and Analysis of the Australian & New Zealand Registry of Advanced Glaucoma (ANZRAG) Cohort:

The clinical recruitment and characterisation of the ANZRAG cohort has been described previously. In this analysis a total of 3,071 POAG cases and 6,750 historic controls of European descent were used. Case and control samples were genotyped on Illumina Omni1M, OmniExpress or HumanCoreExome arrays (Illumina, San Diego, USA). This dataset involves three phases of POAG data collection, and hence, QC, imputation, and association analysis was conducted separately for each phase before combining the results in a meta-analysis. The first phase has 1,155 advanced POAG cases and 1,992 historic controls genotyped on Illumina Omni1M or OmniExpress arrays. In this phase the historic controls were obtained from 225 oesophageal cancer cases, 317 Barrett's esophagus cases and their 552 controls, as well as 303 inflammatory bowel diseases cases and their corresponding 595 control cohort. The second phase includes a further 579 advanced POAG cases genotyped on Illumina HumanCoreExome array and 946 controls selected from parents of twins previously genotyped on the same array. The third phase has 1,337 POAG cases genotyped on Illumina HumanCoreExome array and 3,812 controls selected from a study of endometriosis previously genotyped on the same array. There is strong female bias in the control set in phase three, but not in phases one and two (our allele score prediction work below uses only phases one and two).

QC was performed using PLINK (see URLs; Purcell, S. et al. PLINK: a tool set for whole-genome association and population-based linkage analyses. *Am. J. Hum. Genet.* 81, 559-575 (2007). Individuals with more than 3% missing genotypes, and SNPs with call rate less than 97%, minor allele frequency (MAF)<0.01, and Hardy-Weinberg equilibrium (HWE) P<0.0001 in controls or P<$5\times10^{-10}$ in cases were removed from the analysis. Identity by descent was determined based on autosomal markers in PLINK, and only one of each pair of individuals with relatedness ($\hat{\pi}$) of >0.2 was used in the analysis. PLINK was used to compute principal components for all participants and reference samples of known northern European ancestry (1000G British, CEU, Finland participants). Participants with PC1 or PC2 values>6 standard deviations from the mean of known Northern European ancestry group were excluded. All statistical tests throughout the manuscript were two-sided.

Phasing of the genotyped SNPs was conducted using ShapeIT (Delaneau, O., Marchini, J. & Zagury, J.-F. A linear complexity phasing method for thousands of genomes. *Nat. Methods* 9, 179-181 (2011)) and imputation was performed using Minimac3 through the Michigan Imputation Server (Das, S. et al. Next-generation genotype imputation service and methods. *Nat. Genet.* 48, 1284-1287 (2016) with the HRC as the reference panel (McCarthy, S. et al. A reference panel of 64,976 haplotypes for genotype imputation. *Nat. Genet.* 48, 1279-1283 (2016)). SNPs with imputation quality ($\hat{r}^2$)>0.3 and MAF>0.01 were used for analysis.

Association Testing: IOP IGGC

We obtained publicly available GWAS summary statistics from an IGGC study on IOP. 29,578 individuals had 1000G imputed GWAS data available, with IOP corrected for age and sex. The vast majority of IGGC sites used Goldmann-corrected TOP; these IOP measures do not account for corneal differences between individuals and in large samples an "IOP" analysis may identify loci that are primarily driven by corneal parameters.

Association Testing: IOP UKBB

Association analysis was performed using a linear mixed model framework to account for cryptic relatedness and population stratification in the UKBB samples using BOLT-LMM version 2.3 (see URLs; Loh, P.-R. et al. Efficient Bayesian mixed-model analysis increases association power in large cohorts. *Nat. Genet.* 47, 284-290 (2015)). We used a sparse set of 360,087 genotyped SNPs across the autosomes to estimate the Bayesian Gaussian mixture prior to characterising the random-effects genetic component. The infinitesimal model in BOLT-LMM was used to generate GWAS p-values. The IGGC and UKBB IOP results were combined using meta-analysis, implemented in METAL (2011 Mar. 25 release; see URLs; Willer, C. J. et al. Newly identified loci that influence lipid concentrations and risk of coronary artery disease. *Nat. Genet.* 40, 161-169 (2008)).

To identify statistically independent genome-wide significant SNPs, an initial list of SNPs with meta-analysis p-values<$5\times10^{-8}$ was pruned into discrete regions by LD clumping in PLINK v1.9 ($r^2$ threshold for clumping 0.1, physical distance threshold for clumping 2 megabases). This initial list of SNPs was then further explored for additional independent signals by conditioning the meta-analysis summary data using GCTA version 1.26 (see URLs). To calculate LD, a reference panel was constructed from 5,000 individuals randomly selected from the UKBB white British ancestry individuals. Imputed SNPs with a rsq>0.3 and MAF>0.001 were converted to best guess genotypes, and then cleaned for 3% missingness and HWE<$1\times10^{-6}$. Initially a given peak SNP was used to condition all SNPS within 2 megabases (—cojo-cond option). Where there were multiple SNP within 2 megabases of each other, they were analysed together using boundaries at least ±2 megabases from the furthest apart SNP. Following this, a SNP was deemed independent if its initial single SNP p-value was <$5\times10^{-8}$ and remained <$5\times10^{-8}$ following conditioning. Newly identified SNPs were iteratively added to the regional conditioning until no more SNPs had a p-value<$5\times10^{-8}$. As a final check the joint effect (—cojo-joint) of all putatively genome-wide significant SNPs was estimated, with any SNPs which then had joint p-values>$5\times10^{-8}$ discarded.

Association Testing: UK Biobank Glaucoma Case-Control Analysis

We assessed associations between SNPs and glaucoma status adjusted for sex and the first six principal components, under an additive genetic model using the dosage scores obtained from imputation. Association analysis was performed using PLINK version 2.0 (Purcell, S. et al. PLINK: a tool set for whole-genome association and population-based linkage analyses. *Am. J. Hum. Genet.* 81, 559-575 (2007). Identity by descent was determined based on autosomal markers in PLINK version 1.90b, and only one of each pair of individuals with $\hat{\pi}$>0.2 was used in the analysis.

We used mean $\chi^2$ and the univariate LD score regression approach to investigate presence of model or structural bias in the glaucoma GWAS data (Bulik-Sullivan, B. K. et al. L D Score regression distinguishes confounding from polygenicity in genome-wide association studies. *Nat. Genet.* 47, 291-295 (2015). An LD score intercept close to 1 in a univariate analysis indicates that there is no model misspecification and that other sources of bias such as population stratification and cryptic relatedness are not adversely affecting results.

Exclusion of Loci Based on Association with Corneal Parameters

All loci that were genome-wide significantly associated with IOP were tested for association with corneal hysteresis (hyst—a measure of viscous damping in the cornea that may affect the measurement of IOP). SNPs with a larger effect on hyst than on IOP are unlikely to be truly associated with IOP and hence we filtered SNPs with $P_{hyst}<P_{IOP}$ (SNPs with effects on various aspects of eye morphology of large effect, such as TMCO1, influenced both IOP and hyst and so we did not filter simply on $P_{hyst}$). Similarly, putative IOP loci were examined for previous association with central corneal thickness.

LD-Score Regression:

We applied univariate LD-score regression (see URLs; Bulik-Sullivan, B. K. et al. L D Score regression distinguishes confounding from polygenicity in genome-wide association studies. *Nat. Genet.* 47, 291-295 (2015)), to estimate the SNP-heritability of IOP and bivariate LD-score regression (Bulik-Sullivan, B. et al. An atlas of genetic correlations across human diseases and traits. *Nat. Genet.* 47, 1236-1241 (2015)) to estimate the genetic correlation between IOP and glaucoma.

Gene-Based Tests:

Gene-based tests were conducted using the fast and flexible set-Based Association Test (fastBAT), a gene-based approach that calculates the association p-values for a set of SNPs (within ±50 kb of a gene for this study) using GWAS summary data while accounting for LD between SNPs.[21] Only loci distinct from those found in the per-SNP tests (>1 megabase away) were tested. fastBAT was applied to the IOP meta-analysis results, with a significance threshold of $2\times10^{-6}$ (0.05/24,654 genes tested). Genes exceeding this threshold were then tested for association with glaucoma (ANZRAG+UKBB) using fastBAT.

Pathway-Based Tests:

Pathway-based tests were conducted on the IOP meta-analysis results using MAGMA and DEPICT (see URLs; Pers, T. H. et al. Biological interpretation of genome-wide association studies using predicted gene functions. *Nat. Commun.* 6, 5890 (2015); Andersson, R. et al. An atlas of active enhancers across human cell types and tissues. *Nature* 507, 455-461 (2014)). We opted to use both approaches because they use different pathway databases as well as a different method for annotating SNPs to genes. In MAGMA, Z-scores from a gene-based step were combined based on 5,917 pre-specified Gene Ontology gene sets. DEPICT is an integrative tool that, for each gene, uses the likelihood of membership in each gene set based on the co-regulation of gene expression data, and tests whether any of the 14,462 preconstituted gene sets are significantly enriched for genes in the trait-associated loci. SNPs exceeding P<$5\times10^{-8}$ were used to define trait-associated loci in a pathway analysis in DEPICT. Pathways exceeding P<0.05/5917 (MAGMA) or P<0.05/14463 (DEPICT) were then tested using the same approach in glaucoma (ANZRAG+UKBB).

Allele Scores:

We used the allele score approach to investigate whether the genome-wide significant IOP loci identified in this study, as well as the two previously known VCDR loci with established association with POAG (rs2157719 within the CDKN2B-AS1 locus and rs8015152 within the SIX6 locus), can significantly predict risk of glaucoma. We used only statistically independent SNPs to create the profile scores and excluded the known published central corneal thickness loci as well as corneal hysteresis SNPs whose P values in this study were lower than the IOP P values. This was to rule out those SNPs that may not truly affect IOP but have been detected as IOP loci through their effects on corneal hysteresis. The SNPs passing the above criteria were used to score individuals in a target cohort, a subset of the ANZRAG data with advanced POAG (1,734 cases and 2,938 controls). Our ANZRAG dataset was non-overlapping with the cohort used to identify the IOP SNPs (and their estimated effect sizes). The score for each individual in ANZRAG was calculated by summing the number of risk alleles weighted by their effect sizes obtained from the IOP and VCDR analyses. As IOP and VCDR are measured on different scales, we benchmarked their relative weights (in terms of their effect on glaucoma) using the well-established large effect associations with IOP (TMCO1 rs10918274—estimated to increase IOP by 0.33 units and in a POAG meta-analysis, to increase risk 1.39 fold) and with VCDR (CDKN2B-AS1 rs2157719—estimated to increase VCDR by 0.13 and POAG 1.44 fold). Based on these benchmarks, each 1 unit increase in IOP leads to a 0.998 log(OR) increase (log(1.39)/0.33) in POAG risk. Similarly, each 1 unit increase in VCDR leads to a 28.049 log(OR) increase (log(1.44)/0.13) in POAG risk. Hence, prior to combining the IOP and VCDR allele scores for analysis, we multiplied the VCDR risk score by 28.049/0.998 to place it on an equivalent scale to IOP.

To estimate the contribution of the profile scores with the POAG status in the ANZRAG target cohort, we first performed a logistic regression with sex and the first four principal components used as covariates (base model). We then added the profile scores into the logistic model and computed the increase in the Nagelkerke's pseudo $R^2$ from the logistic regression over and above the base model (Nagelkerke's pseudo $R^2$ is a measure of the goodness of fit in the prediction model, analogous to phenotypic variance explained in a linear regression). We also compared the POAG risk for the top versus bottom 5%, 10% (decile), and 20% of the profile score distribution.

Drug Pathway:

The Drug Gene Interaction Database (DGIdb 3.0 release; see URLs) was used to identify compounds that act on genes at each locus and could be repurposed in the treatment of glaucoma.

Gene Target Prediction:

FANTOM5 data representing enhancer-promoter Cap Analysis of Gene Expression (CAGE) expression correlation from all cell types were downloaded and processed (see URLs; Andersson, R. et al. An atlas of active enhancers across human cell types and tissues. Nature 507, 455-461 (2014)). Enhancers active in eye and stromal tissues were tested for overlap with SNPs correlated with lead SNPs ($r^2>0.8$ in 1000 Genomes EUR populations). Genes for which CAGE promoter expression signals were correlated with enhancers were selected as potential target genes.

Ocular Expression Analysis:

The gene expression profiles of all genes within IOP-associated loci were examined in relevant ocular tissues. Data were available from a total of 16 donor eyes from 16 individuals. RNA was extracted from 48 samples of distinct ocular tissue (corneal epithelium, corneal stroma, corneal endothelium, trabecular meshwork, ciliary body pigmented epithelium, neurosensory retina, optic nerve head and the optic nerve) and sequenced using Illumina NextSeq 500 (Catalog #FC-404-2005, San Diego, USA) with Bioo Scientific NEXTflex rapid directional mRNA-seq Kit (Catalog #5138-10, Austin, Texas, USA). We obtained an average of 56 million 75 bp paired-end reads per sample. Following QC and trimming these were mapped to the reference human genome (hg19) using TopHat v2.1.1 and HTseq-count v0.6.0 (see URLs; Kim, D. et al. TopHat2: accurate alignment of transcriptomes in the presence of insertions, deletions and gene fusions. Genome Biol. 14, R36 (2013); Anders, S., Pyl, P. T. & Huber, W. HTSeq—a Python framework to work with high-throughput sequencing data. Bioinformatics 31, 166-169 (2015)). Normalized counts per million (CPM) data were calculated using trimmed mean of M-values (TMM) normalization method using edgeR v.3.10.2 (see URLs; McCarthy, D. J., Chen, Y. & Smyth, G. K. Differential expression analysis of multifactor RNA-Seq experiments with respect to biological variation. Nucleic Acids Res. 40, 4288-4297 (2012)). Transcripts from a total of 21,962 RefSeq protein-coding genes were captured and mapped. We had 94.5% of the reads mapped to the human genome after QC filtering. The mean TMM value across all available samples for each gene in each tissue was calculated and to test whether there was enrichment for genes at the novel loci associated with glaucoma in each tissue we used a Wilcoxon rank sum test for novel genes versus all other genes. We then computed the ranks of the novel genes amongst all genes for each tissue and compared each tissue in turn to the tissue showing most enrichment (Wilcoxon rank sum test).

Example 2—Combining Information Across Glaucoma and its Endophenotypes Improves Risk Profiling Background Glaucoma is the leading cause of irreversible blindness worldwide, but vision loss which is asymptomatic in the early stages is preventable with treatment. Vertical cup-disc ratio (VCDR) and intraocular pressure (IOP) are major endophenotypes of glaucoma, and IOP lowering is the only currently proven treatment.

Methods:

We characterized the optic nerve head in 67,040 UK Biobank participants and performed a genome-wide association study (GWAS) for VCDR. These data were then combined with IOP and glaucoma in a multivariate model to identify novel glaucoma genes. Newly identified genes were validated in two independent glaucoma case-control cohorts, and the multivariate model was then used to construct a polygenic risk score (PRS). The utility of the PRS was evaluated in case-control and prospective settings.

Results:

The GWAS of VCDR identified 76 statistically independent loci of which 48 had not previously been associated with this trait. We show that although IOP and VCDR are both highly genetically correlated with glaucoma risk, there is only weak correlation between VCDR and IOP. We leverage the genetic correlation in a multivariate statistical model to identify 50 novel loci for glaucoma. We then validate the loci in an independent Australian glaucoma case-control cohort, with good concordance between the odds ratios estimated in our multivariate model and the odds ratios in our independent samples. In 1,734 advanced glaucoma cases and 2,938 controls, the risk of glaucoma was 15 fold greater (OR=14.9; 95% CI 10.7-20.9) in the top decile of the PRS relative to the bottom decile, and people on average were diagnosed 7 years earlier. In addition, PRS showed strong association with important clinical decisions and outcomes. The PRS predicted the need for surgery in advanced glaucoma (P=2.75×10$^{-5}$) and progressive loss of nerve fiber layer in early manifest glaucoma (P=0.003).

Conclusions:

We derive a PRS using weighted data on glaucoma, IOP and VCDR and show it is associated with: 1) risk of advanced glaucoma; 2) improved prediction of glaucoma status beyond traditional risk factors; 3) earlier age of diagnosis; 4) likelihood of glaucoma surgery; and 5) the likelihood of rapid progression in early stage disease.

Introduction

Although recent genome-wide association studies (GWAS) have identified a vast number of genetic associations, the effect of each individual genetic variant is typically small, and the clinical utility of this new information has generally been limited. Nonetheless, the earliest clinical translation is likely to eventuate for diseases where the aggregate effects of many genes in a polygenic risk score (PRS) is relatively large, and where clinical decision making can be modified by early detection or improved prognostication. Primary open angle glaucoma (POAG) presents an ideal case, whereby progressive visual loss and blindness can typically be prevented by timely intervention, and a strong genetic basis has been well-established.

Glaucoma is a leading cause of irreversible blindness worldwide, and in Western countries POAG contributes the greatest disease burden, with a population prevalence of approximately 3% in people over 40 years of age. POAG is asymptomatic in the early stages, and currently approximately half of all cases in the community are undiagnosed. Early detection is of paramount importance as existing treatments are unable to reverse optic nerve damage, and late presentation is a major risk factor for advanced vision loss. Screening strategies for glaucoma such as measuring intraocular pressure (IOP) have lacked sensitivity and specificity and as yet have not proved to be cost-effective, emphasizing the need for more refined approaches, which capitalize on the fact that glaucoma is one of the most heritable human diseases.

In this study, we characterized the optic nerve head in 67,040 UK Biobank participants, enabling by far the largest genome-wide association study on optic nerve morphology—vertical cup-disc ratio (VCDR), adjusted for vertical disc diameter (VDD). We then incorporated additional genetic data on IOP and glaucoma disease status to i) identify new risk loci for glaucoma, and ii) generate a PRS. We examined the impact of newly implicated genes in independent case-control cohorts from the United Kingdom and Australia. We then evaluated the utility of our PRS for predicting glaucoma risk, and a wide range of clinical outcomes including prospective analysis of glaucoma progression.

Methods:

Study Design and Overview

Figure 3:
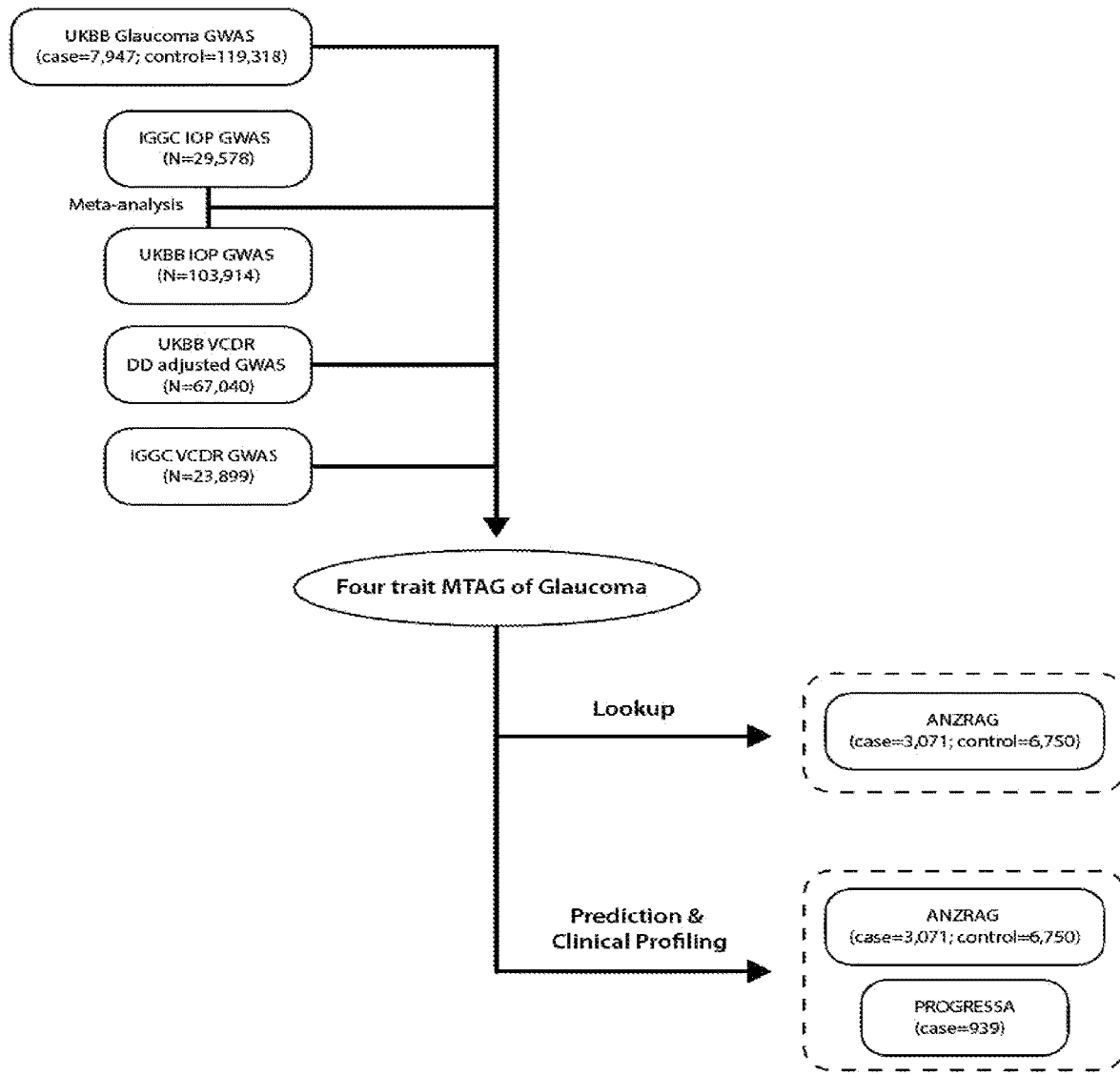
FIG. 3 shows the study design. The multi-trait analysis of GWAS (MTAG) algorithm was applied to four datasets (glaucoma case-control GWAS from the UK Biobank (UKBB); GWAS meta-analysis of IOP from the International Glaucoma Genetics Consortium (IGGC) and the UKBB; Vertical cup-disc ratio (VCDR) GWAS data that was either adjusted for vertical disc diameter (VDD) in the UKBB dataset; or not adjusted for VDD in the IGGC. VCDR adjusted for VDD was not available in IGGC and hence rather than meta-analyse two different traits, we included both as separate traits in MTAG, with MTAG modelling the incomplete correlation between traits. Novel variants ($P<5\times10-8$) identified through this analysis were then looked up in ANZRAG. The clinical significance of the PRS derived from the MTAG analysis was investigated in advanced cases (ANZRAG) and a prospective clinical cohort (PROGRESSA).

Our overall study design is illustrated in FIG. 3. We first conducted a GWAS on glaucoma (case-control) and on key endophenotypes for glaucoma: VCDR and IOP. These data were then combined using multi-trait analysis of GWAS (MTAG) (Turley P, Walters R K, Maghzian O, et al. Multi-trait analysis of genome-wide association summary statistics using MTAG. *Nat Genet* 2018; 50(2): 229-37), a method for leveraging multiple genetically correlated traits to maximize power to identify new loci and improve genetic risk prediction. Specifically, MTAG outputs glaucoma specific effect size estimates for SNPs across the genome. Newly associated loci (P<5×10$^{-8}$) were validated in two independent cohorts with well-defined POAG. All SNPs were then considered for inclusion in a PRS. The clinical significance of the PRS was investigated in advanced glaucoma cases and a separate prospective clinical cohort. The predictive ability of the PRS was also explored in other datasets; however, to ensure no overlap with discovery samples the PRS was re-derived in independent cohorts.

The UKBB is a population-based study of 500,000 people living in the UK. In brief, approximately 488,000 participants were genotyped on custom-designed Affymetrix UK BiLEVE Axiom or UK Biobank Axiom arrays (Affymetrix Santa Clara, USA), to produce a combined total of 805,426 markers per participant in the released data. After standard quality control (QC) procedures, the dataset was phased and ~96M genotypes were imputed using Haplotype Reference Consortium (HRC) and UK10K haplotype resources. Using these criteria, we identified 438,870 individuals for this study who are genetically similar to those of white-British ancestry. We measured the VCDR and the vertical disc diameter (VDD) in subjects who had gradable retinal images (67,040 participants following exclusions) and undertook a GWAS to identify novel genetic variants influencing optic nerve morphology. This was combined with GWAS data from the UKBB relating to corneal-compensated IOP (103, 914 participants) and glaucoma (7,947 cases and 119,318 controls). We also used publicly available VCDR and IOP GWAS summary results for individuals of European descent from the International Glaucoma Genetic Consortium study (IGGC; $N_{VCDR}$=23,899, $N_{IOP}$=29,578).

The Australian & New Zealand Registry of Advanced Glaucoma (ANZRAG) Cohort, comprise a total of 3,071 POAG cases, who were compared to 6,750 historic controls of European descent. For sub-analyses restricted to advanced glaucoma, there are 1,734 advanced glaucoma cases and 2,938 controls. Case and control samples were genotyped on Illumina Omni1M, OmniExpress, or Human-CoreExome arrays (Illumina, San Diego, CA, USA).

The Blue Mountains Eye Study (BMES) is a population-based cohort study investigating the etiology of common ocular diseases among suburban residents aged 49 years or older, living in the Blue Mountains region, west of Sydney, Australia. Participants were genotyped on the Illumina Human 610 Quad Array. 74 POAG cases and 1,721 controls of European descent with genotype data, both baseline IOP and VCDR measurements were included in this study.

The "Predicting Risk Of Glaucoma: RElevant SNPs with Strong Association" (PROGRESSA) study is a prospective longitudinal study of the course, risk factors and genetic associations for early stage disease glaucoma. Patients with confirmed early manifest open angle glaucoma (EMG) on visual field testing were consecutively recruited from ophthalmology clinics in South Australia. Individuals underwent six-monthly evaluation of IOP, optic disc assessment, retinal nerve fibre layer (RNFL) analysis by optical coherence tomography (OCT), and achromatic Humphrey visual field perimetry. Longitudinal data were used from all visits since baseline presentation; participants were followed for three to five years. The rate of RNFL change was measured between the baseline OCT and the most recent OCT in most-affected RNFL quadrant of the most-affected eye. Apart from clinical family history, the treating clinicians were unaware of the patient's genetic risk for glaucoma and the polygenic risk score was not available to guide any treatment decisions. Participants were genotyped on HumanCoreExome arrays (Illumina, San Diego, CA, USA).

POAG in the ANZRAG, BMES, and PROGRESSA cohorts was defined in accordance with the consensus statement from the World Glaucoma Association.

Statistical Analysis

For the VCDR (adjusted for VDD) and IOP GWAS in UKBB, we used linear mixed models to account for cryptic relatedness and population stratification using BOLT-LMM version 2.3 (Loh P-R, Tucker G, Bulik-Sullivan B K, et al. Efficient Bayesian mixed-model analysis increases association power in large cohorts. Nat Genet 2015; 47(3):284-90). We combined UKBB and IGGC IOP GWAS results using meta-analysis (METAL, 2011 Mar. 25 release) (Willer C J, Li Y, Abecasis G R. METAL: fast and efficient meta-analysis of genomewide association scans. Bioinformatics 2010; 26(17):2190-1). For glaucoma GWAS in UKBB, we removed relatives and used PLINK (version 2.0) for the association analysis (Purcell S, Neale B, Todd-Brown K, et al. PLINK: a tool set for whole-genome association and population-based linkage analyses. Am J Hum Genet 2007; 81(3):559-75). We conducted four trait MTAG using GWAS summary statistics from UKBB glaucoma, UKBB VCDR (adjusted for VDD), IGGC VCDR and the IOP meta-analysis (Turley P, Walters R K, Maghzian O, et al. Multi-trait analysis of genome-wide association summary statistics using MTAG. Nat Genet 2018; 50(2):229-37). GCTA-COJO was used to identify independent genome-wide significant SNPs (Yang J, Ferreira T, Morris A P, et al. Conditional and joint multiple-SNP analysis of GWAS summary statistics identifies additional variants influencing complex traits. Nat Genet 2012; 44(4):369-75, S1-3).

Prediction was based on the estimated glaucoma odds ratios from our four trait MTAG analysis. To construct our PRS, we first performed LD-clumping. We then applied a range of P value thresholds ($5 \times 10^{-8}$, $1 \times 10^{-5}$, 0.001, 0.05, 1) in our first prediction (advanced glaucoma cases from ANZRAG) (Purcell S, Neale B, Todd-Brown K, et al. PLINK: a tool set for whole-genome association and population-based linkage analyses. Am J Hum Genet 2007; 81(3):559-75). For the subsequent predictions into other target sets (PROGRESSA, BMES, UKBB glaucoma), we only applied the threshold with greatest predictive value in ANZRAG to reduce multiple testing (i.e. for all the predictions other than ANZRAG only the 0.001 threshold was applied, rather than the five initially screened thresholds). LD clumping was based on the overlap SNPs between training and target datasets. There was no sample overlap between each of the training and target datasets. Bivariate LD score regression was used to estimate the genetic correlation between pairs of traits (Bulik-Sullivan B, Finucane H K, Anttila V, et al. An atlas of genetic correlations across human diseases and traits. Nat Genet 2015; 47(11):1236-41). R software (R Core Team. R: A Language and Environment for Statistical Computing [Internet]. 2017; Available from: https://www.R-project.org/) and the "pROC" package (Robin X, Turck N, Hainard A, et al. pROC: an open-source package for R and S+ to analyze and compare ROC curves. BMC Bioinformatics. 2011; 12:77) was used to calculate the area under the curve (AUC).

Results

Discovery of Genetic Variants Influencing Optic Nerve Morphology

Figure 4A:
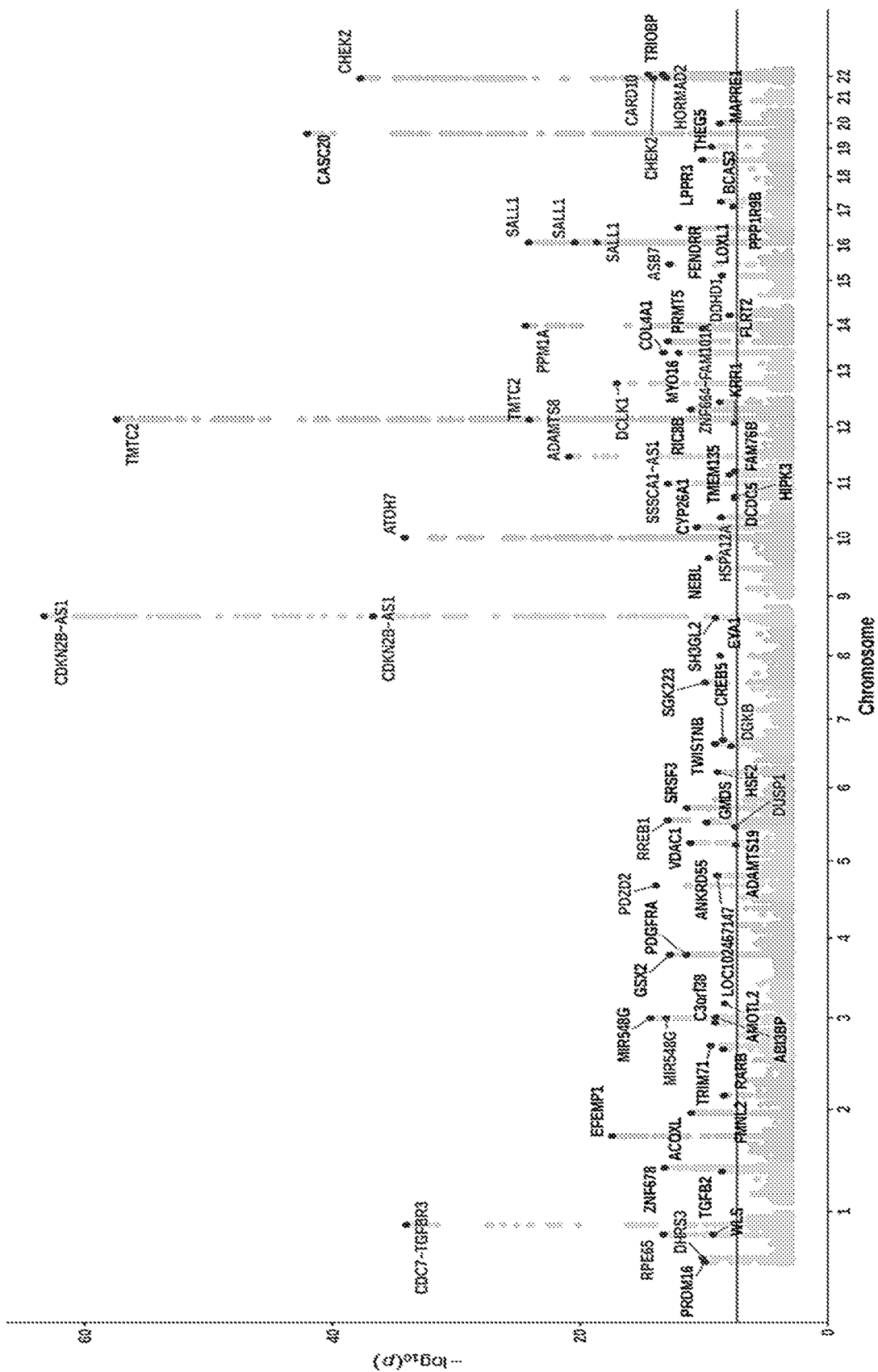
FIG. 4 shows Manhattan plot of genome-wide association studies. Panel A shows the GWAS of UKBB VCDR (VDD adjusted). Panel B shows the MTAG result of glaucoma, IOP and VDD adjusted or unadjusted VCDR. Novel SNPs are highlighted in red dots with black text of the nearest gene names. Known SNPs are only highlighted in purple dots. With the nearest gene names in purple text.
Figure 10:
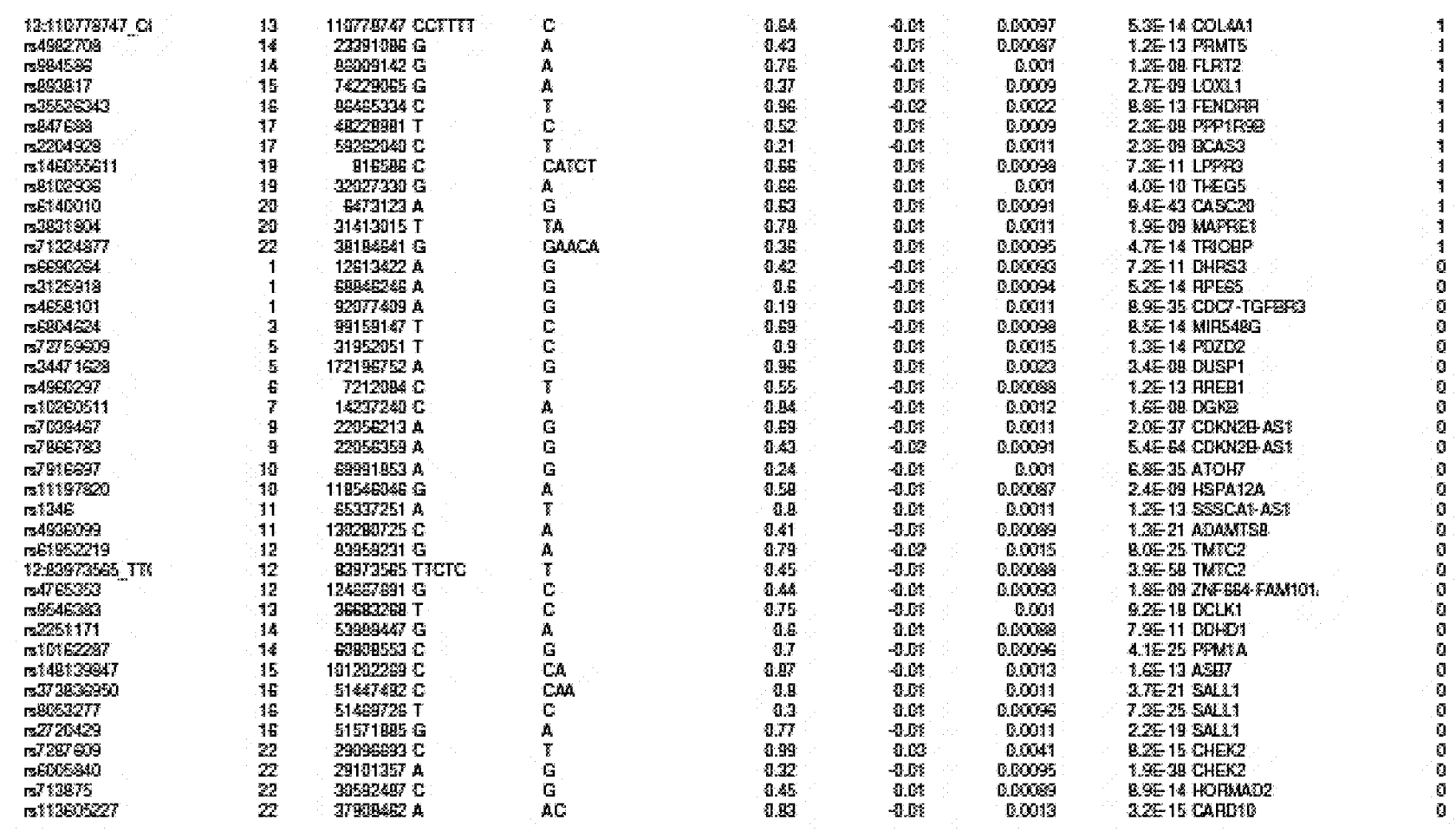

GWAS of VCDR (adjusted for VDD) identified 76 statistically independent loci of which 48 had not previously been associated with VCDR (FIG. 4A, and FIG. 10).

Using LD score regression, we found no evidence for genomic inflation (intercept=1.04, SE=0.01). The genetic correlation between VCDR (adjusted for VDD) and glaucoma was 0.50 (SE=0.05); the correlation in effect sizes estimates at the 76 SNPs was 0.6 ($P=9.0 \times 10^{-9}$, FIG. 5). As previously reported, the genetic correlation between IOP and glaucoma is high (0.71), but the genetic correlation between VCDR (adjusted for VDD) and IOP was substantially lower (0.22, SE=0.03).

Discovery of Glaucoma Loci Via Multivariate Analysis

Figure 4B:
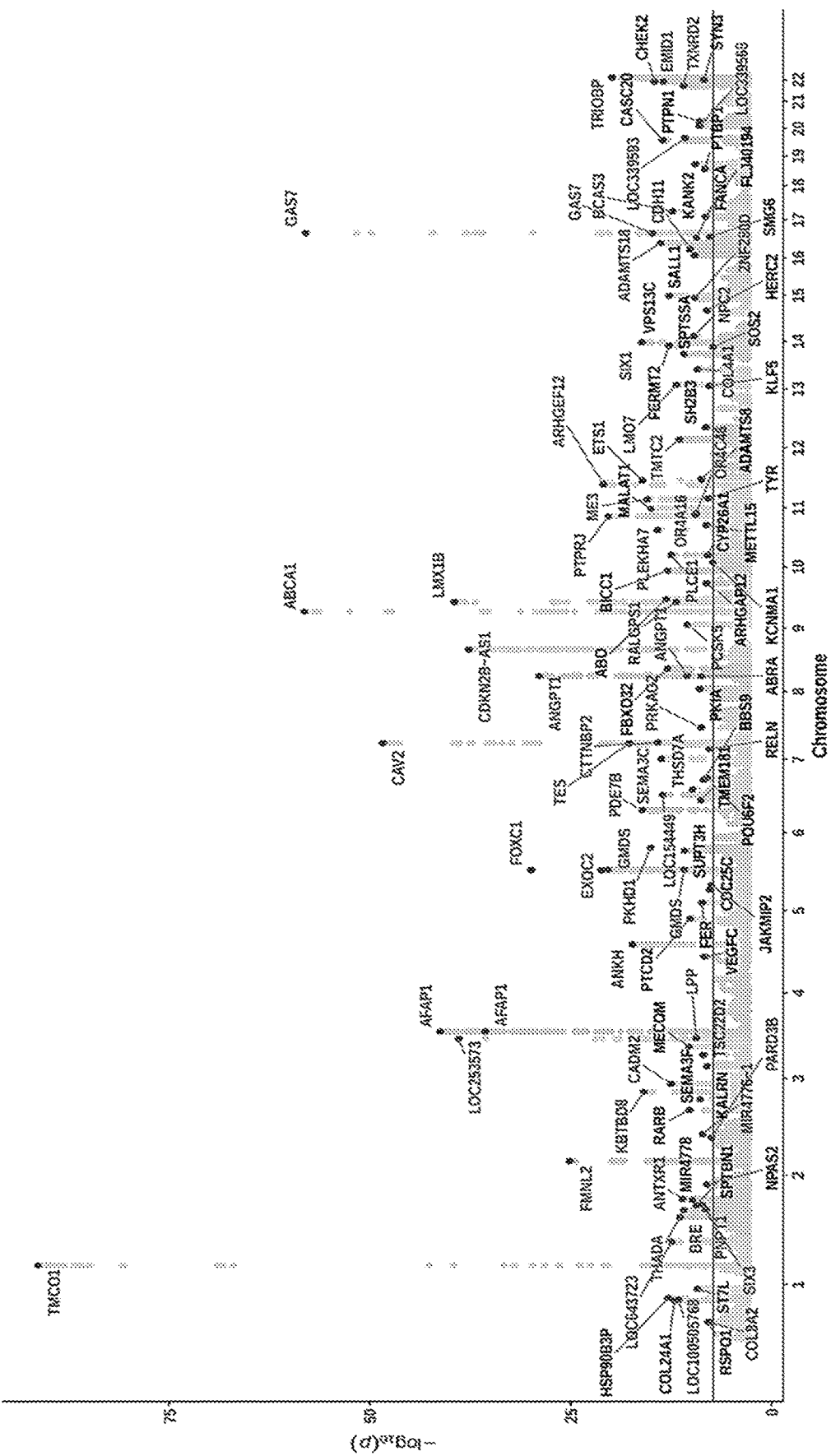

Given the high correlation between glaucoma and its endophenotypes, we then used a multivariate GWAS using MTAG to identify 114 loci for glaucoma—this includes all previously published glaucoma loci plus 50 novel SNPs (FIG. 4B, and FIG. 11 and FIG. 12).

Figure 5:
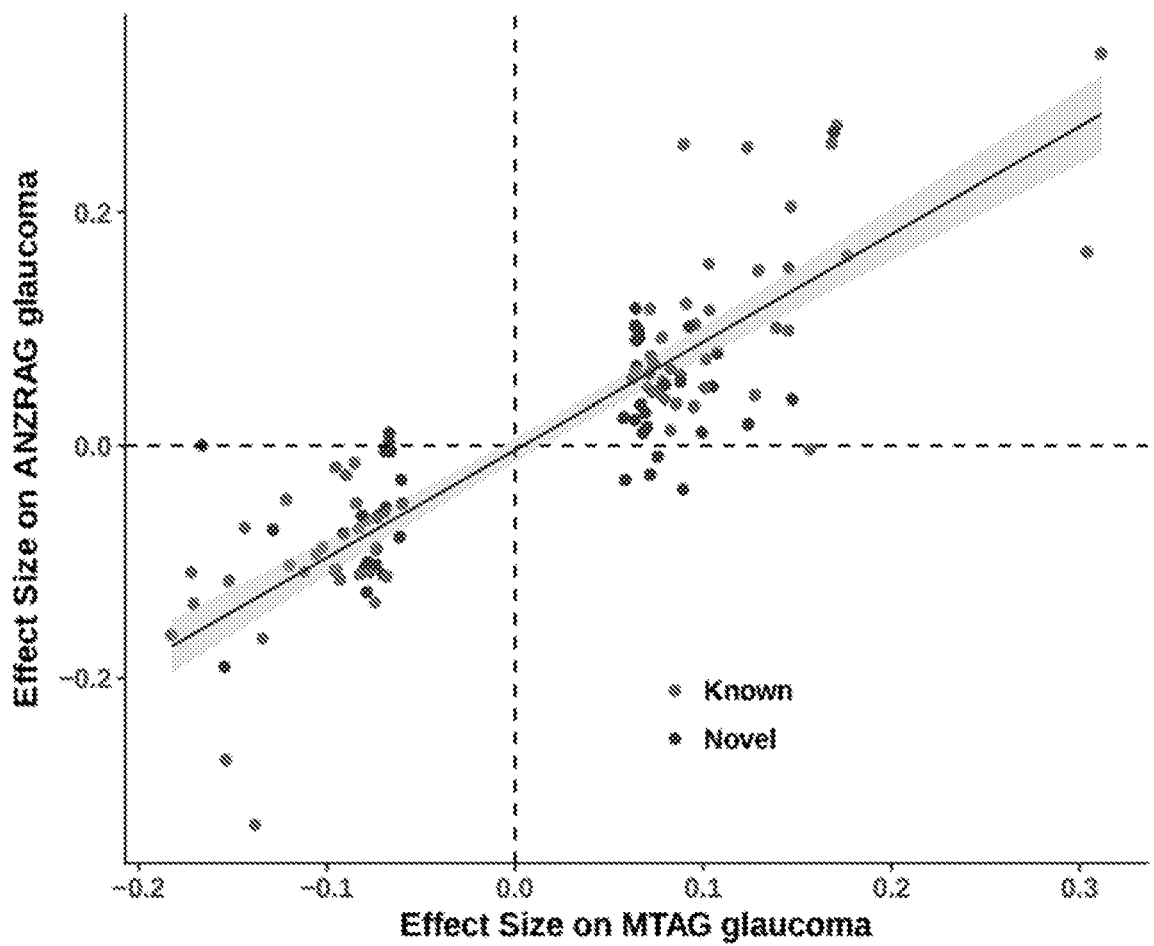
FIG. 5 shows comparison of the effect sizes for 114 MTAG glaucoma genome-wide significant independent SNPs versus that in an independent glaucoma cohort. Pearson's correlation coefficient is 0.85 (P value=$1.5\times10-32$). The red line is the best fit line with 95% confidence interval region in grey. Novel glaucoma SNPs are highlighted in red and known SNPs in blue.

The 50 novel SNPs frequently are not significantly associated ($P>5 \times 10-8$) with any of the input traits; more than half of the SNPs reach genome-wide significance for glaucoma due to the MTAG method leveraging the strong correlation between the input traits. We then replicated the candidate 50 novel SNPs in ANZRAG. The correlation between the MTAG glaucoma and ANZRAG glaucoma log ORs was very high (0.85), indicating our multivariate model is successfully identifying genuine glaucoma risk loci (FIG. 5).

Optimizing Prediction of Glaucoma Risk by Leveraging Correlated Traits

We derived the PRS based on MTAG of GWAS data from glaucoma and its endophenotypes; as well as increasing the number of SNPs that reach genome-wide significance, our multivariate model also improves the power of our PRS by minimizing the error in the estimate of the effect size for every SNP. We first tested the discriminatory power of our PRS in the ANZRAG cohort of advanced glaucoma. We found SNPs with MTAG P values<0.001 have the highest Nagelkerke $R^2$ (13.2%) and AUC (0.68, 95% CI: 0.67-0.70) (Table 12).

TABLE 12

| P value thresholds | Nagelkerke $R^2$ | AUC (95% confidence interval) |
|---|---|---|
| $5 \times 10^{-8}$ | 9.70% | 0.66[0.64, 0.67] |
| $1 \times 10^{-5}$ | 12.10% | 0.68[0.66, 0.69] |
| 0.001 | 13.20% | 0.68[0.67, 0.70] |
| 0.05 | 9.20% | 0.65[0.63, 0.67] |
| 1 | 6.90% | 0.63[0.62, 0.65] |

Figure 6B:
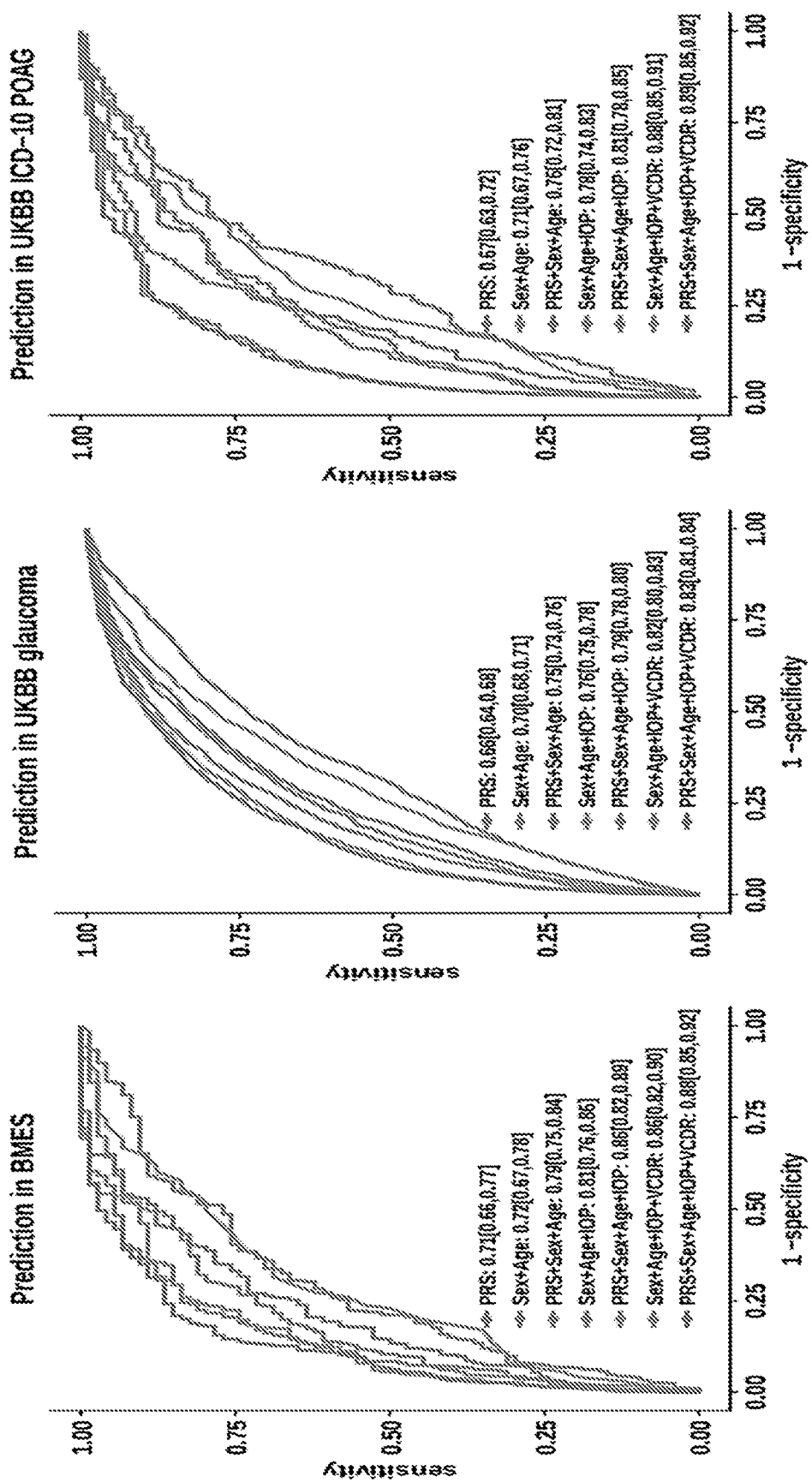
FIG. 6 shows MTAG PRS prediction. Panel A shows the OR (95% CI) of PRS in ANZRAG cohort of advanced glaucoma (with 1,734 advanced glaucoma cases and 2,938 controls; 709 high tension glaucoma cases and 1,991 controls; 330 normal tension glaucoma cases and 1,991 controls). The square dots are the OR values and the error bars are 95% CI. The dashed lines are reference at the bottom PRS decile (OR=1). Sex and the first four principal components were adjusted in logistic regressions. Panel B shows the AUCs of PRS in BMES and UKBB (glaucoma subtype unspecified and ICD-10 defined POAG). In each prediction model, PRS was added into the prediction model based on traditional risk factors (age, sex, IOP and VCDR were added in order). In all prediction models, PRS was generated from SNPs with P<0.001.

Based on this we set the P value threshold at 0.001 for all the remaining prediction target sets (PROGRESSA, BMES, UKBB glaucoma). Our risk score clearly separated advanced glaucoma individuals in terms of risk. For individuals in the top decile of the PRS, the risk of glaucoma was 14.9 fold higher (95% CI: 10.7-20.9) relative to the bottom decile, and with better discrimination for high tension glaucoma than normal tension glaucoma (FIG. 6A). Secondly, to benchmark the performance of our PRS with traditional risk factors in population based samples, we computed the AUC in three datasets; BMES, UKBB glaucoma (broad definition) and UKBB POAG (ICD-10 definition) (FIG. 6B). In each scenario, our PRS was added into the prediction models over and above traditional risk factors (age, sex, IOP and VCDR were added in order). Our PRS provided additional predictive ability beyond traditional risk factors, for example in BMES, our PRS improved the AUC from 0.72 to 0.79 above sex and age ($P=2.7 \times 10^{-3}$); from 0.81 to 0.86 above sex, age and IOP ($P=5.9 \times 10^{-3}$); from 0.86 to 0.88 above sex, age, IOP and VCDR (P=0.02). The gain of prediction ability from our PRS was similar in UKBB samples.

A previous study examined the cost-effectiveness requirements for glaucoma screening and highlighted the key age 50-60 bracket (Burr, J. M., G. Mowatt, R. Hernandez, M. A. R. Siddiqui, J. Cook, T. Lourenco, C. Ramsay, et al. 2007. "The Clinical Effectiveness and Cost-Effectiveness of Screening for Open Angle Glaucoma: A Systematic Review and Economic Evaluation." Health Technology Assessment 11 (41): iii-iv, ix-x, 1-190.). In the BMES data, screening only those with a top decile PRS identified 40% of all early onset cases in age 50-60 bracket (40% of the 10 cases, P=0.013). Such individuals represent a set of individuals likely to benefit from referral for immediate clinical assessment—with skilled clinical examination, retinal imaging, and visual fields. We replicated this result in the UKBB POAG cohort (ICD10 cases, top 10% PRS screening finds 29% of 24 cases aged 50-60, P=0.0075). In this way, PRS-based screening would satisfy the cost-effectiveness requirements of Burr et al, identify a meaningful proportion of cases, and capture those cases most at risk of severe disease.

This new glaucoma PRS also outperforms those derived from other well-studied conditions; for example our OR comparing the top 1% PRS individuals versus the remaining individuals was 8.5 which is higher than that seen in a recent study which surveyed coronary artery, atrial fibrillation, type 2 diabetes, inflammatory bowel disease and breast cancer. The aetiology of complex diseases depends on both environmental and genetic factors, thus PRS alone is unlikely to achieve the very high predictive power (e.g. AUC>0.99) required for accurate population screening. Our glaucoma PRS will be primarily useful for stratifying individuals into risk groups; for example in the BMES data, screening the top decile of the PRS in individuals between 50-60 years old identifies 40% of cases. Moreover, individuals with a high PRS for glaucoma are likely to be at a similar risk to individuals carrying rare "high penetrance" MYOC mutations. Finally, the PRS performance for glaucoma is particularly noteworthy given the clinical implications of identifying at-risk individuals and the prevention of irreversible blindness with readily available treatment proven to be effective at preventing visual loss.

Figure 7:
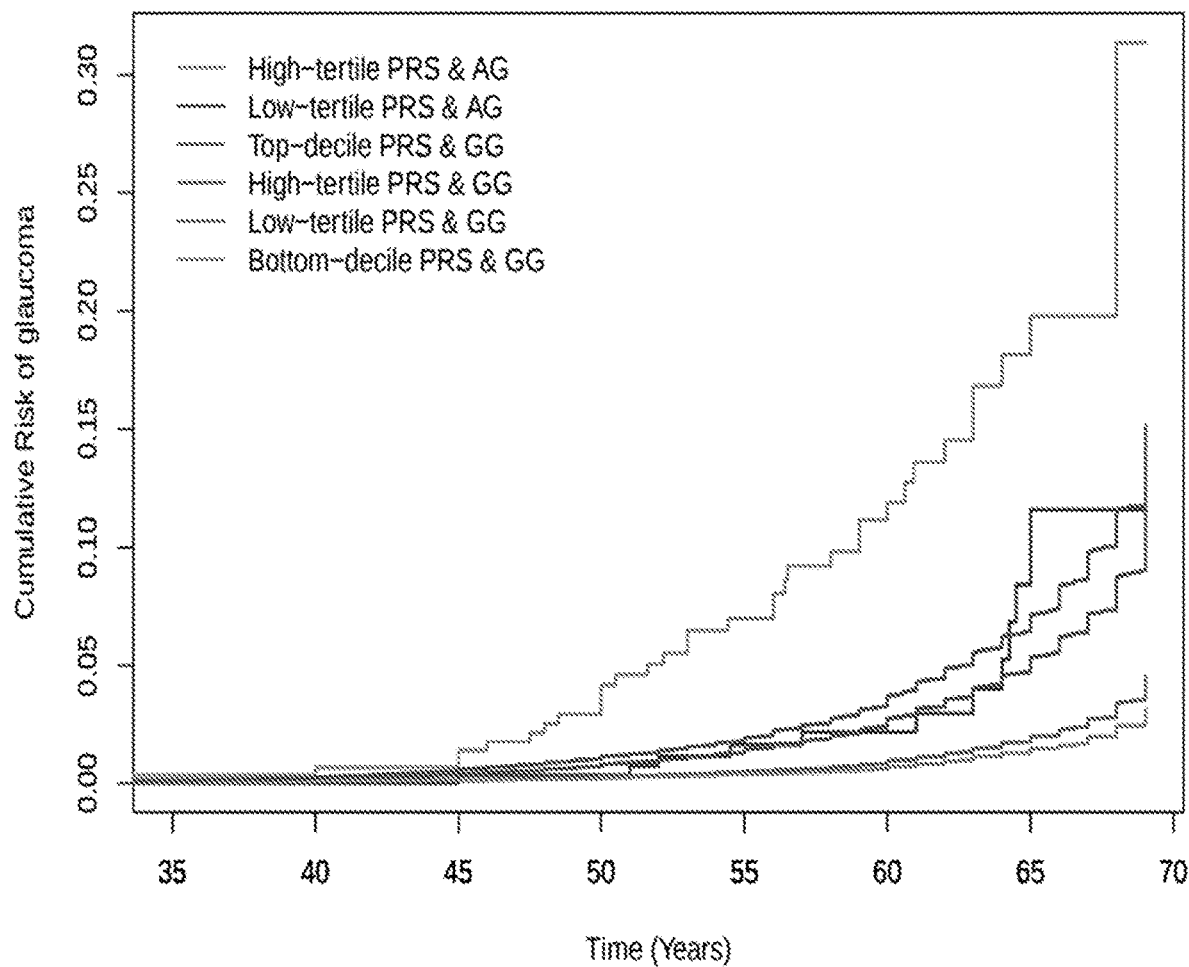
FIG. 7 shows cumulative risk of glaucoma in UKBB stratifying by MYOC p.Gln368Ter carriers and the PRS. Here tertiles of polygenic risk are displayed, given the relatively small number of MYOC p.Gln368Ter carriers (carriers were shown as AG, non-carriers as GG). For comparison the top and bottom PRS decile in non-carriers of MYOC p.Gln368Ter are displayed.

Glaucoma Polygenic Risk Score Performance in Individuals Carrying High Penetrance Variants Our PRS only contains common variants although given it indexes general glaucoma risk we hypothesized that it would stratify individuals carrying known high penetrance glaucoma variants. Specifically, within UKBB we identified 965 individuals who are MYOC p.Gln368Ter carriers based on. FIG. 7 shows the cumulative risk of glaucoma in UKBB stratifying by MYOC p.Gln368Ter (carriers and non-carriers) and the tertiles of our PRS. For MYOC p.Gln368Ter carriers in the lowest tertile PRS, their glaucoma risk remains very low (<2%) up to age 60, with their overall glaucoma risk (across all ages) not significantly different to non-carriers in the highest tertile PRS (P=0.45). In contrast, MYOC p.Gln368Ter carriers in highest tertile PRS groups have dramatically increased risk of early diagnosis, reaching absolute risk values of 10% and 12% by age 60, respectively. This supports the utility of PRS in optimizing risk stratification and early screening for MYOC p.Gln368Ter carriers.

Clinical Implications of the Glaucoma Polygenic Risk Score

PRS Influences Age at Diagnosis of POAG and the Number of Family Members Affected:

We evaluated the PRS in 1,336 ANZRAG advanced POAG cases with age at diagnosis information available. Individuals in the top 10%, and 20% of the allele score were on average diagnosed 7, and 5 years earlier, respectively, relative to the bottom 10%, and 20% groups and had significantly more family members affected by glaucoma (P=$2.97 \times 10^{-15}$).

PRS Correlates with Total RNFL Loss and Progression Rates in Early Manifest Glaucoma Thinning of the RNFL is a major structural change in the development of manifest early glaucoma. PRS is significantly associated with thinner RNFL (average peripapillary thickness (μM) of the most affected eye) in the PROGRESSA cohort after adjusting for patient's age at presentation and maximum recorded IOP (P=$3.45 \times 10^{-3}$). On average, the peripapillary RNFL was 0.67 μm thinner for each decile increase of PRS independent of age and maximum IOP (P=$5.15 \times 10^{-3}$).

Figure 8:
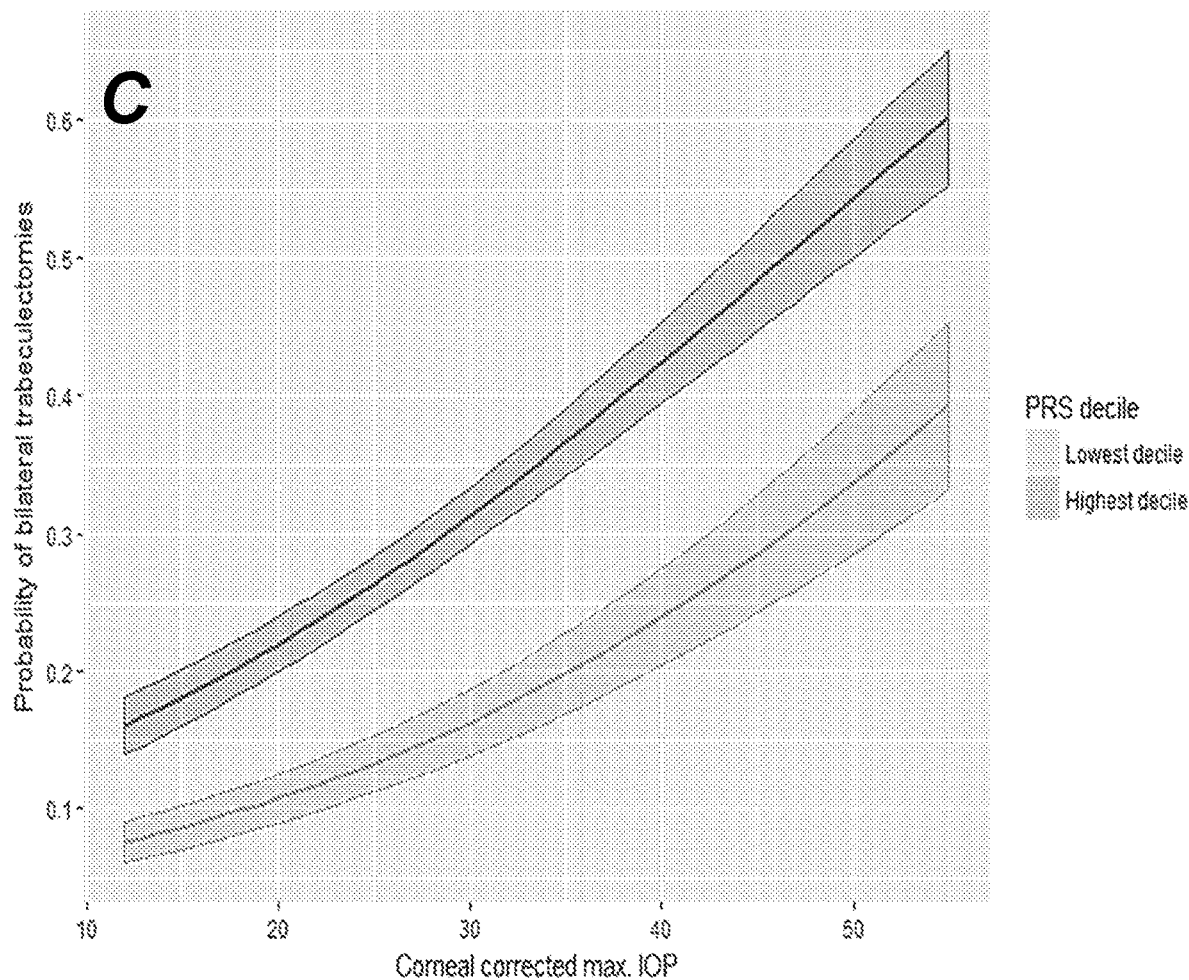
FIG. 8 shows clinical implications of the glaucoma PRS A) Mean age at diagnosis for each decile of PRS in the ANZRAG cohort. A total of 1,336 cases had accurate age at diagnosis information. We calculated the mean age at diagnosis for each decile of PRS adjusted for sex and the first four PCs in a linear regression model. The square dots are the regression-based mean age at diagnosis with error bars for 95% confidence interval. The red line is the best fit line with 95% confidence interval region in grey. B) The proportion of preserved baseline RNFL is shown for PROGRESSA participants who presented with early manifest glaucoma. The black dots are the RNFL proportions with error bars showing 95% confidence intervals. The remaining RNFL proportion is calculated for the most affected quadrant of the most affected eye of each patient—as determined on OCT scans at baseline and 3-5 years. The PRS is displayed in deciles. C) The relative proportion of patients requiring trabeculectomy in the ANZRAG cohort. The blue line is the estimated probability of bilateral trabeculectomy for participants in the lowest PRS decile, and the red line is the estimated probability of bilateral trabeculectomy in the highest PRS decile. The shaded regions display 95% confidence intervals.
Figure 9:
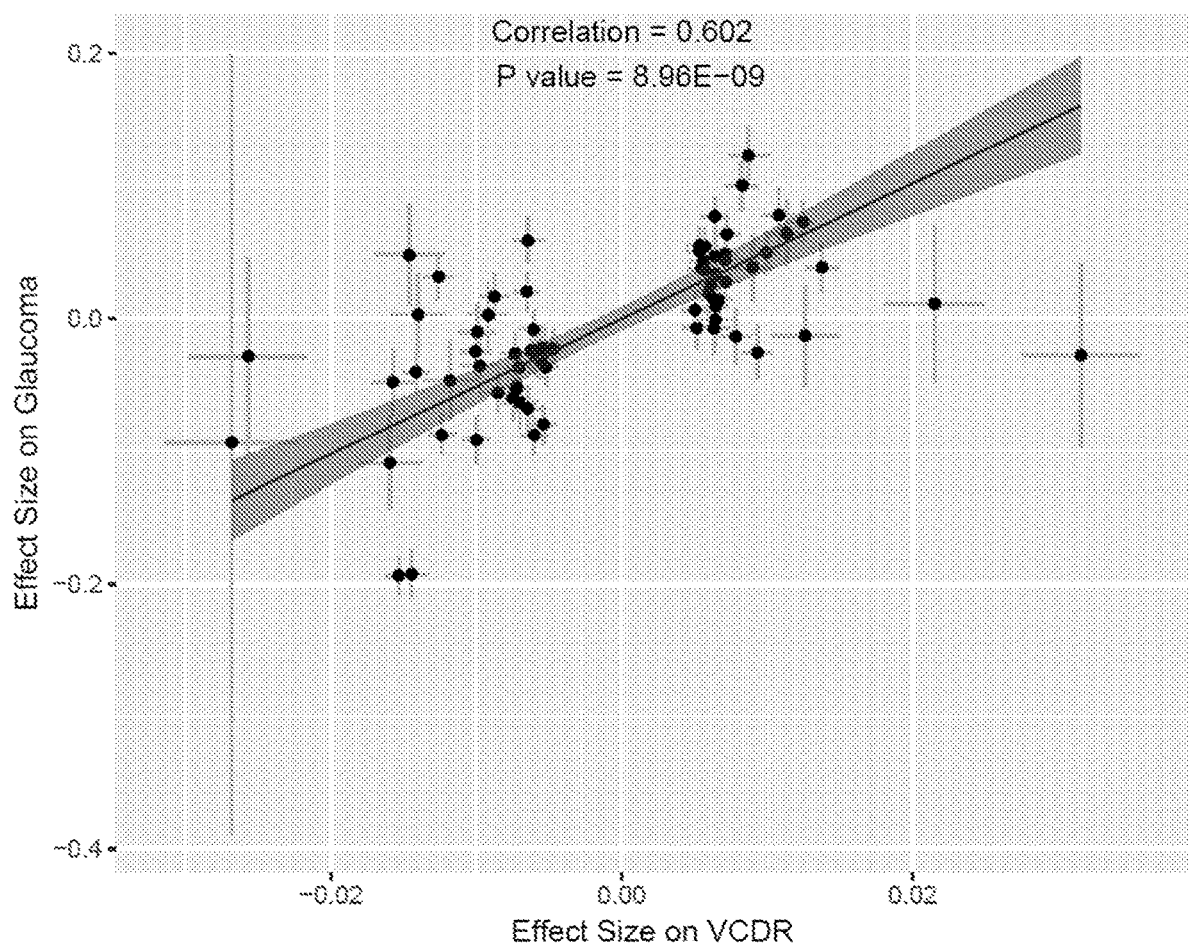
FIG. 9 shows comparison of the effect sizes for 76 UKBB VCDR (adjusted for VDD) lead SNPs versus that in independent glaucoma cohorts (log odds ratio in meta-analysis of ANZRAG and UKBB glaucoma GWAS). The Pearson's correlation coefficient is 0.60 (P value=$9.0\times10-9$). The diagonal line is the best fit line with 95% confidence interval region in grey. VCDR SNPs are represented by individual dots.

Glaucomatous damage to ganglion cells progresses unequally between eyes and some quadrants of the retina are damaged more rapidly. As such, in patients with early stage disease, the RNFL measurements for the most affected quadrant of the most affected eye were derived from longitudinal OCT data for three years or more (n=268; FIG. 8). The PRS is significantly associated with the absolute amount (μM) of RNFL lost from baseline (P=0.003) and the proportion of baseline RNFL lost (P=0.003) after multiple linear regression adjustment for age at presentation, baseline RNFL thickness, corneal corrected maximum recorded IOP and treatment status.

Increased Glaucoma Treatment in Patients with Higher PRS:

Patients with a high PRS had substantially greater rates of surgery for glaucoma. In the ANZRAG cohort of POAG cases, a high PRS is associated with requiring trabeculectomy even after adjustment of maximum recorded IOP and age (P=$2.75 \times 10^{-5}$). The OR of requiring trabeculectomy surgery for people in the top PRS decile is 2.34 (95% CI 1.58-3.49) compared to the bottom decile, after adjustment for maximum IOP and age.

Discussion

POAG one of the most heritable human diseases, is a leading cause of blindness worldwide. Whilst current treatments are generally effective in preventing disease progression, many patients present after irreversible damage to visual fields has already occurred. Given the large genetic component, genetic risk prediction is a desirable goal to aid in identifying people at highest probability of disease development. This would facilitate early treatment, whilst monitoring costs could be reduced for those in lower risk groups.

Prediction accuracy increased dramatically when the endophenotype data were included. Based on the multivariate prediction approach, individuals in the top decile for the genetic risk score were at 15 fold increased risk of glaucoma relative to the bottom decile. This compares favourably to our previously published risk prediction strategies based on the UKBB IOP PRS in which the top decile of genetic risk was associated with a 5.6 fold increased risk (Example 1). Amongst the cases, individuals in the top decile were diagnosed 7 years earlier than those in the bottom decile. The implications of diagnosing glaucoma earlier are important in reducing glaucoma blindness, particularly to the family members of high PRS cases as they are more likely to be affected by glaucoma. Our findings show that high PRS groups have more affected family members as well as illustrating the capability of PRS to stratify risk in carriers of highly penetrant mutations implies that in addition to the highly penetrant mutations, common variants contribute significantly towards glaucoma risk within families.

In addition to disease risk and age of onset, polygenic risk scores were also predictive of several clinical outcomes including need for treatment, intensity of treatment, need for surgery and structural disease progression. Clinical judgement on initiating and escalating treatment is an important end-point in monitoring and managing early glaucoma. High IOP is a key risk factor that influences clinical judgement on treatment. In early glaucoma, our PRS was predictive of both commencement of treatment and escalation to more medical, laser or surgical treatment independent of patient's age, and corneal corrected maximum IOP and maximum VCDR, all of which influence treatment decisions.

A strength of our study is that our results are robust to differences in the exact data used to derive our PRS and that our PRS has good predictive power in a range of scenarios. Showing our PRS predicts glaucoma risk and/or outcomes in multiple datasets is a key strength because it is not unusual for published prediction algorithms to fail to make useful predictions beyond the original application. For our predictions into ANZRAG and PROGRESSA we used the same training set to derive our PRS but to avoid overlaps between discovery and test datasets, for some prediction scenarios we had to slightly alter precisely which datasets were used; nonetheless, predictive accuracy remained high.

In advanced glaucoma, PRS was predictive of higher need for surgical intervention. Glaucoma surgery carries substantial risks but offers sight saving reduction of intraocular pressure below that which can be achieved with medical or laser therapy. It is highly important for clinicians to have the ability to more accurately predict which individuals with glaucoma will need and benefit from surgical treatment. There is also the potential for substantial cost saving by reducing treatment needs for low risk individuals who may not require any intervention. Earlier intervention with all forms of treatment in high risk individuals will reduce blindness rates from glaucoma which will provide a cost-effective strategy to justify costs of testing.

Supplementary Information
UK Biobank

Among the 487,409 individuals who passed initial genotyping QC, 409,694 participants had white-British ancestry, based on self-reported ethnicity and genetic principal components. To maximise our effective sample size, we also included UKBB participants if their self-reported ancestry was not white-British (this includes a substantial number of individuals reporting their ancestry as "Irish" or "any other white background") but their first two genetic principal components fell within the region of those that are classified white-British in the N=409,694 set in Bycroft et al. (ibid.).

UKBB VCDR GWAS

In UKBB, 87,685 left fundus retinal eye images were available (two assessment visits), covering 84,871 participants (UKBB Field 21015, 21016). The VCDR and VDD were assessed by two experienced ophthalmologists. Two thousand images were randomly selected for quality control, and the correlation of the VCDR measurements between the two ophthalmologists was 0.75 (95% CI 0.72-0.77), and the correlation of VDD measurements was 0.63 (95% CI 0.60-0.66). The second visit VCDR measurements were used if available, otherwise, we used the first visit VCDR measurements. In VCDR GWAS, we excluded non-white British ancestry participants and glaucoma cases and their relatives (pihat>0.2 calculated using identity by descent determined based on autosomal markers). Finally, 67,040 participants had both VCDR and VDD phenotype data. We used rank-based inverse-normal transformation to ensure VCDR were normally distributed. We used linear mixed model to account for cryptic relatedness and population stratification in the UKBB samples using BOLT-LMM version 2.3 (Loh P-R, Tucker G, Bulik-Sullivan B K, et al. Efficient Bayesian mixed-model analysis increases association power in large cohorts. Nat Genet 2015; 47(3):284-90). Association analysis was performed under an additive genetic model, adjusted for the effect of sex, age, the first ten PCs, two ophthalmologists, and two VCDR assessment visits. In addition, to adjust for the effect of optic nerve head size, as large optic discs are associated with higher VCDR, VDD was added as a covariate in VCDR GWAS.

UKBB Glaucoma Case-Control Analysis
Definition

We assessed associations between SNPs and glaucoma status adjusted for sex and the first six principal components, under an additive genetic model using the dosage scores obtained from imputation. Association analysis was performed using PLINK version 2.0 (Purcell S, Neale B, Todd-Brown K, et al. PLINK: a tool set for whole-genome association and population-based linkage analyses. Am J Hum Genet 2007; 81(3):559-75). Identity by descent was determined based on autosomal markers in PLINK version 1.90b, and only one of each pair of individuals with pihat>0.2 was used in the analysis.

We used mean chi-squared and the univariate LD score regression approach to investigate presence of model or structural bias in the glaucoma GWAS data (Bulik-Sullivan B K, Loh P-R, Finucane H K, et al. L D Score regression distinguishes confounding from polygenicity in genome-wide association studies. Nat Genet 2015; 47(3):291-5). An LD score intercept close to 1 in a univariate analysis indicates that there is no model misspecification and that other sources of bias such as population stratification and cryptic relatedness are not adversely affecting results.

UKBB MYOC p.Gln368Ter Carriers and Cumulative Risk of Glaucoma

In this subset study of UKBB, after remove relatives and other serious eye diseases participants, 382,161 participants were included. We identified MYOC p.Gln368Ter carriers using the imputation posterior probability of rs74315329. Our previous study has shown that MYOC p.Gln368Ter can be imputed with high accuracy from genotyping arrays. In this study, the risk allele (A) dosage of rs74315329 was calculated. We defined MYOC p.Gln368Ter carriers by setting the dosage threshold at 0.8 and identified 965 carriers (minor allele frequency 1/790, 0.13%), of them 72 carriers are glaucoma cases. We gathered the information for age at diagnosis of glaucoma from UKBB field 4689 and 20009. In total, the age at diagnosis information was available for 4,596 individuals. For glaucoma cases without age at diagnosis information, we used their age as the age of diagnosis. The training datasets used to construct MTAG PRS were shown in FIG. 1. To avoid sample overlap for MYOC p.Gln368Ter carriers, we removed all MYOC p.Gln368Ter carriers and their relatives from UKBB VCDR and IOP GWAS. Cox model was used to calculate the cumulative risk of glaucoma for MYOC p.Gln368Ter carriers and non-carriers by the tertiles of PRS. In the Cox model, we adjusted sex and first six genetic principal components. The "survival" package in R was used in analysis.

International Glaucoma Genetic Consortium Study

Publicly available VCDR and IOP GWAS summary results were downloaded for individuals of European descent from the International Glaucoma Genetic Consortium study (IGGC, $N_{VCDR}$=23,899, $N_{IOP}$=29,578). The GWAS of VCDR and TOP in IGGC were imputed by 1000G and adjusted age, sex and the first five PCs.

The Australian & New Zealand Registry of Advanced Glaucoma (ANZRAG) Cohort:

The clinical recruitment and characterisation of the ANZRAG cohort has been described previously. For this analysis a total of 3,071 POAG cases and 6,750 historic controls of European descent were used. Case and control samples were genotyped on Illumina Omni1M, OmniExpress or HumanCoreExome arrays (Illumina, San Diego, USA). This dataset involved three phases of POAG data collection, and hence, QC, imputation, and association analysis was conducted separately for each phase before combining the results in a meta-analysis. The first phase was previously published and comprises 1,155 advanced POAG cases and 1,992 historic controls genotyped on Illumina Omni1M or OmniExpress arrays. In this phase the historic controls were obtained from 225 oesophageal cancer cases, 317 Barrett's esophagus cases and their 552 controls, as well as 303 inflammatory bowel diseases cases and their corresponding cohort of 595 controls. The second phase includes a further 579 advanced POAG cases genotyped on Illumina HumanCoreExome array and 946 controls selected from parents of twins previously genotyped on the same array. The third phase comprises 1,337 POAG cases genotyped on the Illumina HumanCoreExome array and 3,812 controls selected from a study of endometriosis previously genotyped using the same array. There is strong female bias in the control set in phase three, but not in phases one and two (our allele score prediction work below uses only phases one and two).

As described previously, QC was performed using PLINK.[21] Individuals with more than 3% missing genotypes, and SNPs with call rate less than 97%, minor allele frequency (MAF)<0.01, and Hardy-Weinberg equilibrium (HWE) P<0.0001 in controls or P<$5\times10^{-10}$ in cases were removed from the analysis. Identity by descent was determined based on autosomal markers in PLINK (Purcell S, Neale B, Todd-Brown K, et al. PLINK: a tool set for whole-genome association and population-based linkage analyses. Am J Hum Genet 2007; 81(3):559-75), and only one of any pair of individuals with relatedness (pihat of >0.2 was used in the analysis. PLINK was used to compute principal components for all participants and reference samples of known northern European ancestry (1000G British, CEU, Finland participants). Participants with PC1 or PC2 values>6 standard deviations from the mean of known Northern European ancestry group were excluded. All statistical tests throughout the manuscript were two-sided.

Phasing of the genotyped SNPs was conducted using ShapeIT (Delaneau O, Marchini J, Zagury J-F. A linear complexity phasing method for thousands of genomes. Nat Methods 2011; 9(2):179-81), and imputation was performed using Minimac3 through the Michigan Imputation Server (Das S, Forer L, Schonherr S, et al. Next-generation genotype imputation service and methods. Nat Genet 2016; 48(10):1284-7, with the HRC as the reference panel (McCarthy S, Das S, Kretzschmar W, et al. A reference panel of 64,976 haplotypes for genotype imputation. Nat Genet 2016; 48(10):1279-83). SNPs with imputation quality ($\hat{r}^2$) >0.3 and MAF>0.01 were used for analysis.

The Blue Mountains Eye Study (BMES):

Subjects participated in the Blue Mountains Eye Study, as previously described. In brief, the BMES is a population-based cohort study investigating the etiology of common ocular diseases among suburban residents aged 49 years or older, living in the Blue Mountains region, west of Sydney, Australia. The population in this area is stable and ethnically homogeneous of predominantly Anglo-Celtic descent. Subjects were recruited during one of four surveys between 1992 and 2004. The baseline BMES survey was conducted between 1992 and 1993, recruiting a total of 3654 participants (82.4% of 4433 eligible persons identified in a private census). Of these people, 2564 (70.2%) were re-examined during the five- and ten-year follow-up studies. An ancillary study conducted between 1998 and 2000 examined an additional 1174 people who had either reached the eligible age (49+ years) for participation or had relocated into the study area (85.2% of 1378 newly eligible persons identified in a second private census). DNA samples were obtained during the five-year follow-up and ancillary surveys. For the PRS prediction in BMES, we calculated the baseline mean IOP and mean VCDR of the left and right eyes for each participants. Finally, 74 POAG cases and 1721 controls of European descent with genotype data, IOP and VCDR measurements available were included in analysis.

Predicting Risk of Glaucoma: RElevant SNPs with Strong Association (PROGRESSA) Study:

Participants were tested at the Flinders Medical Centre and various private Ophthalmology practices in South Australia, Australia. Inclusion criteria were an age between 18 and 85, the ability to provide written consent and attend six-monthly visits for 5 years, two reliable visual field tests separated by less than 12 months, demonstrating early manifest glaucoma at the time of recruitment. Exclusion criteria at entry included an inability to perform reliable visual field testing, Humphrey mean deviation worse than −6.0 dB, best corrected visual acuity worse than 6/18 in either eye, angle closure or other conditions that affect the visual field.

The patients performed Humphrey Visual Field (HVF) 24-2 SITA Standard at the baseline visit and each follow-up 6 monthly visit. Reliable visual fields were determined based on having less than 33% fixation loss, false-positive rates and false-negative rates. A reliable baseline visual field test was considered abnormal if the results of the glaucoma hemifield test (GHT) were outside normal limits, corrected pattern standard deviation (PSD) of P<0.05, or there was a cluster of at least 3 contiguous points in a glaucoma region, all of which depressed at a P<0.05 level with at least one depressed at P<0.01 on the pattern deviation plot (Hodapp-Parrish-Anderson criteria). The glaucoma regions were defined as the paracentral, Bjerum, nasal step and temporal wedge in each hemifield. A second confirmatory HVF test was required to demonstrate a cluster in the same glaucoma region with the same criteria described above. Alternatively, the second HVF test was considered confirmatory if it had an abnormal PSD or GHT (as defined above) and there was a cluster in the same region of at least 3 contiguous points all depressed at P<5%).

Optical coherence tomography (OCT) as measured by a Cirrus HD-OCT (Carl Zeiss Pty Ltd), was used to measure the thickness of peripapillary retinal nerve fibre layer (RNFL).

The PROGRESSA cohort comprised of 269 EMG cases with mean follow up time of 3.5±1.4 years. There were 121 male and 148 female participants, with mean age of 67.8±9.7 years at recruitment. The mean maximum IOP was 19±4 mm Hg, and vertical cup to disc ratio (VCDR) of 0.74±0.1. The mean OCT peripapillary RNFL thickness was 83.3±11.3 μm.

Definition of Independent Genome-Wide Significant Loci

We conducted stepwise model selection procedures in GCTA-COJO (Yang J, Ferreira T, Morris A P, et al. Conditional and joint multiple-SNP analysis of GWAS summary statistics identifies additional variants influencing complex traits. Nat Genet 2012; 44(4):369-75, S1-3) to identify independent genome-wide significant SNPs. GCTA-COJO uses GWAS summary results and estimates LD from a reference sample (randomly selected 5,000 UKBB white British ancestry individuals) for the conditional and joint association analysis. We defined independent SNPs with both raw P values and joint P values less than $5×10^{-8}$ within a two megabases region.

Definition of Novel Loci

We used HaploReg (Ward L D, Kellis M. HaploReg: a resource for exploring chromatin states, conservation, and regulatory motif alterations within sets of genetically linked variants. Nucleic Acids Res 2012; 40(Database issue):D930-4) to identity all the proxy SNPs (r2>=0.8) of the lead SNPs from GCTA-COJO. The lead SNPs, their proxy SNPs, and the located genes were checked in GWAS Catalog (MacArthur J, Bowler E, Cerezo M, et al. The new NHGRI-EBI Catalog of published genome-wide association studies (GWAS Catalog). Nucleic Acids Res 2017; 45(D1):D896-901), and PubMed. To define novel VCDR loci, we excluded known VCDR loci, and similarly for novel glaucoma loci, we excluded known glaucoma loci.

MTAG Method

We used multi-trait analysis of GWAS (MTAG) to perform joint analysis of GWAS summary results from related traits to improve statistical power to identifying new genes and to maximize the predictive ability of our polygenic risk scores. In MTAG, GWAS summary results from related traits are used to construct the variance-covariance matrix of their SNP effects and estimation error; MTAG improves the accuracy of effect estimates by incorporating information from other genetic correlated traits. We conducted four trait MTAG using the GWAS summary results from UKBB glaucoma, UKBB VCDR (adjusted for VDD), IGGC VCDR, and IOP meta results. The MTAG method explicitly models sample overlap in the input studies and provides valid estimates even when sample overlap is present (Turley P, Walters R K, Maghzian O, et al. Multi-trait analysis of genome-wide association summary statistics using MTAG. Nat Genet 2018; 50(2):229-37). We replicated the new glaucoma loci from MTAG in ANZRAG.

Polygenic Risk Score and Prediction

To assess the prediction value of our MTAG method derived PRS, we calculated PRS in PLINK: LD-clumping followed by P value thresholding (PLINK version 1.90 beta, -clump-p1 1 -clump-p2 1 -clump-r2 0.1 -clump-kb 1000, and P values thresholds at $5×10^{-8}$, $1×10^{-5}$, 0.001, 0.05, 1) (Purcell S, Neale B, Todd-Brown K, et al. PLINK: a tool set for whole-genome association and population-based linkage analyses. Am J Hum Genet 2007; 81(3):559-75). LD clumping was based on the overlap SNPs between training and target datasets.

PRS was evaluated in the following training and target samples. There is no sample overlap between each of the training and target datasets:

1. As shown in FIG. 3, in the training step, we performed 4 traits MTAG from UKBB glaucoma GWAS, UKBB VCDR (VDD adjusted), IGGC VCDR and IOP meta GWAS. We used the PLINK LD-clumping+thresholds method to calculate PRS from MTAG output for UKBB glaucoma. The target outcome was ANZRAG advanced POAG status (1,734 cases and 2,938 controls). We calculated the Nagelkerke's pseudo $R^2$ and AUC from the logistic regression adjusted sex and the first four principal components. We also compared the POAG risk between the top and bottom PRS quantile groups (5%, 10% and 20%).

2. Same as No. 1, to derive the PRS, we also evaluated POAG related structural and functional endpoints and the likelihood of progression in PROGRESSA.

3. To further evaluate the prediction ability of MTAG derived PRS over and above the traditional risk factors, we performed 3 traits MTAG from ANZRAG and UKBB glaucoma meta GWAS, UKBB VCDR (VDD adjusted) GWAS, and UKBB IOP GWAS (FIG. S1B). Here to avoid the sample overlap between IGGC and BMES, we removed IGGC VCDR and IOP GWAS summary results. The target dataset was 74 POAG cases and 1,721 controls in BMES with IOP and VCDR available. We calculated the AUC for PRS, PRS+sex+age, PRS+sex+age+IOP, and PRS+sex+age+IOP+VCDR.

4. We performed 4 traits MTAG from ANZRAG POAG GWAS, UKBB VCDR (VDD adjusted) GWAS, IGGC VCDR GWAS and IOP meta GWAS. In UKBB, we removed 3,000 non-glaucoma participants (selected randomly, we also removed their relatives) with both IOP and VCDR available and rerun the VCDR and IOP GWAS. The target dataset was 1,421 glaucoma cases and the 3,000 controls in UKBB. Both of the cases and controls were unrelated and had IOP and VCDR measurements. We calculated the AUC for PRS and its combination with traditional risk factors. We also evaluated the AUC in 112 ICD-10 defined POAG cases and the 3,000 controls in UKBB.

5. We performed 4 traits MTAG from ANZRAG POAG GWAS, UKBB VCDR (VDD adjusted), IGGC VCDR and IOP meta GWAS. To avoid sample overlap for MYOC p.Gln368Ter carriers, we removed all MYOC p.Gln368Ter carriers and their relatives from UKBB VCDR (VDD adjusted) and IOP GWAS. We used Cox model to calculate the cumulative risk of glaucoma for MYOC p.Gln368Ter carriers and non-carriers by the tertiles of the MTAG PRS. In the Cox model, we adjusted sex and first six genetic principal components.

Clinical Implications: Methods and Statistical Analysis

PROGRESSA cohort clinical data used for analysis were recorded at each visit by the treating clinician. OCT scans were obtained using Cirrus HD-OCT (CarlZeiss Meditec, Inc., Dublin, CA) at each visit and any poor quality scans were discarded and repeated on the same day. The Optic Disc Cube 200×200 scan generates a 6 mm by 6 mm square grid by acquiring 200 horizontal lines of 200 A-scans. The peripapillary RNFL thickness is based on a circle of diameter 3.46 mm around the centre of the optic disc. The average and quadrant thickness data of this circle is displayed under the RNFL Thickness Analysis of the Cirrus OCT software. Poor quality scans as defined by the manufacturer's own inbuilt quality score, and scans with artifacts and segmentation errors were excluded from analysis.

All statistical analysis of PRS and RNFL data, as well as need for trabeculectomy analysis, was done using R statistical software. Continuous variables were compared using two-sample Student's T-test (t.test function) or Wilcoxon rank sum test (wilcox.test function) for parametric and non-parametric data respectively. Normality was checked using Shapiro-Wilk test (shapiro.test function).

A multiple linear regression model was used when comparing a continuous dependent variable whilst adjusting for multiple independent variables. Regression analysis were done using linear regression (lm function) or generalised linear regression (glm function) from the base R stats package. A Box-Cox profile likelihood (Box GEP, Cox DR. An Analysis of Transformations. J R Stat Soc Series B Stat Methodol 1964; 26(2):211-52) was used to assess the need for transformation of the dependent variable (boxcox function; MASS package; Venables W N, Ripley B D. Modern Applied Statistics with S [Internet]. 2002; Available from: http://www.stats.ox.ac.uk/pub/MASS4); the profile likelihood of lambda, the exponent of a power transformation, guided the choice of transformation where indicated.

The model assumptions were checked during regression diagnostics. The linearity and homoscedasticity assumptions were visually assessed using scatter plots of the fitted and predicted residuals. There was no pattern in the residuals and they were equally spread around the y=0 line. The normality assumption was assessed using a quantile-quantile plot of the model residuals; observations lay along the 45-degree line. So too, Cook's distance was assessed to quantify the leverage of any individual point in the overall model; no points were identified as having undue influence and no points were excluded.

Web Resources Used:
- BOLT-LMM: https://data.broadinstitute.org/alkesgroup/BOLT-LMM/
- GCTA software: http://cnsgenomics.com/software/gcta/
- GWAS Catalog: https://www.ebi.ac.uk/gwas/
- HaploReg: http://archive.broadinstitute.org/mammals/haploreg/haploreg.php
- Haplotype Reference Consortium: http://www.haplotype-reference-consortium.org/
- International Glaucoma Genetic Consortium dataset: https://goo.gl/73qHqk
- LOCUSZOOM: http://locuszoom.sph.umich.edu/
- METAL software: http://csg.sph.umich.edu/abecasis/Metal/
- PLINK software: http://www.cog-genomics.org/plink2
- R: https://cran.r-project.org/UK
- Biobank: http://www.ukbiobank.ac.uk/

Example 3—Use of a Genetic Test to Inform Treatment of a Subject for Glaucoma

A genetic test may be employed for a subject of interest. The identity of genetic markers in the subject may be determined by taking an appropriate sample from a subject and determining the genetic content at selected genetic loci or markers, for example by DNA microarray analysis or Next Generation Sequencing using the appropriate hardware and software. The genetic markers, optionally in combination with one or more clinical features, may be used to assess the risk of, and/or treatment options, for primary open angle glaucoma as described herein. In some cases, the assessment of risk may be made without receiving or using clinical data. In other cases, the assessment of risk may be made using clinical data.

For example, the risk assessment may be determined using a system whereby an algorithm is interrogated using a computer processor over the internet with information on the genetic content at selected genetic loci or markers (as determined above) and one or more clinical features. The algorithm may, for example, then be used to provide a risk score for the subject, which may then be used to inform a professional as to management of the subject moving forward, such as detailed below.

For example, a subject in the general population may elect to undertake the genetic test at the age of (for example) 40-50 years. In the event of a high risk of primary open angle glaucoma being predicted by the test, a referral to an optometrist or ophthalmologist is triggered for a set of baseline clinical tests. These will include, but not be limited to, measurement of intraocular pressure, baseline automated perimetry, examination and baseline documentation of the optic nerve head, retinal nerve fibre layer, macular ganglion cell layer by ocular coherence tomography, optic disc photography, and measurement of ocular biomechanics.

In the event of abnormalities consistent with ocular hypertension or glaucoma, early treatment would be initiated. In the event of normal examination and test findings, a regular ongoing measurement of these parameters will be performed with the goal of early detection of clinical change to facilitate early treatment to prevent visual loss from glaucoma. On the contrary, upon the return of a low risk genetic profile, it may be deemed that detailed screening for glaucoma is not required until later in life, and at a lower frequency.

For example, a subject may be aware of a positive family history of glaucoma, but details of the clinical diagnosis of the affected family member may be lacking. The subject wishes to explore their personal risk of currently having or developing glaucoma. The genetic test is performed and the risk of the subject developing primary open angle glaucoma or advanced primary open angle glaucoma is thereafter modified by the results of the test. A low risk test result allows the subject to continue 2 yearly screening in the community optometric setting. A high risk result leads to a referral to an ophthalmologist wherein detailed baseline screening for primary open angle glaucoma is performed, with the goal of facilitating early treatment at the first signs of glaucoma developing, and before vision loss has occurred.

In another example, a subject may present to an optometrist in order to have a routine eye check. Included in the routine eye check is a tonometry test and examination of the optic nerve head by either clinical means, optical coherence tomography, or photography, and visual field testing by automated perimetry. In the event of any abnormal results suggestive but not necessarily diagnostic of glaucoma, a genetic test may be undertaken as part of referral to an ophthalmologist. The results of the genetic test may be available to the referred ophthalmologist and used alone, or in conjunction with one or more clinical features, to make a determination of the risk of primary open angle glaucoma being present, or developing in the future. The timing of treatment initiation and the frequency of follow up monitoring tests is modified by the result of the genetic test.

In another example, a subject found to be in the early stages of glaucoma using routine clinical examination, is subjected to the genetic test by the treating optometrist or ophthalmologist. The presence of a high risk test result indicates that there is a higher risk of rapid progression of disease, and a higher risk that surgical intervention for glaucoma will be required. This leads to more aggressive acceleration through treatment stages to reduce the probability of rapid progression, including the possibility of early surgical intervention. On the contrary, in the presence of a low risk test result and in consideration of other factors, for example advanced age of the subject, a decision may be made to not treat the subject, but instead monitor for progression without initiation of treatment.

Typically, the information on the genetic content of the various markers in the subject will be assessed by use of DNA microarray analysis, and the test utilises the genetic information from a combination of one or more of genetic markers associated with increased intraocular pressure, vertical cup to disk ratio, glaucoma disease, and/or a multivariate test, optionally in combination with one or more clinical features of the subject, such as one or more of n certain embodiments, the one or more clinical features comprising one or more of age, gender, family history of glaucoma, intraocular pressure, vertical cup to disc ratio, corrected vertical to cup disk ratio, data from optical coherence tomography of the optic nerve head, retinal nerve fibre layer, retinal ganglion cell layer, data from automated perimetry, ocular biomechanical factors (corneal thickness, corneal hysteresis, corneal rigidity), and systemic vascular factors (blood pressure, cerebrovascular disease, ischemic heart disease, migraine, Raynauds disease). Methods for assessing the aforementioned clinical features are known in the art.

For a subject identified as being at high risk of developing glaucoma, for example by having a risk score in the top 10% of the score distribution, then a medical practitioner may elect for the subject to undergo treatment for glaucoma irrespective of the disease stage of that individual.

For example, a subject may present to an optometrist in order to have a tonometry test and if that is indicative of glaucoma, a genetic test may be undertaken as part of referral to an ophthalmologist. The results of the genetic test may be available to the referred ophthalmologist and used alone or in conjunction with one or more clinical features.

Typically, the information on the genetic content of the various markers in the subject will be assessed by use of DNA microarray analysis, and the test utilises the genetic information from a combination of genetic markers associated with one or more of increased intraocular pressure, glaucoma disease, vertical cup to disk ratio, and/or a multivariate test, optionally in combination with one or more clinical features of the subject, such as one or more of n certain embodiments, the one or more clinical features comprising one or more of age, gender, family history of glaucoma, intraocular pressure, vertical cup to disc ratio, corrected vertical to cup disk ratio, data from optical coherence tomography of the optic nerve head, retinal nerve fibre layer, retinal ganglion cell layer, data from automated perimetry, ocular biomechanical factors (corneal thickness, corneal hysteresis, corneal rigidity), and systemic vascular factors (blood pressure, cerebrovascular disease, ischemic heart disease, migraine, Raynauds disease). Methods for assessing the aforementioned clinical features are known in the art.

For a subject identified as being at high risk of developing glaucoma, for example by having a risk score in the top 10% of the score distribution, then a medical practitioner may elect for the subject to undergo treatment for glaucoma.

A variety of drug and medical interventions are known for the treatment of primary open angle glaucoma.

Examples of drug treatments are set out in the following table.

| Drug class | Drug and daily frequency | Route | Mechanism of action |
|---|---|---|---|
| Prostaglandin analogs | Latanoprost 1x Travoprost 1x Unoprostone 2x Bimatoprost 1x | Topical | Increased trabecular drainage |
| Beta blockers | Betaxolol 2x (selective) Carteolol 2x Timolol 1-2x Levobunolol 1-2x | Topical | Decreased aqueous fluid production |
| Diuretics (carbonic anhydrase inhibitors) | Brinzolamide 3x Dorzolamide 3x Acetazolamide 2-4x Methazolamide 2-3x | Topical Oral | Decreased aqueous fluid production via $HCO_3^-$ |
| Cholinomimetics | Carbachol 3x Pilocarpine 3-4x Physostigmine 1-4x | Topical DOG Plastic Film | Open the TM by contraction of ciliary muscle forces |

-continued

| Drug class | Drug and daily frequency | Route | Mechanism of action |
|---|---|---|---|
| Alpha agonists (selective) | Epinephrine 1-2x Dipivefrin 2x | Topical | Increased trabecular flow |
| Alpha agonists (non-selective) | Brimonidine$^a$ 3x | Topical | Reduced aqueous production and increased uveoscleral flow |

Dosages for administration of the aforementioned drugs may be selected by a medical practitioner.

Other medical interventions for primary open angle glaucoma include incisional surgery or laser surgery, alone or in combination with drug administration. Treatment may be initiated in a stepwise fashion beginning with topical drug therapy (single then multidrug combinations) followed by laser trabeculoplasty, and if needed, filtering surgery (trabecular meshwork or Schlemm's canal surgery, trabeculectomy, and implantation of shunts) aimed at draining aqueous humor from the eye.

Figure 13:
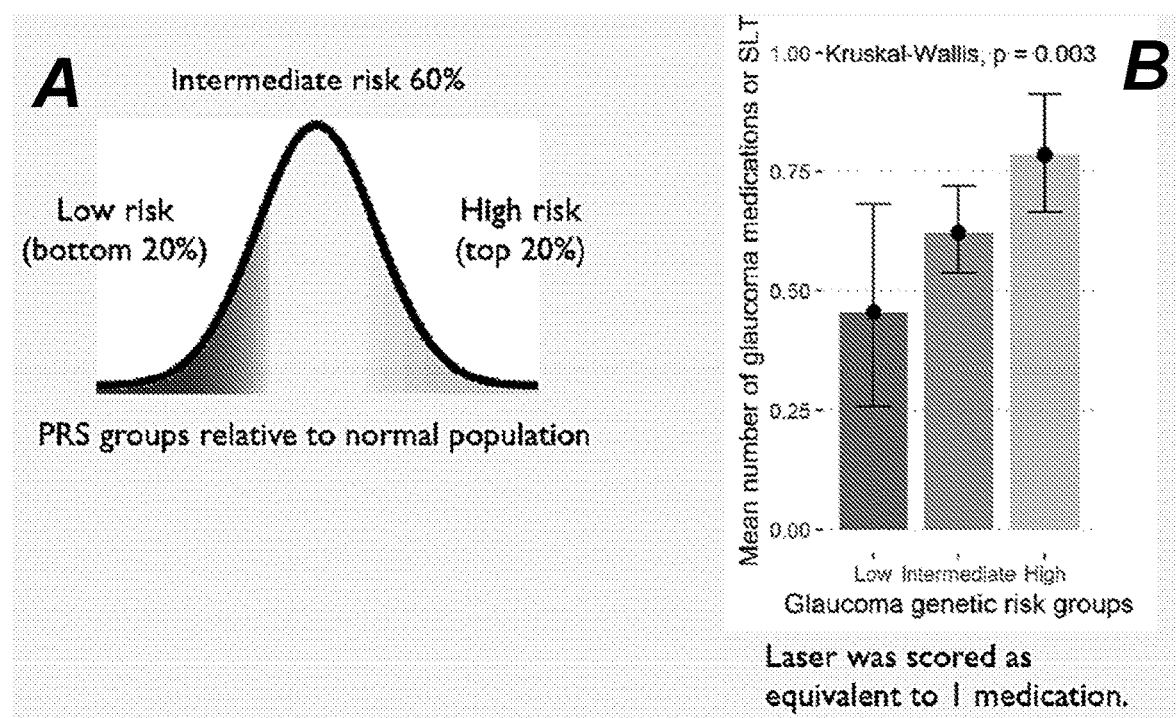
FIG. 13 shows that the glaucoma polygenic risk score used in this study predicts the intensity of medical treatment or laser treatment in early glaucoma. Panel A shows the polygenic risk groups relative to the normal population. Panel B shows that the polygenic risk predicts the intensity of medical treatment with glaucoma medication or selective laser trabeculoplasty.

FIG. 13 shows that the glaucoma polygenic risk score as described herein predicts the intensity of medical treatment or laser treatment in early glaucoma.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of treating primary open angle glaucoma in a subject, the method comprising:
   (i) determining a risk score for primary open angle glaucoma in the subject on the basis of the genetic content of the subject at a plurality of selected genetic loci or markers and thereby assessing the risk of primary open angle glaucoma in the subject, wherein:
      (a) the selected genetic loci or markers comprise (ai) genetic loci or markers having an association with glaucoma, and (aii) genetic loci or markers having an association with increased intraocular pressure, and (aiii) genetic loci or markers having an association with an increased vertical cup to disk ratio, and/or
      (b) the selected genetic loci or markers have an association with a multi-trait test of glaucoma, intraocular pressure and vertical cup to disc ratio,
      wherein the association comprises a threshold for genome-wide significance of $p < 5 \times 10^{-8}$;
   (ii) identifying the subject as having a high risk score; and
   (iii) administering to the subject with a high risk score one or more of laser treatment, selective laser trabeculoplasty, administration of a drug, surgical intervention, and incisional surgery or laser surgery, alone or in combination with drug administration,
   wherein the genetic loci or markers having an association with increased intraocular pressure comprise greater than 7% of the genetic loci or markers having an association with increased intraocular pressure listed below:

| Locus | SNP (Effect Allele) |
|---|---|
| TRIOBP | rs5756813-G |
| SYN3 | rs756481-A |
| EMID1 | rs9608740-C |
| TXNRD2 | rs76945759-G |
| LINC00314 | rs4629237-A |
| PTPN1 | rs6095946-C |
| LINC01370 | rs6065171-T |
| LOC339593 | rs34952318-G |
| CPXM1 | rs215543-G |
| ZNF516 | rs1047922-C |
| BCAS3 | rs1558225-G |
| FLJ40194 | rs11079868-G |
| NSF | rs199529-C |
| GAS7 | rs9913911-A |
| GAS7 | rs10852918-G |
| FANCA | rs3743860-T |
| ADAMTS18 | rs12444539-T |
| IL34 | rs35381200-C |
| CDH11 | rs1874458-G |
| VPS13C | rs4775427-T |
| ZNF280D | rs28575268-T |
| LTBP2 | rs73296215-T |
| FERMT2 | rs12147852-G |
| SOS2 | rs61755579-C |
| LMO7 | rs7338461-A |
| LINC00540 | rs9316969-T |
| ATXN2 | rs11065979-C |
| TMEM119 | rs73191227-A |
| ETS1 | rs7924522-A |
| ARHGEF12 | rs11217878-A |
| MFRP | rs883245-A |
| ME3 | rs746491-A |
| PTPRJ | rs7123436-A |
| MYBPC3 | rs2697920-T |
| MIR8068 | rs10767734-T |
| PLEKHA7 | rs4141194-A |
| 10g26 | rs1556659-C |
| ADAM12 | rs10901553-A |
| EXOC6 | rs12413181-A |
| KIF11 | rs9419741-G |
| ABO | rs8176747-C |
| ANGPTL2 | rs11795066-A |
| LMX1B | rs12377624-G |
| LMX1B | rs10819187-G |
| LMX1B | rs6478746-G |
| ABCA1 | rs2472496-G |
| PCSK5 | rs10869665-C |
| FBXO32 | rs62520914-A |
| ANGPT1 | rs44496939-G |
| ANGPT1 | rs66602224-A |
| ANGPT1 | rs2022945-G |
| ABRA | rs1381486-G |
| ABRA | rs1001989-T |
| 8q21 | rs35174414-C |
| C8orf48 | rs12548673-C |
| ANGPT2 | rs76020419-G |
| CTTNBP2 | rs2188836-T |
| CAV2 | rs10281637-C |
| TES | rs55892100-A |
| SEMA3C | rs327716-A |
| POU6F2 | rs12674371-G |
| LOC154449 | rs3013274-G |
| PDE7B | rs9494457-T |
| LIN28B | rs111307712-C |
| PKHD1 | rs17752199-A |
| RUNX2 | rs1755056-C |
| SUPT3H | rs11752730-C |
| TNXB | rs3134954-T |
| GMDS | rs9405157-T |
| GMDS | rs3778523-T |
| FOXC1 | rs2745572-A |
| EXOC2 | rs113985657-T |
| FER | rs73220177-G |
| PTCD2 | rs10036789-C |
| ANKH | rs31918-C |
| EMCN | rs1501086-T |
| SCFD2 | rs6554074-G |
| AFAP1 | rs28500712-A |
| AFAP1 | rs28520091-C |
| DGKG | rs9853115-T |
| FNDC3B | rs16856911-C |
| MECOM | rs73174309-C |
| LRIG1 | rs6781336-A |
| TRAF3IP1 | rs57435966-C |
| TNS1 | rs3791979-C |
| PARD3B | rs16837021-C |
| FMNL2 | rs1579050-G |
| NPAS2 | rs11123857-A |
| ANTXR1 | rs6732795-C |
| EFEMP1 | rs4672075-G |
| SPTBN1 | rs4627617-G |
| SIX3 | rs163524-A |
| THADA | rs113542380-A |
| BRE | rs10189434-T |
| LYPLAL1-AS1 | rs73111535-C |
| TMCO1 | rs10918274-T |
| ST7L | rs12045227-A |
| LINC01364 | rs35638741-A |

| Locus | SNP (Effect Allele) |
| --- | --- |
| COL24A1 | rs2279948-A |
| RSPO1 | rs4074961-T |
| TRAPPC3 | rs12123086-G | and/or
wherein the genetic loci or markers having an association with an increased vertical cup to disc ratio comprise greater than 16% of the genetic loci or markers having an association with an increased vertical cup to disc ratio listed below:

| Locus | SNP (Effect Allele) |
| --- | --- |
| PRDM16 | rs12024620C |
| WLS | rs34151819C |
| TGFB2 | rs1417488C |
| ZNF678 | rs77271542A |
| EFEMP1 | rs376096585C |
| ACOXL | rs2880192A |
| FMNL2 | rs1579050A |
| RARB | rs4858682C |
| TRIM71 | rs34010125T |
| C3orf38 | 3:88379094AT |
| MIR548G | rs4928176G |
| ABI3BP | rs9827694G |
| AMOTL2 | rs143351962C |
| GSX2 | rs2162137C |
| PDGFRA | rs565335773G |
| ANKRD55 | rs158653G |
| LOC102467147 | rs30372T |
| ADAMTS19 | rs11749004T |
| VDAC1 | 5:133393380GA |
| GMDS | rs2761235C |
| SRSF3 | rs12211825C |
| HSF2 | rs2684249T |
| TWISTNB | rs4518562A |
| CREB5 | rs7805378A |
| SGK223 | rs2976932T |
| EYA1 | rs12543430T |
| SH3GL2 | rs78542921T |
| NEBL | 10:21462896GGC |
| CYP26A1 | rs17108260A |
| DCDC5 | rs10835721G |
| HIPK3 | rs2753411A |
| TMEM135 | rs2445575T |
| FAM76B | rs11021221T |
| KRR1 | rs6582298G |
| RIC8B | rs9651957T |
| MYO16 | rs10162202T |
| COL4A1 | 13:110778747CCTTTT |
| PRMT5 | rs4982708G |
| FLRT2 | rs984586G |
| LOXL1 | rs893817G |
| FENDRR | rs35526343C |
| PPP1R9B | rs847688T |
| BCAS3 | rs2204928C |
| LPPR3 | rs146055611C |
| THEG5 | rs8102936G |
| CASC20 | rs6140010A |
| MAPRE1 | rs3831804T |
| TRIOBP | rs71324877G |
| DHRS3 | rs6690264A |
| RPE65 | rs3125918A |
| CDC7-TGFBR3 | rs4658101A |
| MIR548G | rs6804624T |
| PDZD2 | rs72759609T |
| DUSP1 | rs34471628A |
| RREB1 | rs4960297C |
| DGKB | rs10260511C |
| CDKN2B-AS1 | rs7039467A |
| CDKN2B-AS1 | rs7866783A |
| ATOH7 | rs7916697A |
| HSPA12A | rs11197820G |
| SSSCA1-AS1 | rs1346A |

| Locus | SNP (Effect Allele) |
| --- | --- |
| ADAMTS8 | rs4936099C |
| TMTC2 | rs61952219G |
| TMTC2 | 12:83973565TTCTC |
| ZNF664-FAM101A | rs4765353-G |
| DCLK1 | rs9546383-T |
| DDHD1 | rs2251171-G |
| PPM1A | rs10162287-C |
| ASB7 | rs148139847-C |
| SALL1 | rs373836950-C |
| SALL1 | rs8053277-T |
| SALL1 | rs2720429-G |
| CHEK2 | rs7287609-C |
| CHEK2 | rs6005840-A |
| HORMAD2 | rs713875-C |
| CARD10 | rs113605227-A. |

2. The method according to claim 1, wherein the selected genetic loci or markers comprise genetic loci or markers having an association with glaucoma and genetic loci or markers having an association with increased intraocular pressure, and genetic loci or markers having an association with an increased vertical cup to disk ratio.

3. The method according to claim 1, wherein the selected genetic loci or markers comprise genetic loci or markers having an association with a multi-trait test of glaucoma, intraocular pressure and vertical cup to disc ratio selected from one or more of:

| Locus | SNP |
| --- | --- |
| COL8A2 | rs274760 |
| RSPO1 | rs10796912 |
| COL24A1 | rs12068500 |
| LOC100505768 | rs12139208 |
| HSP90B3P | rs4658101 |
| ST7L | rs12045227 |
| TMCO1 | rs10918274 |
| LOC643723 | rs73111535 |
| BRE | rs6741499 |
| THADA | rs113542380 |
| SIX3 | rs163524 |
| SPTBN1 | rs74259971 |
| PNPT1 | rs1084524 |
| MIR4778 | rs13009933 |
| ANTXR1 | rs6732795 |
| NPAS2 | rs56405342 |
| FMNL2 | rs1579050 |
| PARD3B | rs62172701 |
| MIR4776-1 | rs62188040 |
| RARB | rs1286771 |
| SEMA3F | rs2526385 |
| KBTBD8 | rs1867409 |
| CADM2 | rs66500121 |
| KALRN | rs893830 |
| TSC22D2 | rs11710845 |
| MECOM | rs9816799 |
| LOC253573 | rs9853115 |
| LPP | rs4420855 |
| AFAP1 | rs28795989 |
| AFAP1 | rs6838291 |
| VEGFC | rs447324 |
| ANKH | rs76325372 |
| PTCD2 | rs4703855 |
| FER | rs73220190 |
| CDC25C | rs11567976 |
| JAKMIP2 | rs1347141 |
| EXOC2 | rs57111852 |
| FOXC1 | rs2745572 |
| GMDS | rs722585 |
| GMDS | rs6914444 |
| SUPT3H | rs2145826 |
| PKHD1 | rs2439042 |
| PDE7B | rs9494457 |

-continued

| Locus | SNP |
| --- | --- |
| TMEM181 | rs4709210 |
| LOC154449 | rs2935072 |
| THSD7A | rs2526101 |
| BBS9 | rs1362227 |
| POU6F2 | rs10435033 |
| SEMA3C | rs327712 |
| RELN | rs7799028 |
| TES | rs2896175 |
| CAV2 | rs59454355 |
| CTTNBP2 | rs2188836 |
| PRKAG2 | rs4128399 |
| PKIA | rs4412362 |
| ABRA | rs2881425 |
| ANGPT1 | rs2022945 |
| ANGPT1 | rs1283696 |
| FBXO32 | rs17339357 |
| CDKN2B-AS1 | rs944801 |
| PCSK5 | rs10869665 |
| ABCA1 | rs2472493 |
| LMX1B | rs2275241 |
| RALGPS1 | rs62580791 |
| ABO | rs12216891 |
| ARHGAP12 | rs11008626 |
| BICC1 | rs7089636 |
| KCNMA1 | rs1616405 |
| CYP26A1 | rs12778014 |
| PLCE1 | rs2274224 |
| PLEKHA7 | rs4141194 |
| METTL15 | rs12280392 |
| PTPRJ | rs56319620 |
| OR4C46 | rs4434990 |
| OR4A16 | rs11229165 |
| MALAT1 | rs4102217 |
| ME3 | rs11234741 |
| TYR | rs1126809 |
| ARHGEF12 | rs58073046 |
| ETS1 | rs7924522 |
| ADAMTS8 | rs4936100 |
| TMTC2 | rs324762 |
| SH2B3 | rs3184504 |
| KLF5 | rs9530143 |
| LMO7 | rs9544024 |
| COL4A1 | rs56152426 |
| SPTSSA | rs72669675 |
| SOS2 | rs61755579 |
| FERMT2 | rs8009633 |
| SIX1 | rs35155027 |
| NPC2 | rs73294447 |
| HERC2 | rs12913832 |
| ZNF280D | rs4601984 |
| VPS13C | rs2249195 |
| SALL1 | rs11859314 |
| CDH11 | rs74984957 |
| ADAMTS18 | rs75265191 |
| FANCA | rs3743861 |
| SMG6 | rs1563966 |
| GAS7 | rs8064739 |
| GAS7 | rs9913911 |
| FLJ40194 | rs36006455 |
| BCAS3 | rs3785856 |
| PTBP1 | rs351973 |
| KANK2 | rs440677 |
| CASC20 | rs6140009 |
| LOC339593 | rs34952318 |
| LOC339568 | rs6065171 |
| PTPN1 | rs7273775 |
| TXNRD2 | rs73148965 |
| CHEK2 | rs738722 |
| EMID1 | rs9608740 |
| SYN3 | rs756481 |
| TRIOBP | rs4821712. |

4. The method according to claim 1, wherein the genetic loci or markers having an association with glaucoma comprises genetic loci or markers having an association with advanced glaucoma disease.

5. The method according to claim 1, wherein the genetic loci or markers having an association with an increased vertical cup to disk ratio comprises genetic loci or markers having an association with an increased vertical cup to disk ratio corrected for optic nerve head size.

6. The method according to claim 1, wherein the determining of the risk score further comprises using information relating to one or more clinical features of the subject.

7. The method according to claim 6, wherein the one or more clinical features comprise one or more of age, gender, family history of glaucoma, intraocular pressure, vertical cup to disc ratio, corrected vertical cup to disk ratio, data from optical coherence tomography of the optic nerve head, retinal nerve fibre layer, retinal ganglion cell layer, data from automated perimetry, ocular biomechanical, and systemic vascular factors.

8. The method according to claim 1, wherein the method comprises stratifying the risk score and assessing the risk based on the risk stratification.

9. The method according to claim 1, wherein an increased risk score is indicative of one or more of an increased risk of primary open angle glaucoma, an increased risk of advanced glaucoma, an increased risk of non-advanced glaucoma, an earlier age of onset of primary open angle glaucoma, an earlier age of clinical diagnosis of glaucoma, an increased likelihood of surgery required for glaucoma; an increased risk of progression in early stage glaucoma, an increased risk of blindness from glaucoma, or need for treatment for glaucoma.

10. The method of claim 1, wherein the selected genetic loci or markers comprise:
   genetic loci or markers having an association with glaucoma; and
   genetic loci or markers having an association with increased intraocular pressure; and
   genetic loci or markers having an association with an increased vertical cup to disk ratio; and
   genetic loci or markers having an association with a multi-trait test of glaucoma, intraocular pressure and vertical cup to disc ratio.

11. The method of claim 1, wherein the high risk score is a risk score in the top 5%, 10%, 20%, or 33% of the score distribution.

12. The method of claim 1, wherein the subject is a MYOC p.Gln368Ter carrier.

13. A method of treating primary open angle glaucoma in a subject, the method comprising:
   (i) determining a risk score for primary open angle glaucoma in the subject on the basis of the genetic content of the subject at a plurality of selected genetic loci or markers and thereby assessing the risk of primary open angle glaucoma in the subject, wherein:
      (a) the selected genetic loci or markers comprise (ai) genetic loci or markers having an association with glaucoma, and (aii) genetic loci or markers having an association with increased intraocular pressure, and (aiii) genetic loci or markers having an association with an increased vertical cup to disk ratio, and/or
      (b) the selected genetic loci or markers have an association with a multi-trait test of glaucoma, intraocular pressure and vertical cup to disc ratio,
      wherein the association comprises a threshold for genome-wide significance of p $<5\times10^{-8}$;
   (ii) identifying the subject as having a high risk score; and
   (iii) administering to the subject with a high risk score one or more of laser treatment, selective laser trabeculoplasty, administration of a drug, surgical intervention, and incisional surgery or laser surgery, alone or in combination with drug administration; or wherein the genetic loci or markers having an association with increased intraocular pressure comprise greater than 7% of the genetic loci or markers having an association with increased intraocular pressure listed below:

| Locus | SNP (Effect Allele) |
|---|---|
| TRIOBP | rs5756813-G |
| SYN3 | rs756481-A |
| EMID1 | rs9608740-C |
| TXNRD2 | rs76945759-G |
| LINC00314 | rs4629237-A |
| PTPN1 | rs6095946-C |
| LINC01370 | rs6065171-T |
| LOC339593 | rs34952318-G |
| CPXM1 | rs215543-G |
| ZNF516 | rs1047922-C |
| BCAS3 | rs1558225-G |
| FLJ40194 | rs11079868-G |
| NSF | rs199529-C |
| GAS7 | rs9913911-A |
| GAS7 | rs10852918-G |
| FANCA | rs3743860-T |
| ADAMTS18 | rs12444539-T |
| IL34 | rs35381200-C |
| CDH11 | rs1874458-G |
| VPS13C | rs4775427-T |
| ZNF280D | rs28575268-T |
| LTBP2 | rs73296215-T |
| FERMT2 | rs12147852-G |
| SOS2 | rs61755579-C |
| LMO7 | rs7338461-A |
| LINC00540 | rs9316969-T |
| ATXN2 | rs11065979-C |
| TMEM119 | rs73191227-A |
| ETS1 | rs7924522-A |
| ARHGEF12 | rs11217878-A |
| MFRP | rs883245-A |
| ME3 | rs746491-A |
| PTPRJ | rs7123436-A |
| MYBPC3 | rs2697920-T |
| MIR8068 | rs10767734-T |
| PLEKHA7 | rs4141194-A |
| 10q26 | rs1556659-C |
| ADAM12 | rs10901553-A |
| EXOC6 | rs12413181-A |
| KIF11 | rs9419741-G |
| ABO | rs8176747-G |
| ANGPTL2 | rs11795066-A |
| LMX1B | rs12377624-G |
| LMX1B | rs10819187-G |
| LMX1B | rs6478746-G |
| ABCA1 | rs2472496-G |
| PCSK5 | rs10869665-C |
| FBXO32 | rs62520914-A |
| ANGPT1 | rs4496939-G |
| ANGPT1 | rs66602224-A |
| ANGPT1 | rs2022945-G |
| ABRA | rs1381486-G |
| ABRA | rs1001989-T |
| 8g21 | rs35174414-C |
| C8orf48 | rs12548673-C |
| ANGPT2 | rs76020419-G |
| CTTNBP2 | rs2188836-T |
| CAV2 | rs10281637-C |
| TES | rs55892100-A |
| SEMA3C | rs327716-A |
| POU6F2 | rs12674371-G |
| LOC154449 | rs3013274-G |
| PDE7B | rs9494457-T |
| LIN28B | rs111307712-C |
| PKHD1 | rs17752199-A |
| RUNX2 | rs1755056-C |
| SUPT3H | rs11752730-C |
| TNXB | rs3134954-T |
| GMDS | rs9405157-T |
| GMDS | rs3778523-T |
| FOXC1 | rs2745572-A |
| EXOC2 | rs113985657-T |
| FER | rs73220177-G |
| PTCD2 | rs10036789-C |
| ANKH | rs31918-C |
| EMCN | rs1501086-T |
| SCFD2 | rs6554074-G |
| AFAP1 | rs28500712-A |
| AFAP1 | rs28520091-C |
| DGKG | rs9853115-T |
| FNDC3B | rs16856911-C |
| MECOM | rs73174309-C |
| LRIG1 | rs6781336-A |
| TRAF3IP1 | rs57435966-C |
| TNS1 | rs3791979-C |
| PARD3B | rs16837021-C |
| FMNL2 | rs1579050-G |
| NPAS2 | rs11123857-A |
| ANTXR1 | rs6732795-C |
| EFEMP1 | rs4672075-G |
| SPTBN1 | rs4627617-G |
| SIX3 | rs163524-A |
| THADA | rs113542380-A |
| BRE | rs10189434-T |
| LYPLAL1-AS1 | rs73111535-C |
| TMCO1 | rs10918274-T |
| ST7L | rs12045227-A |
| LINC01364 | rs35638741-A |
| COL24A1 | rs2279948-A |
| RSPO1 | rs4074961-T |
| TRAPPC3 | rs12123086-G | and/or wherein the genetic loci or markers having an association with an increased vertical cup to disc ratio comprise greater than 16% of the genetic loci or markers having an association with an increased vertical cup to disc ratio listed below:

| Locus | SNP (Effect Allele) |
|---|---|
| PRDM16 | rs12024620C |
| WLS | rs34151819C |
| TGFB2 | rs1417488C |
| ZNF678 | rs77271542A |
| EFEMP1 | rs376096585C |
| ACOXL | rs2880192A |
| FMNL2 | rs1579050A |
| RARB | rs4858682C |
| TRIM71 | rs34010125T |
| C3orf38 | 3:88379094AT |
| MIR548G | rs4928176G |
| ABI3BP | rs9827694G |
| AMOTL2 | rs143351962C |
| GSX2 | rs2162137C |
| PDGFRA | rs565335773G |
| ANKRD55 | rs158653G |
| LOC102467147 | rs30372T |
| ADAMTS19 | rs11749004T |
| VDAC1 | 5:133393380GA |
| GMDS | rs2761235C |
| SRSF3 | rs12211825C |
| HSF2 | rs2684249T |
| TWISTNB | rs4518562A |
| CREB5 | rs7805378A |
| SGK223 | rs2976932T |
| EYA1 | rs12543430T |
| SH3GL2 | rs78542921T |
| NEBL | 10:21462896GGC |
| CYP26A1 | rs17108260A |
| DCDC5 | rs10835721G |
| HIPK3 | rs2753411A |
| TMEM135 | rs2445575T |

| Locus | SNP (Effect Allele) |
|---|---|
| FAM76B | rs11021221T |
| KRR1 | rs6582298G |
| RIC8B | rs9651957T |
| MYO16 | rs10162202T |
| COL4A1 | 13:110778747CCTTTT |
| PRMT5 | rs4982708G |
| FLRT2 | rs984586G |
| LOXL1 | rs893817G |
| FENDRR | rs35526343C |
| PPP1R9B | rs847688T |
| BCAS3 | rs2204928C |
| LPPR3 | rs146055611C |
| THEG5 | rs8102936G |
| CASC20 | rs6140010A |
| MAPRE1 | rs3831804T |
| TRIOBP | rs71324877G |
| DHRS3 | rs6690264A |
| RPE65 | rs3125918A |
| CDC7-TGFBR3 | rs4658101A |
| MIR548G | rs6804624T |
| PDZD2 | rs72759609T |
| DUSP1 | rs34471628A |
| RREB1 | rs4960297C |
| DGKB | rs10260511C |
| CDKN2B-AS1 | rs7039467A |
| CDKN2B-AS1 | rs7866783A |
| ATOH7 | rs7916697A |
| HSPA12A | rs11197820G |
| SSSCA1-AS1 | rs1346A |
| ADAMTS8 | rs4936099C |
| TMTC2 | rs61952219G |
| TMTC2 | 12:83973565TTCTC |
| ZNF664-FAM101A | rs4765353-G |
| DCLK1 | rs9546383-T |
| DDHD1 | rs2251171-G |
| PPM1A | rs10162287-C |
| ASB7 | rs148139847-C |
| SALL1 | rs373836950-C |
| SALL1 | rs8053277-T |
| SALL1 | rs2720429-G |
| CHEK2 | rs7287609-C |
| CHEK2 | rs6005840-A |
| HORMAD2 | rs713875-C |
| CARD10 | rs113605227-A | and wherein the subject has at least one family member diagnosed with primary open angle glaucoma or wherein the subject has at least one test result suggestive of glaucoma.

* * * * *